(12) United States Patent
Winkler et al.

(10) Patent No.: US 11,266,413 B2
(45) Date of Patent: Mar. 8, 2022

(54) OCCLUSION CLIP

(71) Applicant: AtriCure, Inc., Mason, OH (US)

(72) Inventors: Matthew J. Winkler, Liberty Township, OH (US); Kenneth Lance Miller, Hamilton, OH (US); Matthew Monti, Cincinnati, OH (US); Todd Frangolis, Cincinnati, OH (US); Nicholas Bailey, Cincinnati, OH (US); Robert M. Trusty, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 130 days.

(21) Appl. No.: 14/549,811

(22) Filed: Nov. 21, 2014

(65) Prior Publication Data
US 2016/0008001 A1     Jan. 14, 2016

Related U.S. Application Data

(60) Provisional application No. 61/906,924, filed on Nov. 21, 2013.

(51) Int. Cl.
*A61B 17/12*      (2006.01)
*A61B 17/122*     (2006.01)

(52) U.S. Cl.
CPC .... *A61B 17/12031* (2013.01); *A61B 17/1227* (2013.01); *A61B 17/12099* (2013.01)

(58) Field of Classification Search
CPC ... A61B 17/1227; A61B 17/122; A61B 17/12; A61B 17/0487; A61B 17/08;
(Continued)

(56) References Cited

U.S. PATENT DOCUMENTS

| 119,938 A | 10/1871 | Mellish |
| 1,152,492 A | 9/1915 | Deming |

(Continued)

FOREIGN PATENT DOCUMENTS

| WO | 2015/077528 | 3/2015 |
| WO | 2015/077528 | 4/2015 |

(Continued)

*Primary Examiner* — Julian W Woo
(74) *Attorney, Agent, or Firm* — Dorton & Willis, LLP; Ryan Willis

(57) ABSTRACT

An occlusion clip comprising: (a) a spring; (b) a first runner including a first open top and a first open end adjacent the first open top, the first runner including a first interior camming surface partially delineating a first interior cavity that is open by way of the first open top and the first open end; (c) a second runner including a second open top and a second open end adjacent the second open top, the second runner including a second interior camming surface partially delineating a second interior cavity that is open by way of the second open top and the second open end, where the spring is configured to be coupled to the first runner and the second runner, where the first interior cavity is configured to receive a first portion of the spring, where the second interior cavity is configured to receive a second portion of the spring, where the first camming surface is configured to engage a first cam of the spring, and where the second camming surface is configured to engage a second cam of the spring.

47 Claims, 37 Drawing Sheets

(58) Field of Classification Search
CPC . A61B 17/083; A61B 17/22; A61B 17/12022; A61B 17/12027; A61B 17/12031; A61B 17/12036; A61B 17/1204; A61B 17/12099; A61B 2017/12004; A61B 2017/00584; A61B 17/42; Y10T 24/44479; Y10T 24/44385; Y10T 24/44393; Y10T 24/44496; Y10T 24/203; Y10T 24/202; Y10T 24/44769; Y10T 24/4488; Y10T 24/44778; Y10T 24/44641; Y10T 24/1391; Y10T 403/7176; F16B 2/245; F16B 2/246; A47G 25/483; A47G 25/482; A47G 25/486; A47G 25/487; D06F 55/00; D06F 55/02; A45D 6/045; H01R 11/24
USPC .......................... 24/500, 499, 523, 613, 424
See application file for complete search history.

(56) References Cited

U.S. PATENT DOCUMENTS

| | | | |
|---|---|---|---|
| 1,162,578 A * | 11/1915 | De Forge | D06F 55/00 24/530 |
| 1,205,889 A | 11/1916 | Halvorson | |
| 1,357,233 A * | 11/1920 | Hagelstein | D06F 55/02 24/501 |
| 1,491,941 A * | 4/1924 | Wood | D06F 55/02 24/501 |
| 2,051,174 A | 8/1936 | Levigard | |
| 2,540,722 A * | 2/1951 | Gardner | D06F 55/02 24/567 |
| 2,593,201 A * | 4/1952 | Saunders | D06F 55/02 24/500 |
| 2,815,557 A * | 12/1957 | Jorgensen | F16B 2/10 24/510 |
| 3,503,396 A * | 3/1970 | Pierie | A61B 17/282 24/517 |
| 3,503,398 A * | 3/1970 | Raible | A61B 17/282 606/207 |
| 3,579,751 A * | 5/1971 | Jonckheere | A61B 17/1227 606/158 |
| 4,120,302 A * | 10/1978 | Ziegler | A61B 17/122 15/250.48 |
| 4,231,360 A * | 11/1980 | Zloczysti | A62B 9/06 128/201.18 |
| RE32,269 E * | 10/1986 | Bisk | A47G 25/32 223/91 |
| 4,716,634 A * | 1/1988 | Fan | A47G 25/485 223/91 |
| 4,821,719 A * | 4/1989 | Fogarty | A61B 17/122 606/158 |
| 5,063,645 A * | 11/1991 | Crespo | D06F 55/02 24/501 |
| 5,075,935 A * | 12/1991 | Abdi | A47G 25/32 24/500 |
| 5,171,252 A | 12/1992 | Friedland | |
| 5,402,558 A * | 4/1995 | Santapa | A47G 25/485 223/91 |
| 5,634,932 A | 6/1997 | Schmidt | |
| 5,653,720 A | 8/1997 | Johnson et al. | |
| 5,695,505 A | 12/1997 | Yoon | |
| 5,707,377 A | 1/1998 | Keller et al. | |
| 5,843,101 A * | 12/1998 | Fry | A61B 17/122 227/902 |
| 6,007,552 A * | 12/1999 | Fogarty | A61B 17/02 606/157 |
| 6,023,818 A * | 2/2000 | Shang | B25B 5/06 24/501 |
| 6,099,539 A * | 8/2000 | Howell | A61B 17/122 606/151 |
| 6,193,732 B1 | 2/2001 | Frantzen et al. | |
| 6,579,304 B1 * | 6/2003 | Hart | A61B 17/02 606/157 |
| 7,881,762 B2 * | 2/2011 | Kling | A61B 5/14552 600/323 |
| 8,172,870 B2 | 5/2012 | Shipp | |
| 8,201,310 B1 * | 6/2012 | Abdi | A47G 25/48 24/499 |
| 8,578,571 B2 * | 11/2013 | Schmidt | F16B 2/005 24/536 |
| 2003/0083677 A1 | 5/2003 | Damarati | |
| 2005/0021062 A1 | 1/2005 | Dennis | |
| 2005/0240219 A1 * | 10/2005 | Kahle | A61B 17/122 606/207 |
| 2005/0277959 A1 * | 12/2005 | Cosgrove | A61B 17/12 606/151 |
| 2006/0100649 A1 * | 5/2006 | Hart | A61B 17/0643 606/157 |
| 2007/0149989 A1 * | 6/2007 | Santilli | A61B 17/1227 606/157 |
| 2007/0213747 A1 * | 9/2007 | Monassevitch | A61B 17/0643 606/151 |
| 2008/0004637 A1 * | 1/2008 | Klassen | A61B 17/122 606/142 |
| 2008/0244880 A1 * | 10/2008 | Rankin | D06F 55/02 24/500 |
| 2009/0012545 A1 * | 1/2009 | Williamson, IV | A61B 17/083 606/157 |
| 2009/0240266 A1 * | 9/2009 | Dennis | A61B 17/1227 606/151 |
| 2011/0046437 A1 * | 2/2011 | Kassab | A61F 5/0086 600/37 |
| 2011/0046641 A1 * | 2/2011 | Kassab | A61F 5/0086 606/139 |
| 2011/0288571 A1 * | 11/2011 | Steinhilper | A61B 17/1227 606/158 |
| 2011/0313437 A1 * | 12/2011 | Yeh | A61B 17/122 606/158 |
| 2014/0058411 A1 * | 2/2014 | Soutorine | A61B 17/122 606/142 |
| 2014/0142597 A1 | 5/2014 | Winkler et al. | |
| 2014/0172084 A1 | 6/2014 | Callas et al. | |
| 2016/0008001 A1 | 1/2016 | Winkler et al. | |

FOREIGN PATENT DOCUMENTS

| | | |
|---|---|---|
| WO | 2015/077528 | 5/2015 |
| WO | 2016/094647 | 2/2016 |
| WO | 2015/077528 | 5/2016 |

* cited by examiner

OCCLUSION CLIP

CROSS REFERENCE TO RELATED APPLICATIONS

The present application claims the benefit of U.S. Provisional Patent Application Ser. No. 61/906,924, entitled, "OCCLUSION CLIP," filed Nov. 21, 2013, the disclosure of which is incorporated herein by reference.

RELATED ART

1. Field of the Invention

The present invention is directed to occlusion clips and, more specifically, to open ended clips capable of occluding bodily tissue.

2. Brief Discussion of Related Art

Embolic stroke is the nation's third leading killer for adults. Embolic stroke is also a major cause of disability. The most common cause of embolic stroke is thrombus formation in the left appendage of the atrium. In almost all atrial fibrillation (AF) patients suffering from embolic stroke, a thrombus clot forms in the appendage of the left atrium.

The primary therapy for the prevention of stroke in AF patients is the administration of oral anticoagulants. Although somewhat effective, there are numerous side effects, including bleeding and lifestyle compromises.

Another therapy for the prevention of stroke in AF patients is the introduction of biomaterials into the left atrial appendage to plug the appendage. But these materials may break down over time and allow for a cavity of sufficient size to foster clot formation.

Still another approach involves open chest and thoroscopic surgical procedures to remove or oversew the left atrial appendage. Alternatively, a percutaneous endocardial approach may be utilized to isolate the left atrial appendage from the inside of the heart. By way of example, a barrier or other device is anchored in the chamber of the left atrial appendage to prevent the passage of blood into and out of the chamber and thereby prevent clot formation. But, again, the barrier may break down and result in clotting.

Endoscopic stapling devices, suture loops tied to the base of the appendage, and clips pinching the appendage from the outside surface to the base to close the appendage are used by physicians to isolate and remove the left atrial appendage. In the case of a clip, this clip may be applied outside of the heart at the base of the appendage.

INTRODUCTION TO THE INVENTION

It is a first aspect of the present invention to provide an occlusion clip comprising: (a) a spring; (b) a first runner including a first open top and a first open end adjacent the first open top, the first runner including a first interior camming surface partially delineating a first interior cavity that is open by way of the first open top and the first open end; (c) a second runner including a second open top and a second open end adjacent the second open top, the second runner including a second interior camming surface partially delineating a second interior cavity that is open by way of the second open top and the second open end, where the spring is configured to be coupled to the first runner and the second runner, where the first interior cavity is configured to receive a first portion of the spring, where the second interior cavity is configured to receive a second portion of the spring, where the first camming surface is configured to engage a first cam of the spring, and where the second camming surface is configured to engage a second cam of the spring.

In a more detailed embodiment of the first aspect, at least one of the first runner and the second runner is pivotally mounted to the spring. In yet another more detailed embodiment, the first runner and the second runner are pivotally mounted to the spring. In a further detailed embodiment, the spring is configured to be removably coupled to at least one of the first runner and the second runner. In still a further detailed embodiment, the occlusion clip further includes a repositionable lock configured to fixedly mount at least one of the first runner and the second runner to the spring. In a more detailed embodiment, the repositionable lock includes a dowel received within an orifice associated with at least one of the spring, the first runner, and the second runner, the spring includes a first arm and a second arm, the first arm includes the first cam, and the second arm includes the second cam. In a more detailed embodiment, the repositionable lock includes a dowel received within an orifice associated with the first runner. In another more detailed embodiment, the repositionable lock includes a dowel received within an orifice associated with the first runner and the spring. In yet another more detailed embodiment, the repositionable lock includes a first dowel received within a first orifice associated with at least one of the first runner and the spring, and the repositionable lock includes a second dowel received within a second orifice associated with at least one of the second runner and the spring. In still another more detailed embodiment, the repositionable lock includes a third dowel received within a third orifice associated with at least one of the second runner and the spring.

In yet another more detailed embodiment of the first aspect, the repositionable lock is configured to allow pivotal movement between the spring and the first runner, and the repositionable lock is configured to inhibit at least one of rotational movement and longitudinal sliding movement between the spring and second runner. In yet another more detailed embodiment, the spring embodies a C-shape with a first leg and a second leg, and at least one of the first leg and the second leg includes a longitudinal variance. In a further detailed embodiment, the first leg and the second leg each include a longitudinal variance, and the longitudinal variance of the first leg forms a cavity along a longitudinal length of the first leg. In still a further detailed embodiment, the longitudinal variance of the second leg forms at least two cavities along a longitudinal length of the first leg. In a more detailed embodiment, the longitudinal variance of the first leg is configured to receive a first portion of the repositionable lock to mount the first leg to the first runner, and the longitudinal variance of the second leg is configured to receive a second portion and a third portion of the repositionable lock to mount the second leg to the second runner. In a more detailed embodiment, the longitudinal variance of the first leg comprises a first V-shaped notch, the longitudinal variance of the second leg comprises a second V-shaped notch and a third V-shaped notch, the first portion includes a first dowel, the second portion includes a second dowel, and the third portion includes a third dowel. In another more detailed embodiment, the first runner includes an arcuate tissue contacting surface, and the second runner includes an arcuate tissue contacting surface, the arcuate tissue contacting surface of the first runner faces the arcuate tissue contacting surface of the second runner when the first and second runners are mounted to the spring. In yet another more detailed embodiment, the occlusion clip further includes a first repositionable lock configured to fixedly mount the first runner to the spring, and a second repositionable lock configured to fixedly mount the second runner to the spring. In still another more detailed embodiment, the first runner includes at least one of a depression and an orifice configured to receive a portion of the first repositionable lock, and the second runner includes at least one of a depression and an orifice configured to receive a portion of the second repositionable lock.

In a more detailed embodiment of the first aspect, the first runner includes an orifice configured to receive a portion of the first repositionable lock, and the second runner includes an orifice configured to receive a portion of the second repositionable lock. In yet another more detailed embodiment, the orifice of the first runner includes a first pair of orifices, the orifice of the second runner includes a second pair of orifices, the first repositionable lock includes a first dowel configured to be received by the first pair of orifices of the first runner, and the second repositionable lock includes a second dowel configured to be received by the second pair of orifices of the second runner. In a further detailed embodiment, the spring embodies a C-shape with a first leg and a second leg, the first leg includes at least one of a cavity and an orifice configured to receive a first repositionable lock operative to mount the first leg to the first runner, and the second leg includes at least one of a cavity and an orifice configured to receive a second repositionable lock operative to mount the second leg to the second runner. In still a further detailed embodiment, a distal end of the first leg includes the first camming surface, a distal end of the second leg includes the second camming surface, the distal end of the first leg includes a cavity configured to receive a first repositionable lock operative to mount the first leg to the first runner, and the distal end of the second leg includes a cavity configured to receive a second repositionable lock operative to mount the second leg to the second runner. In a more detailed embodiment, the first runner includes at least one of a first runner cavity and a first runner orifice configured to receive a portion of the first repositionable lock, and the second runner includes at least one of a second runner cavity and a second runner orifice configured to receive a portion of the second repositionable lock. In a more detailed embodiment, the first runner includes a first runner orifice, the second runner includes a second runner orifice, the first repositionable lock comprises a first dowel configured to be concurrently received within the first runner orifice and the cavity of the first leg to mount the first leg to the first runner, and the second repositionable lock comprises a second dowel configured to be concurrently received within the second runner orifice and the cavity of the second leg to mount the second leg to the second runner. In another more detailed embodiment, a distal end of the first leg includes the first camming surface, a distal end of the second leg includes the second camming surface, the distal end of the first leg includes an orifice configured to receive a first repositionable lock operative to mount the first leg to the first runner, and the distal end of the second leg includes an orifice configured to receive a second repositionable lock operative to mount the second leg to the second runner. In yet another more detailed embodiment, the first runner includes at least one of a first runner cavity and a first runner orifice configured to receive a portion of the first repositionable lock, and the second runner includes at least one of a second runner cavity and a second runner orifice configured to receive a portion of the second repositionable lock. In still another more detailed embodiment, the first runner includes a first runner orifice, the second runner includes a second runner orifice, the first repositionable lock comprises a first dowel configured to be concurrently received within the first runner orifice and the orifice of the first leg to mount the first leg to the first runner, and the second repositionable lock comprises a second dowel configured to be concurrently received within the second runner orifice and the orifice of the second leg to mount the second leg to the second runner.

In yet another more detailed embodiment of the first aspect, the occlusion clip further includes a first repositionable lock configured to fixedly mount the first runner to the spring, and a second repositionable lock configured to fixedly mount the second runner to the spring, wherein the spring embodies a C-shape with a first leg and a second leg, the first leg includes at least one of a cavity and an orifice configured to receive at least a portion of the first repositionable lock, the second leg includes at least one of a cavity and an orifice configured to receive at least a portion of the second repositionable lock, and at least one of the cavity and the orifice of the first leg is longitudinally offset from the at least one of the cavity and the orifice of the second leg. In yet another more detailed embodiment, the first leg includes a projection extending toward the second leg, and at least one of the cavity and the orifice of the second leg longitudinally interposes the projection and at least one of the cavity and the orifice of the first leg. In a further detailed embodiment, the first leg includes a cavity configured to receive at least a portion of the first repositionable lock, the second leg includes a cavity configured to receive at least a portion of the second repositionable lock, and the cavity of the second leg longitudinally interposes the projection and the cavity of the first leg. In still a further detailed embodiment, the first leg includes an orifice configured to receive at least a portion of the first repositionable lock, the second leg includes an orifice configured to receive at least a portion of the second repositionable lock, and the orifice of the second leg longitudinally interposes the projection and the orifice of the first leg. In a more detailed embodiment, the occlusion clip further includes a first repositionable lock configured to fixedly mount the first runner to the spring, and a second repositionable lock configured to fixedly mount the second runner to the spring, where the spring embodies a C-shape with a first leg and a second leg, the first leg includes at least one of a cavity and an orifice configured to receive at least a portion of the first repositionable lock, the second leg includes at least one of a cavity and an orifice configured to receive at least a portion of the second repositionable lock, and the spring includes a first ancillary leg interposing the first leg and the second leg. In a more detailed embodiment, the first leg includes a cavity configured to receive at least a portion of the first repositionable lock, the second leg includes a cavity configured to receive at least a portion of the second repositionable lock, and the cavity of the second leg longitudinally interposes the projection and the cavity of the first leg. In another more detailed embodiment, the first leg includes an orifice configured to receive at least a portion of the first repositionable lock, the second leg includes an orifice configured to receive at least a portion of the second repositionable lock, and the orifice of the second leg longitudinally interposes the projection and the orifice of the first leg. In yet another more detailed embodiment, the first ancillary leg is configured to engage the first runner without being fixedly attached to the first runner.

In a more detailed embodiment of the first aspect, the occlusion clip further includes a first repositionable lock configured to fixedly mount the first runner to the spring, and a second repositionable lock configured to fixedly mount the second runner to the spring, where the spring embodies a C-shape with a first leg and a second leg, the first leg includes at least one of a cavity and an orifice configured to receive at least a portion of the first repositionable lock, the second leg includes at least one of a cavity and an orifice configured to receive at least a portion of the second repositionable lock, and the spring includes a first ancillary leg and a second ancillary leg. In yet another more detailed embodiment, the first leg includes a cavity configured to receive at least a portion of the first repositionable lock, the second leg includes a cavity configured to receive at least a portion of the second repositionable lock, and the cavity of the second leg longitudinally interposes the projection and the cavity of the first leg. In a further detailed embodiment, the first leg includes an orifice configured to receive at least a portion of the first repositionable lock, the second leg includes an orifice configured to receive at least a portion of the second repositionable lock, and the orifice of the second leg longitudinally interposes the projection and the orifice of the first leg. In still a further detailed embodiment, the first ancillary leg extends longitudinally between the first leg and the second leg, the second ancillary leg extends longitudinally between the first leg and the second leg, the first ancillary leg interpose the first leg and the second ancillary leg, and the second ancillary leg interpose the second leg and the first ancillary leg. In a more detailed embodiment, the first ancillary leg is configured to engage the first runner without being fixedly attached to the first runner, and the second ancillary leg is configured to engage the second runner without being fixedly attached to the second runner. In a more detailed embodiment, the first ancillary leg comprises a first pair of ancillary legs, the second ancillary leg comprises a second pair of ancillary legs, the first leg interposes the first pair of ancillary legs, and the second leg interposes the second pair of ancillary legs. In another more detailed embodiment, the first pair of ancillary legs is configured to engage the first runner without being fixedly attached to the first runner, and the second pair of ancillary legs is configured to engage the second runner without being fixedly attached to the second runner.

In yet another more detailed embodiment of the first aspect, the occlusion clip further includes a wedge removably coupled to the spring proximate a living hinge of the spring, where the spring includes a first leg and a first ancillary leg on a first side of the living hinge, the spring includes a second leg and a second ancillary leg on a second side of the living hinge, and the wedge is operative, when coupled to the spring, to change a force necessary to increase a separation between the first leg and the second leg. In yet another more detailed embodiment, the first ancillary leg extends longitudinally between the first leg and the second leg, the second ancillary leg extends longitudinally between the first leg and the second leg, the first ancillary leg interpose the first leg and the second ancillary leg, and the second ancillary leg interpose the second leg and the first ancillary leg. In a further detailed embodiment, the first ancillary leg is configured to engage the first runner without being fixedly attached to the first runner, and the second ancillary leg is configured to engage the second runner without being fixedly attached to the second runner. In still a further detailed embodiment, the first ancillary leg comprises a first pair of ancillary legs, the second ancillary leg comprises a second pair of ancillary legs, the first leg interposes the first pair of ancillary legs, and the second leg interposes the second pair of ancillary legs. In a more detailed embodiment, the first pair of ancillary legs is configured to engage the first runner without being fixedly attached to the first runner, and the second pair of ancillary legs is configured to engage the second runner without being fixedly attached to the second runner. In a more detailed embodiment, the occlusion clip further includes a fabric interposing the first and second runners. In another more detailed embodiment, the occlusion clip further includes a C-shaped fabric sleeve encapsulating the occlusion clip.

It is a second aspect of the present invention to provide an occlusion clamp comprising: (a) a spring comprising at least two elongated legs coupled together at a first end and independently repositionable with respect to one another at second, free ends so that the spring is open-ended, the spring having a dominant dimension measured from the first end to one of the second ends; (b) a first runner coupled to a first leg of the at least two elongated legs, the first runner comprising an elongated occlusion beam having an occlusion surface, the first runner having a dominant dimension; (c) a second runner coupled to a second leg of the at least two elongated legs, the second runner comprising an elongated occlusion beam having an occlusion surface, the second runner having a dominant dimension, where the spring is configured to bias the occlusion surface of the first runner toward the occlusion surface of the second runner, and where the dominant dimensions of the spring, first runner, and the second runner extend in generally the same direction.

In a more detailed embodiment of the second aspect, the second, free ends are spaced apart from one another along the dominant dimension of the spring, the first leg is coupled to the first runner at a first location, the second leg is coupled to the second runner at a second location and a third location, and the first location interposes the second and third locations along the dominant dimension. In yet another more detailed embodiment, the first leg traps a first pin to mount the first leg to the first runner, and the second leg traps a second pin and a third pin to mount the second leg to the second runner. In a further detailed embodiment, the first pin is mounted to the first runner, the second pin and the third pin are mounted to the second runner, the first leg includes a first discontinuity configured to receive the first pin so that the first leg interposes the first pin and the first runner to mount the first leg to the first runner, and the second leg includes a second discontinuity configured to receive the second pin and a third discontinuity configured to receive the third pin so that the second leg interposes the second pin and the second runner and interposes the third pin and the second runner to mount the second leg to the second runner. In still a further detailed embodiment, the first discontinuity comprises at least one of a U-shaped segment and a V-shaped segment, the second discontinuity comprises at least one of a U-shaped segment and a V-shaped segment, and the third discontinuity comprises at least one of a U-shaped segment and a V-shaped segment. In a more detailed embodiment, the first discontinuity is received within a trench of the first runner, and the second discontinuity and the third discontinuity are received within a trench of the second runner. In a more detailed embodiment, the spring includes at least one of a rectangular, circular, or oblong cross-section. In another more detailed embodiment, the second, free ends are spaced apart from one another along the dominant dimension of the spring, the first leg is coupled to the first runner at a first location, the second leg is coupled to the second runner at a second location and contacts the second runner at a third location, and the first location interposes the second and third locations along the dominant dimension. In yet another more detailed embodiment, a first pin is mounted to the first runner, a second pin is mounted to the second runner, the first leg traps the first pin to mount the first leg to the first runner, and the second leg traps the second pin to mount the second leg to the second runner. In still another more detailed embodiment, the first leg includes a first discontinuity configured to receive the first pin so that the first leg interposes the first pin and the first runner to mount the first leg to the first runner, and the second leg includes a second discontinuity configured to receive the second pin so that the second leg interposes the second pin and the second runner to mount the second leg to the second runner.

In yet another more detailed embodiment of the second aspect, the first discontinuity comprises at least one of a U-shaped segment and a V-shaped segment, and the second discontinuity comprises at least one of a U-shaped segment and a V-shaped segment. In yet another more detailed embodiment, the first discontinuity is received within a trench of the first runner, the second discontinuity is received within a trench of the second runner, the second leg includes a third discontinuity that is received within the trench of the second runner, and the third discontinuity occurs at the third location. In a further detailed embodiment, the spring further comprises a third leg mounted to at least one of the first leg and the second leg. In still a further detailed embodiment, the first leg is coupled to the first runner at a first location, the second leg is coupled to the second runner at a second location, and the first location is approximately the same as the second location along the dominant dimension. In a more detailed embodiment, a first pin is mounted to the first runner, a second pin is mounted to the second runner, the first leg traps the first pin to mount the first leg to the first runner, and the second leg traps the second pin to mount the second leg to the second runner. In a more detailed embodiment, the first leg includes a first orifice configured to receive the first pin so that the first leg interposes the first pin and the first runner to mount the first leg to the first runner, and the second leg includes a second orifice configured to receive the second pin so that the second leg interposes the second pin and the second runner to mount the second leg to the second runner. In another more detailed embodiment, the first orifice is at least partially received within a trench of the first runner, and the second orifice is at least partially received within a trench of the second runner. In yet another more detailed embodiment, the first and second legs delineate a U-shaped primary spring, and the third leg interposes the first and second legs. In still another more detailed embodiment, the third leg extends from a trough cooperatively formed by the intersection of the first and second legs, and the third leg comprises a partial U-shaped secondary spring.

In a more detailed embodiment of the second aspect, the spring further comprises a third leg mounted to at least one of the first leg and the second leg, and the spring further comprises a fourth leg mounted to at least one of the first leg and the second leg. In yet another more detailed embodiment, the first leg is coupled to the first runner at a first location, the second leg is coupled to the second runner at a second location, and the first location is approximately the same as the second location along the dominant dimension. In a further detailed embodiment, a first pin is mounted to the first runner, a second pin is mounted to the second runner, the first leg traps the first pin to mount the first leg to the first runner, and the second leg traps the second pin to mount the second leg to the second runner. In still a further detailed embodiment, the first leg includes a first orifice configured to receive the first pin so that the first leg interposes the first pin and the first runner to mount the first leg to the first runner, and the second leg includes a second orifice configured to receive the second pin so that the second leg interposes the second pin and the second runner to mount the second leg to the second runner. In a more detailed embodiment, the first orifice is at least partially received within a trench of the first runner, and the second orifice is at least partially received within a trench of the second runner. In a more detailed embodiment, the first and second legs delineate a U-shaped primary spring, the third leg interposes the first and second legs, and the fourth leg interposes the first and second legs. In another more detailed embodiment, the third and fourth legs extend from a trough cooperatively formed by the intersection of the first and second legs, and the third and fourth legs cooperate to delineate a U-shaped secondary spring.

In a more detailed embodiment of the second aspect, the first and second legs comprise a primary spring, the third leg interposes the first and second legs, and the fourth leg interposes the first and second legs. In yet another more detailed embodiment, the third and fourth legs extend from the first end, the first end includes a cavity opposite the third and fourth legs, and the spring further includes a wedge configured to be received within the cavity to impart bias of second ends toward one another. In a further detailed embodiment, the spring comprises a first spring, the occlusion clamp further comprising: (a) a second spring mounted to the first spring, the second spring comprising at least two elongated legs coupled together at a first end and independently repositionable with respect to one another at second, free ends so that the second spring is open-ended, the second spring having a dominant dimension measured from its first end to one of its second ends; and, (b) a third spring mounted to the first spring, the third spring comprising at least two elongated legs coupled together at a first end and independently repositionable with respect to one another at second, free ends so that the third spring is open-ended, the third spring having a dominant dimension measured from its first end to one of its second ends. In still a further detailed embodiment, the first leg is coupled to the first runner at a first location, the second leg is coupled to the second runner at a second location, and the first location is approximately the same as the second location along the dominant dimension. In a more detailed embodiment, a first pin is mounted to the first runner, a second pin is mounted to the second runner, the first leg traps the first pin to mount the first leg to the first runner, and the second leg traps the second pin to mount the second leg to the second runner. In a more detailed embodiment, the first leg includes a first orifice configured to receive the first pin so that the first leg interposes the first pin and the first runner to mount the first leg to the first runner, and the second leg includes a second orifice configured to receive the second pin so that the second leg interposes the second pin and the second runner to mount the second leg to the second runner. In another more detailed embodiment, the first orifice is at least partially received within a trench of the first runner, and the second orifice is at least partially received within a trench of the second runner. In yet another more detailed embodiment, the first spring comprises a U-shaped primary spring, the second spring comprises a first U-shaped secondary spring, and the third spring comprises a second U-shaped secondary spring. In still another more detailed embodiment, the first and second U-shaped secondary springs are mounted to opposite lateral sides of the U-shaped primary spring, and the second ends of each of the second and third U-shaped secondary springs include enlarged arcuate ends.

In yet another more detailed embodiment of the second aspect, a first of the second ends of the first spring, a first of the second ends of the second spring, and a first of the second ends of the third spring is at least partially received within a trench of the first runner, and a second of the second ends of the first spring, a second of the second ends of the second spring, and a second of the second ends of the third spring is at least partially received within a trench of the second runner. In yet another more detailed embodiment, the elongated occlusion beam of the first runner is linear and includes a linear occlusion surface, and the elongated occlusion beam of the second runner is linear and includes a linear occlusion surface. In a further detailed embodiment, the elongated occlusion beam of the first runner is linear and includes an arcuate occlusion surface, and the elongated occlusion beam of the second runner is linear and includes an arcuate occlusion surface. In still a further detailed embodiment, the elongated occlusion beam of the first runner is arcuate and includes an arcuate occlusion surface, and the elongated occlusion beam of the second runner is arcuate and includes an arcuate occlusion surface. In a more detailed embodiment, the elongated occlusion beam of the first runner is arcuate and includes a linear occlusion surface, and the elongated occlusion beam of the second runner is arcuate and includes a linear occlusion surface. In a more detailed embodiment, the spring is fabricated from at least one of a metal and a metal alloy, and at least one of the first runner and the second runner is fabricate from a polymer. In another more detailed embodiment, the clamp further includes a fabric interposing the first and second runners. In yet another more detailed embodiment, the clamp further includes a C-shaped fabric sleeve encapsulating the occlusion clamp.

DETAILED DESCRIPTION

Figure 1:
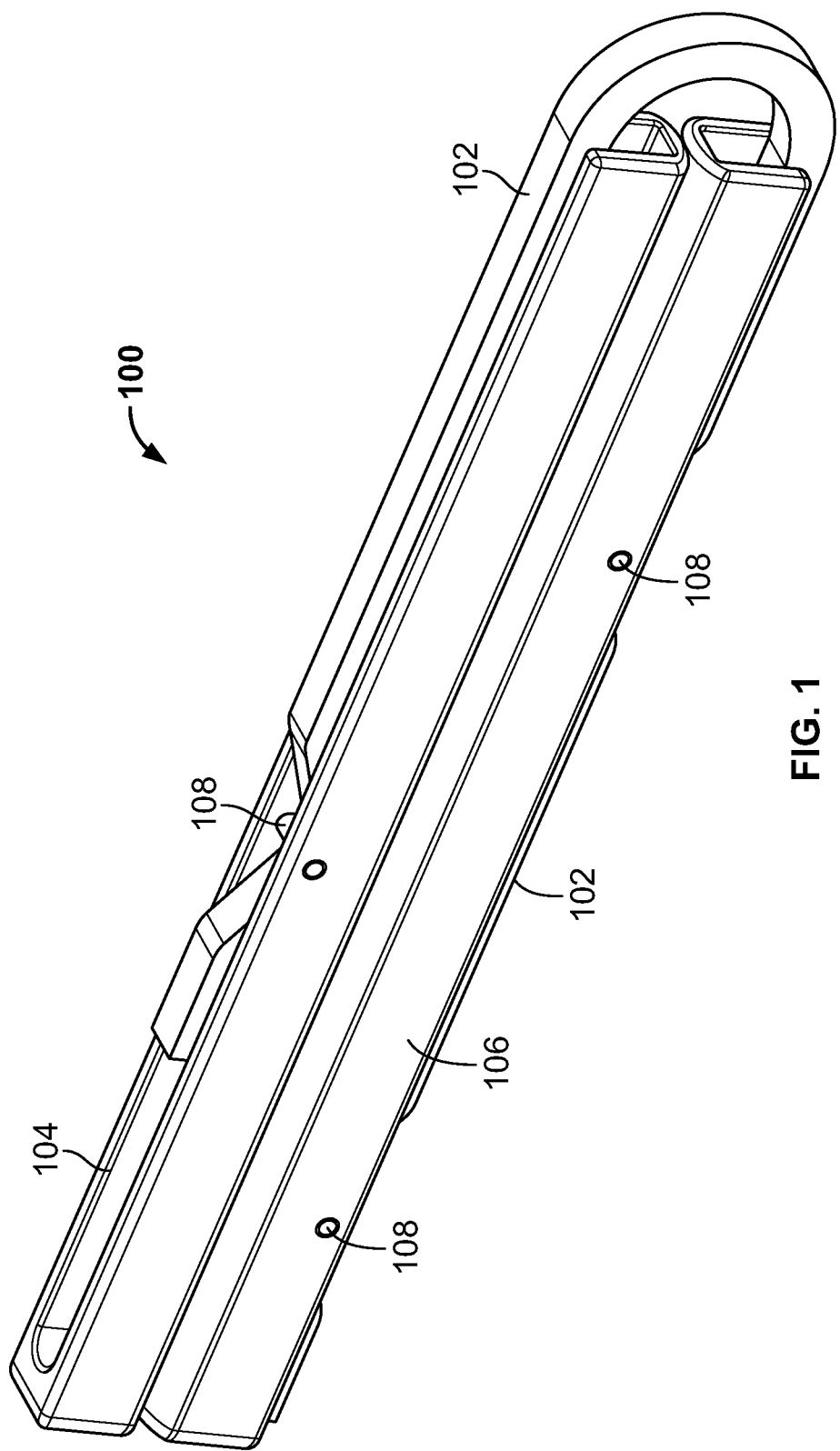
FIG. 1 is an elevated perspective view of a first exemplary occlusion clip in accordance with the present disclosure.
Figure 2:
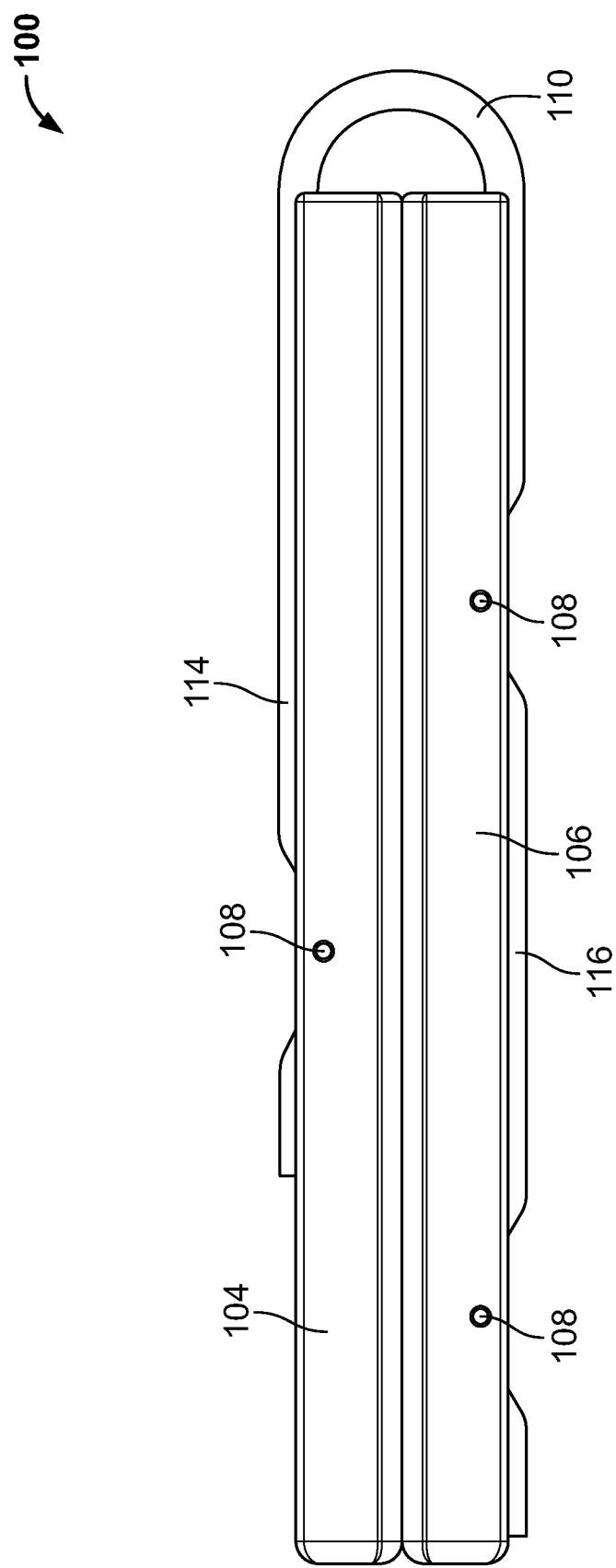
FIG. 2 is a left profile view of the first exemplary occlusion clip of FIG. 1.
Figure 3:
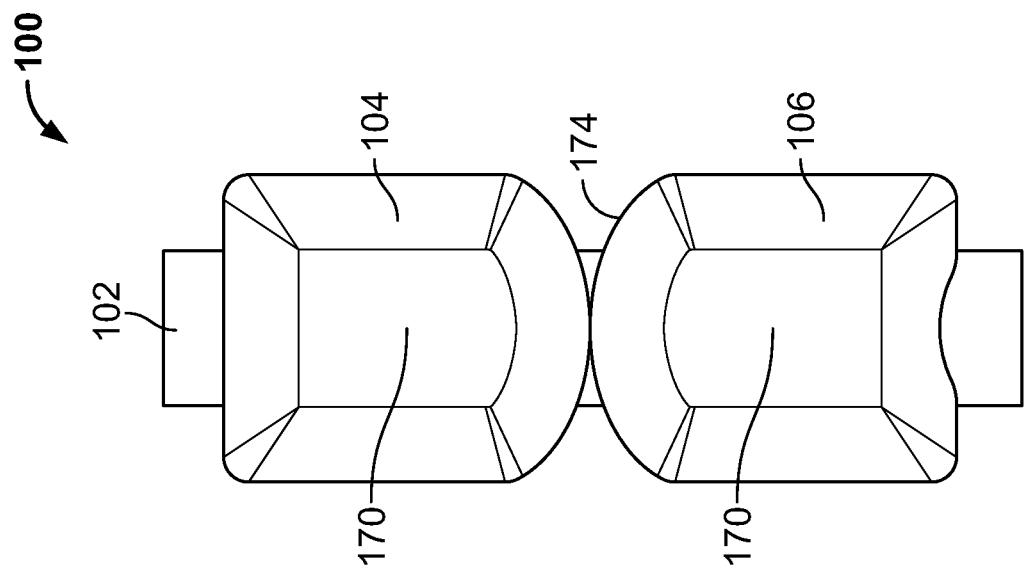
FIG. 3 is a frontal view of the first exemplary occlusion clip of FIG. 1.
Figure 4:
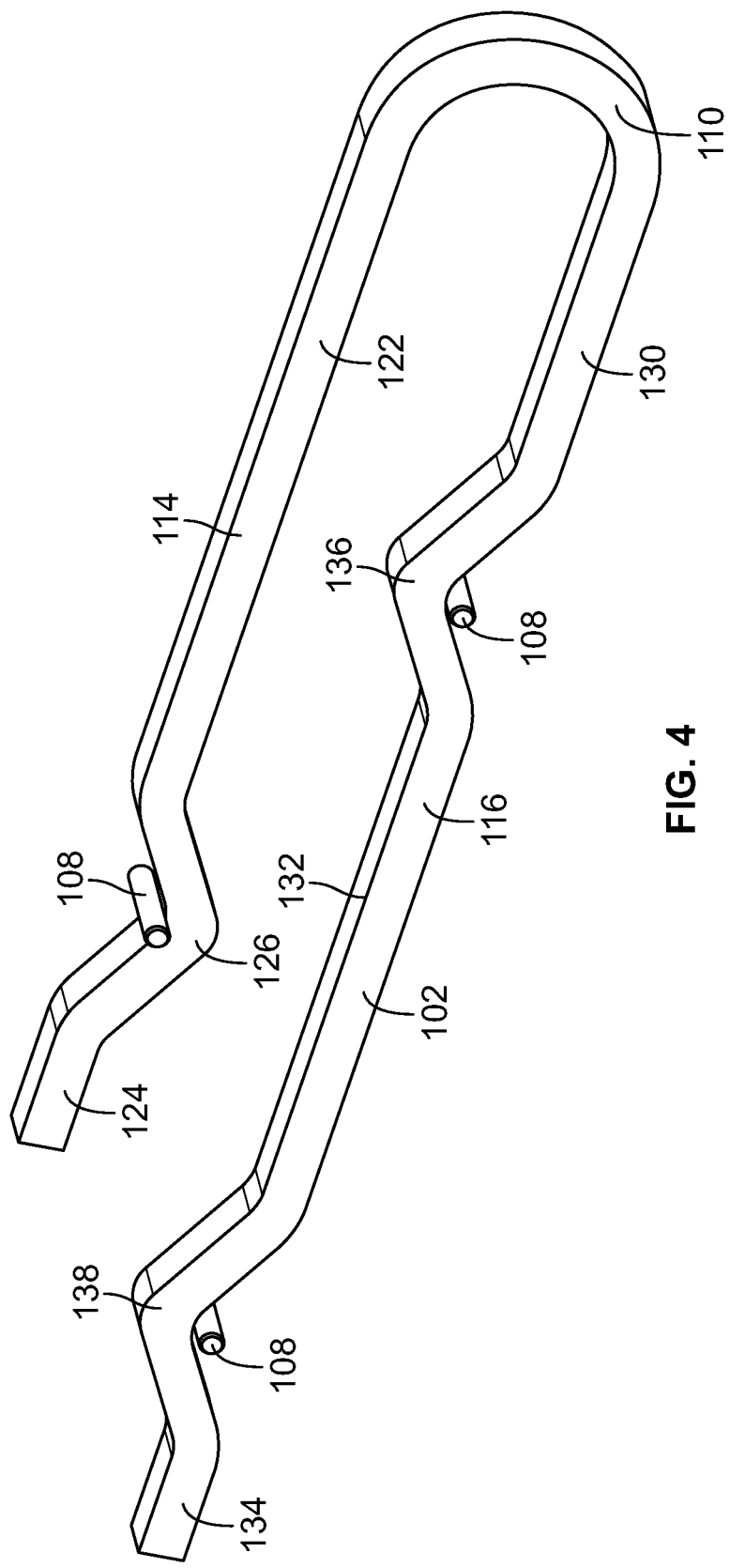
FIG. 4 is an elevated perspective view of the spring and the dowels of the first exemplary occlusion clip of FIG. 1.
Figure 5:
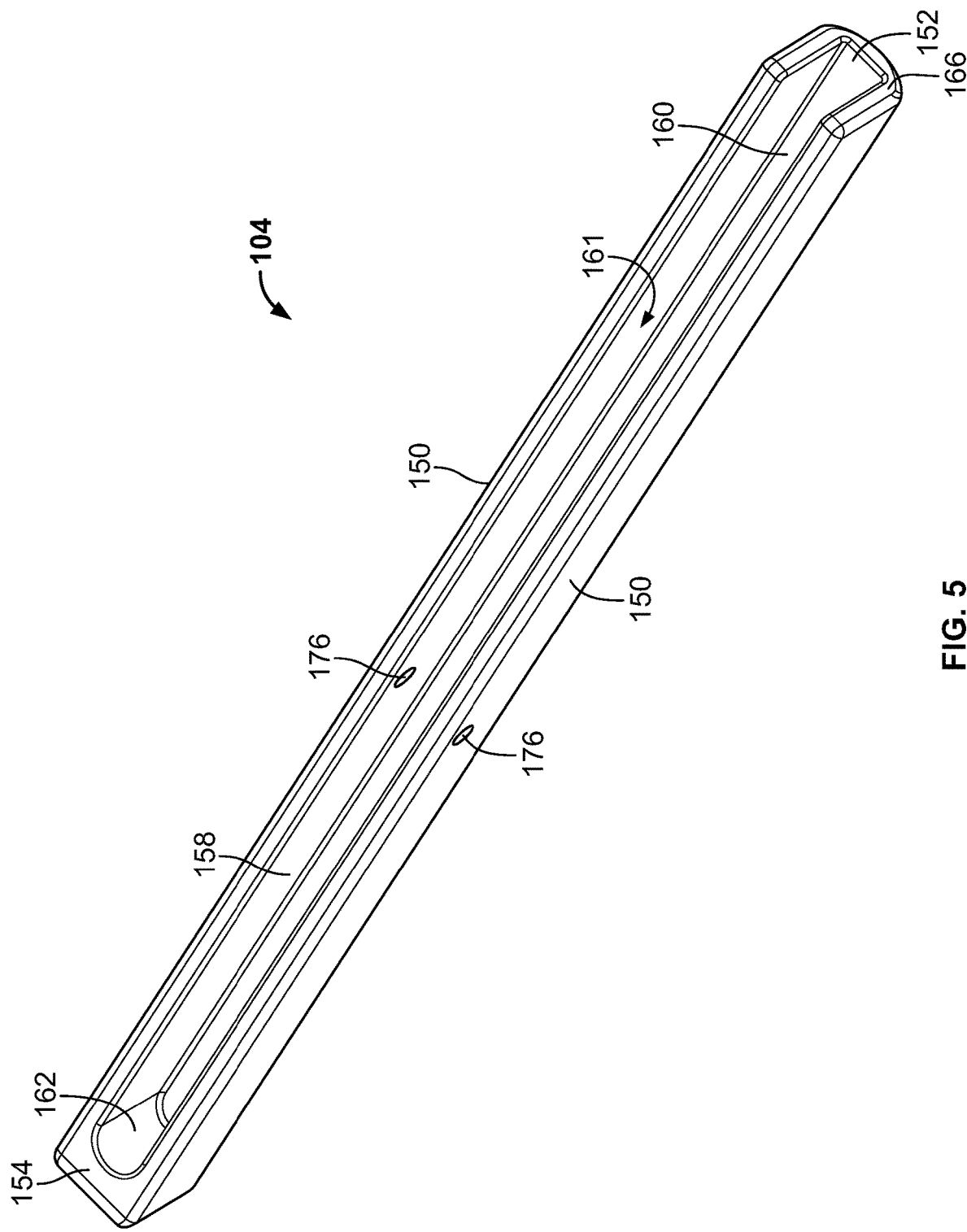
FIG. 5 is an elevated perspective view from the top of a first runner of the first exemplary occlusion clip of FIG. 1.
Figure 6:
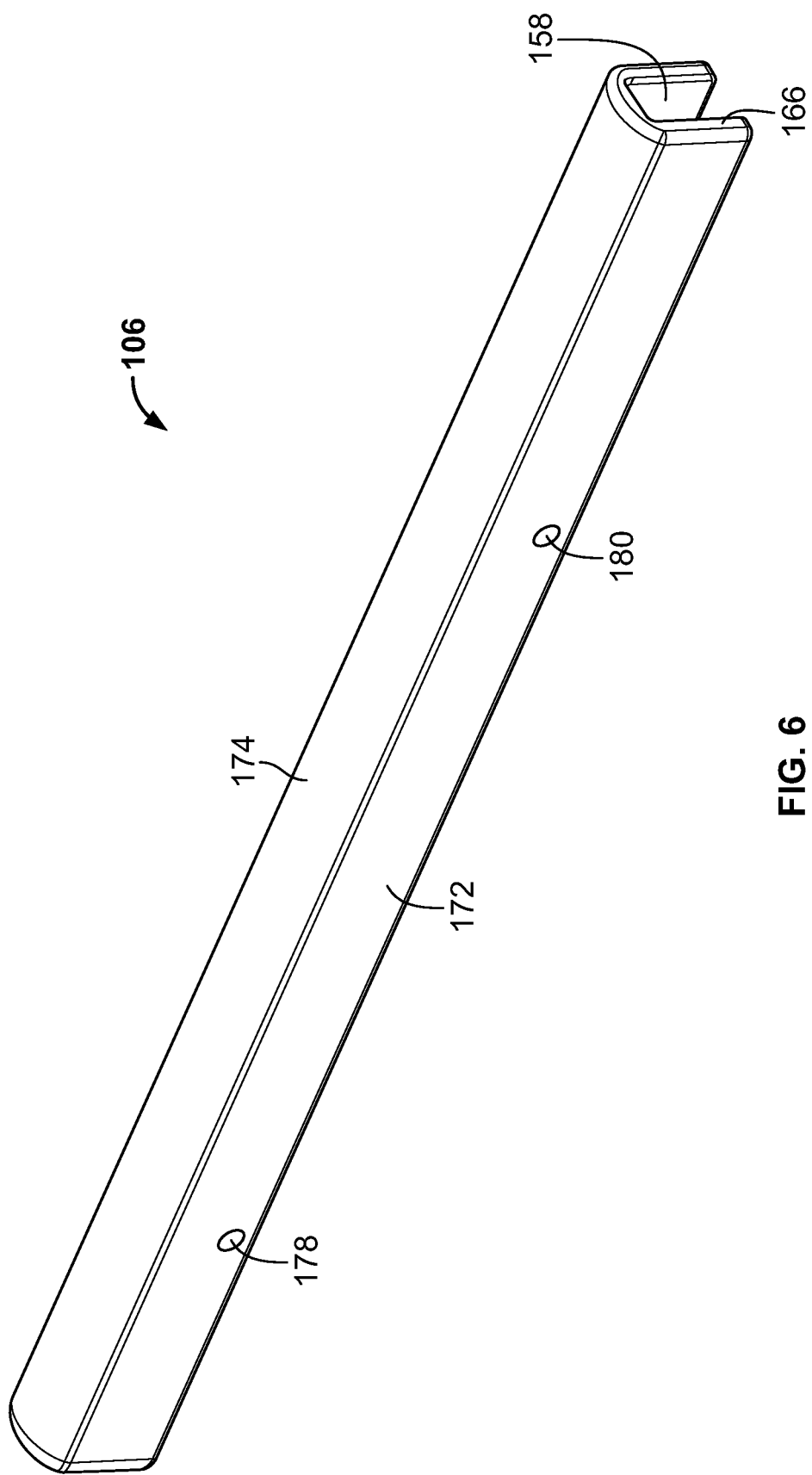
FIG. 6 is an elevated perspective view from the top of a second runner of the first exemplary occlusion clip of FIG. 1.
Figure 7:
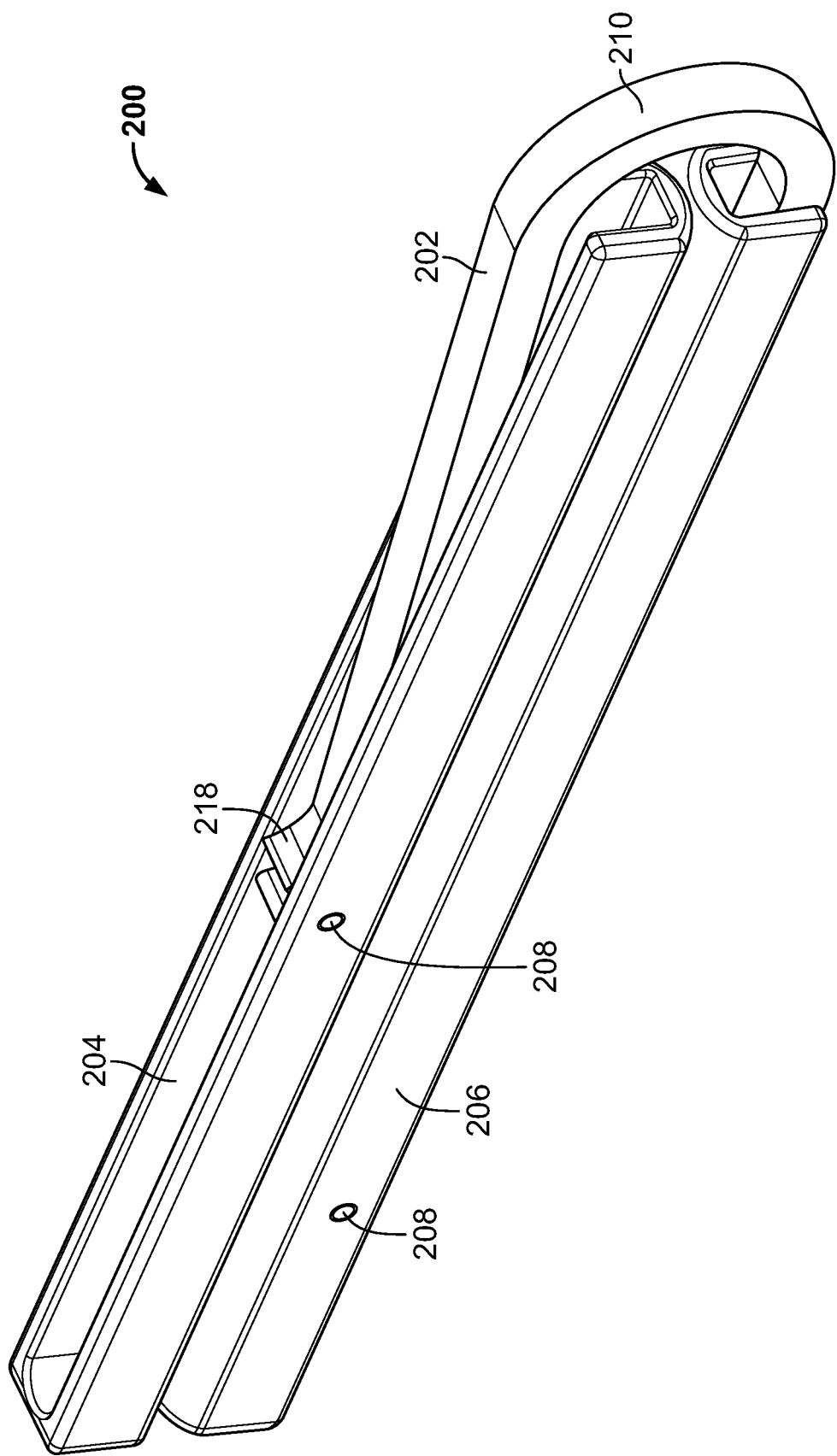
FIG. 7 is an elevated perspective view of a second exemplary occlusion clip in accordance with the present disclosure.
Figure 8:
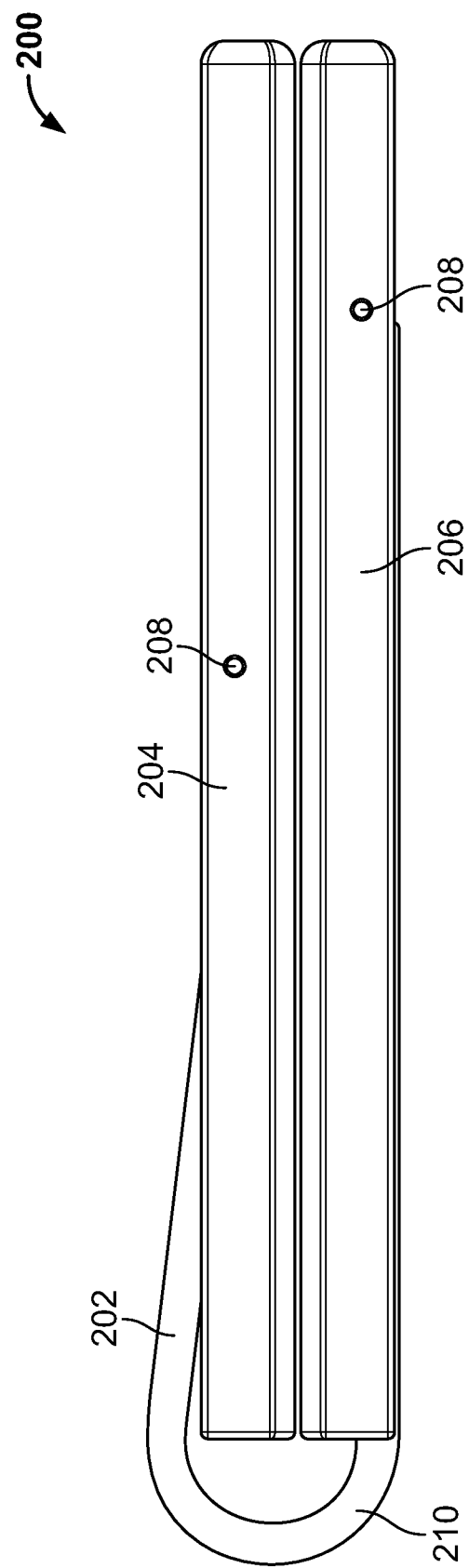
FIG. 8 is a right profile view of the second exemplary occlusion clip of FIG. 7.
Figure 9:
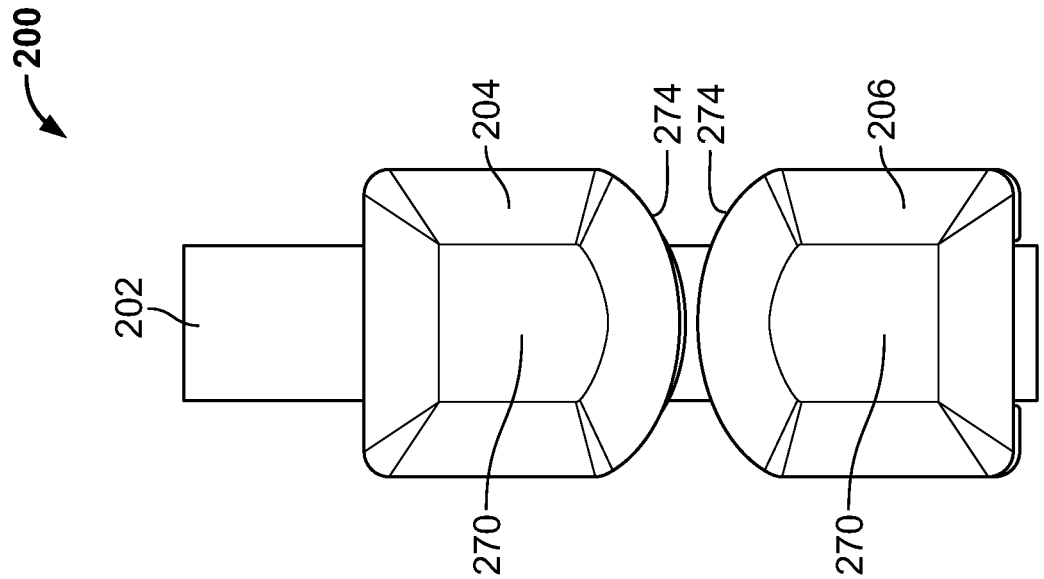
FIG. 9 is a frontal view of the second exemplary occlusion clip of FIG. 7.
Figure 10:
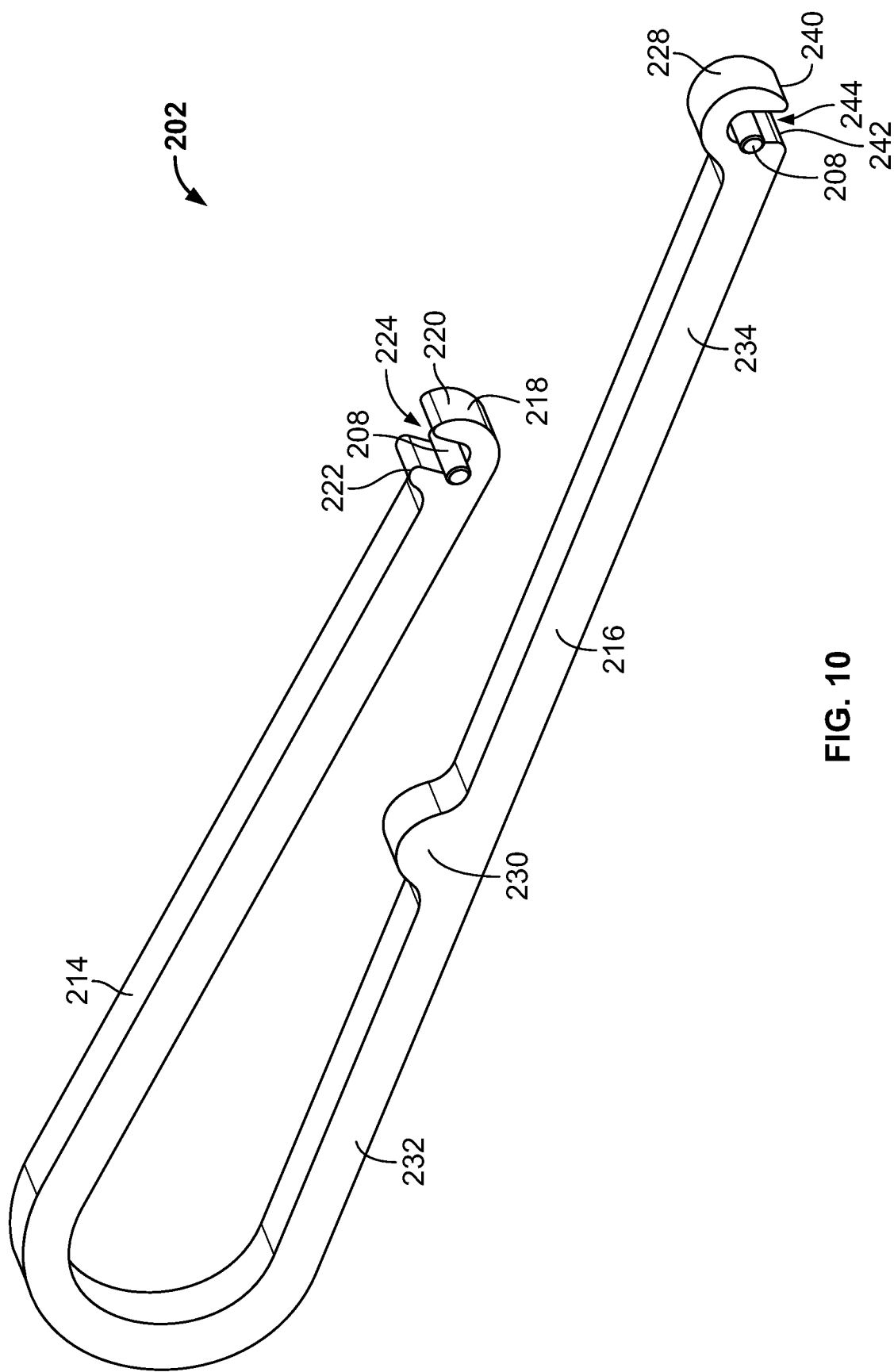
FIG. 10 is an elevated perspective view of the spring and the dowels of the second exemplary occlusion clip of FIG. 7.
Figure 11:
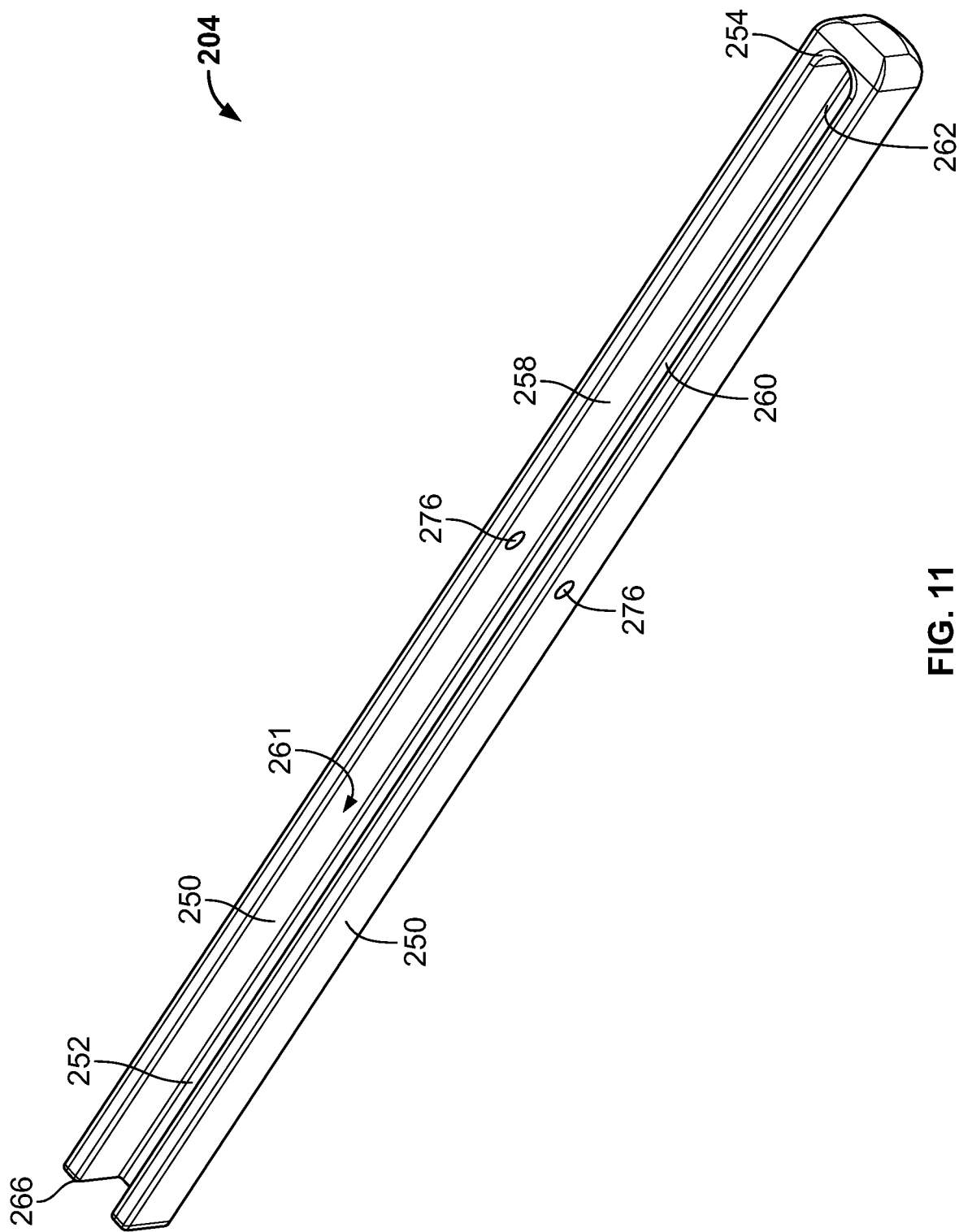
FIG. 11 is an elevated perspective view from the top of a first runner of the second exemplary occlusion clip of FIG. 7.
Figure 12:
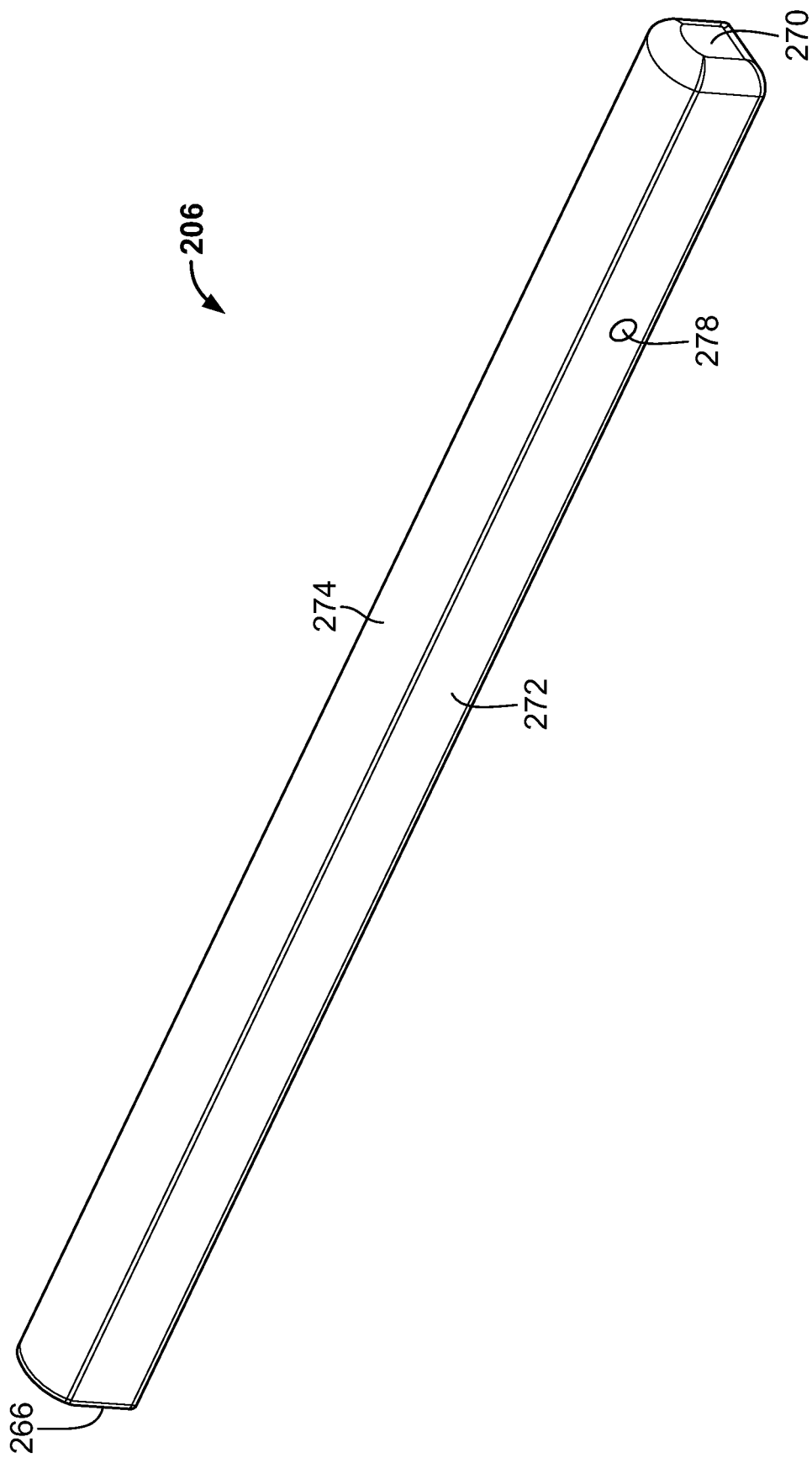
FIG. 12 is an elevated perspective view from the top of a second runner of the second exemplary occlusion clip of FIG. 7.
Figure 13:
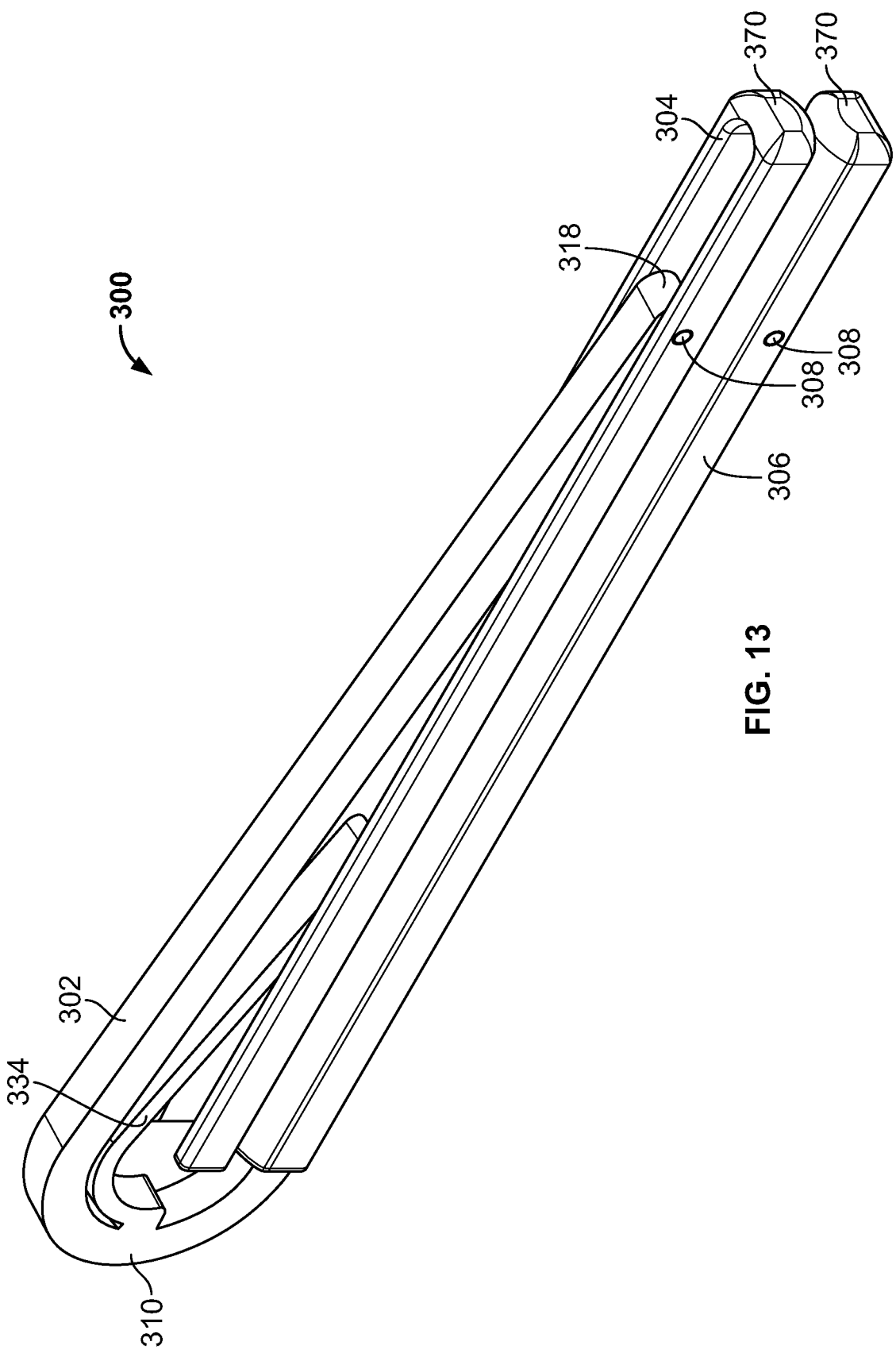
FIG. 13 is an elevated perspective view of a third exemplary occlusion clip in accordance with the present disclosure.
Figure 14:
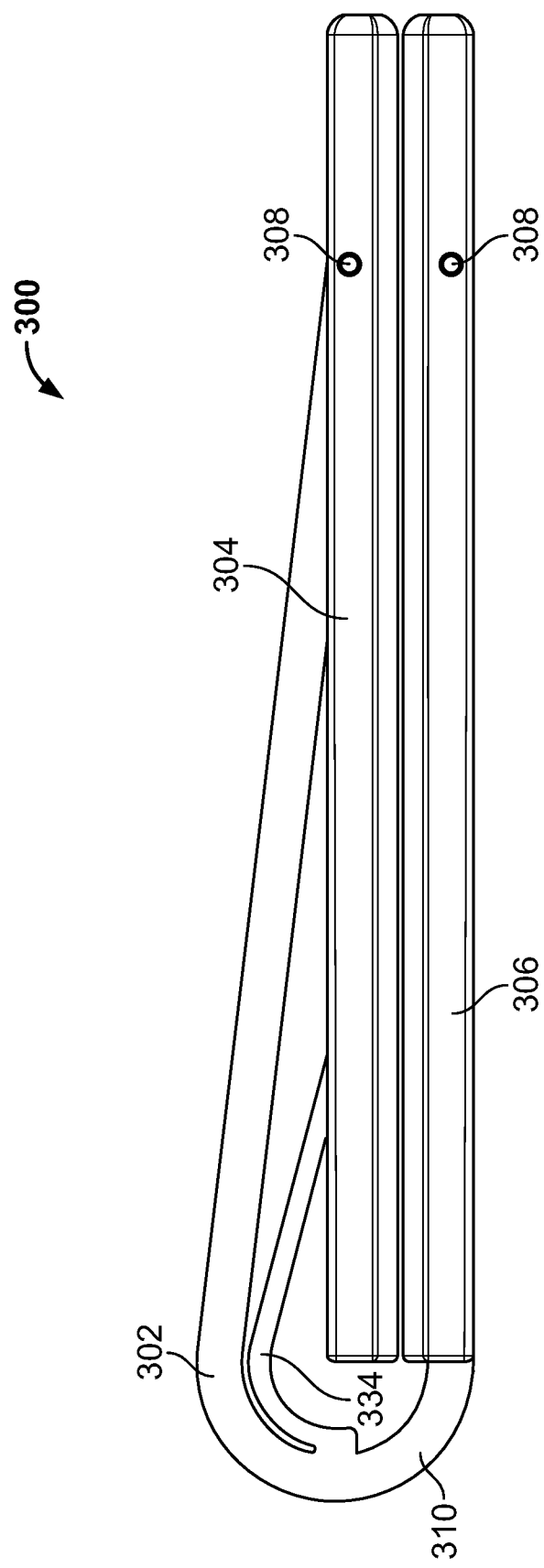
FIG. 14 is a right profile view of the third exemplary occlusion clip of FIG. 13.
Figure 15:
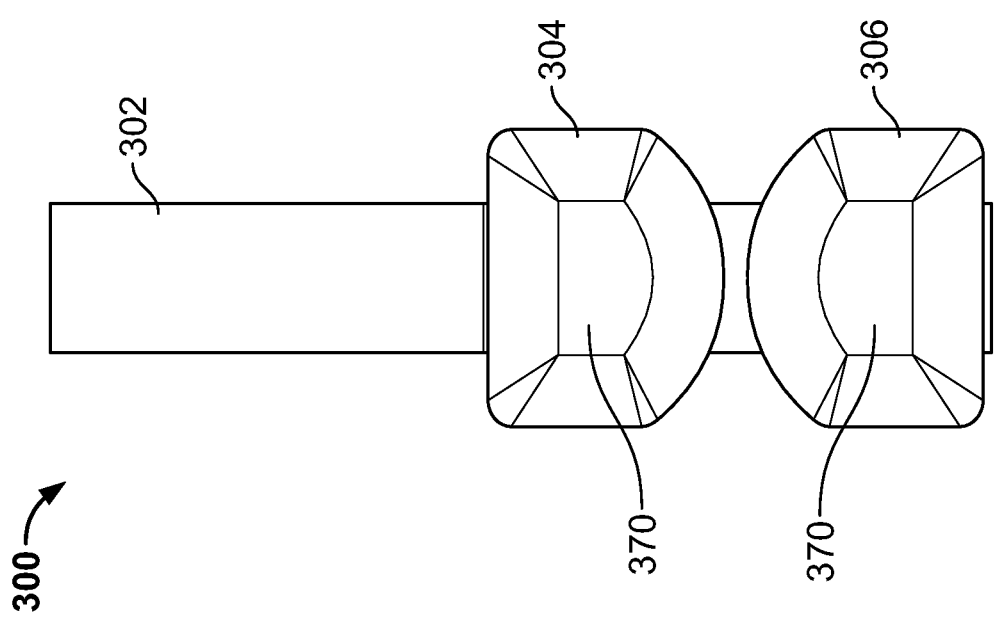
FIG. 15 is a frontal view of the third exemplary occlusion clip of FIG. 13.
Figure 16:
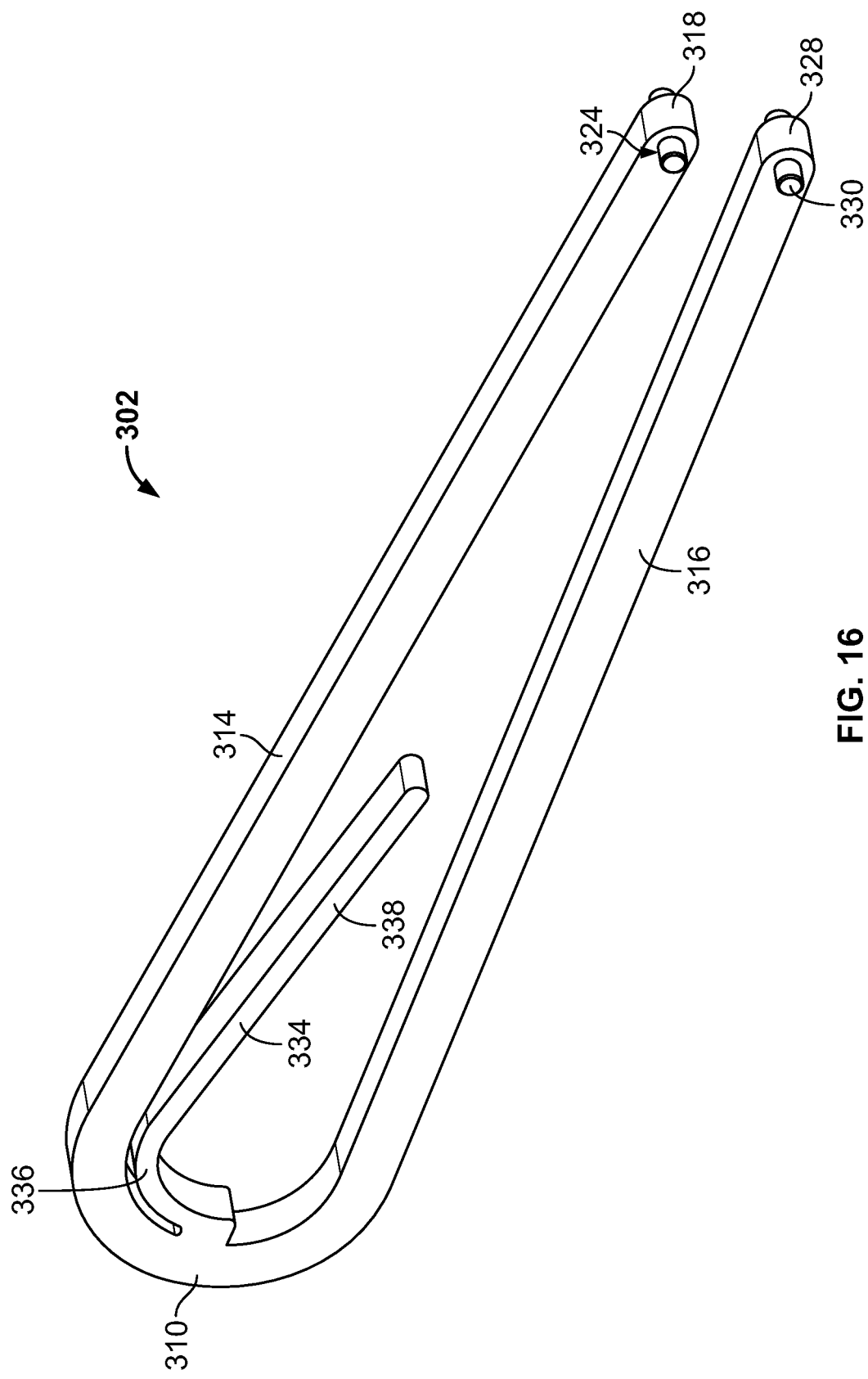
FIG. 16 is an elevated perspective view of the spring and the dowels of the third exemplary occlusion clip of FIG. 13.
Figure 17:
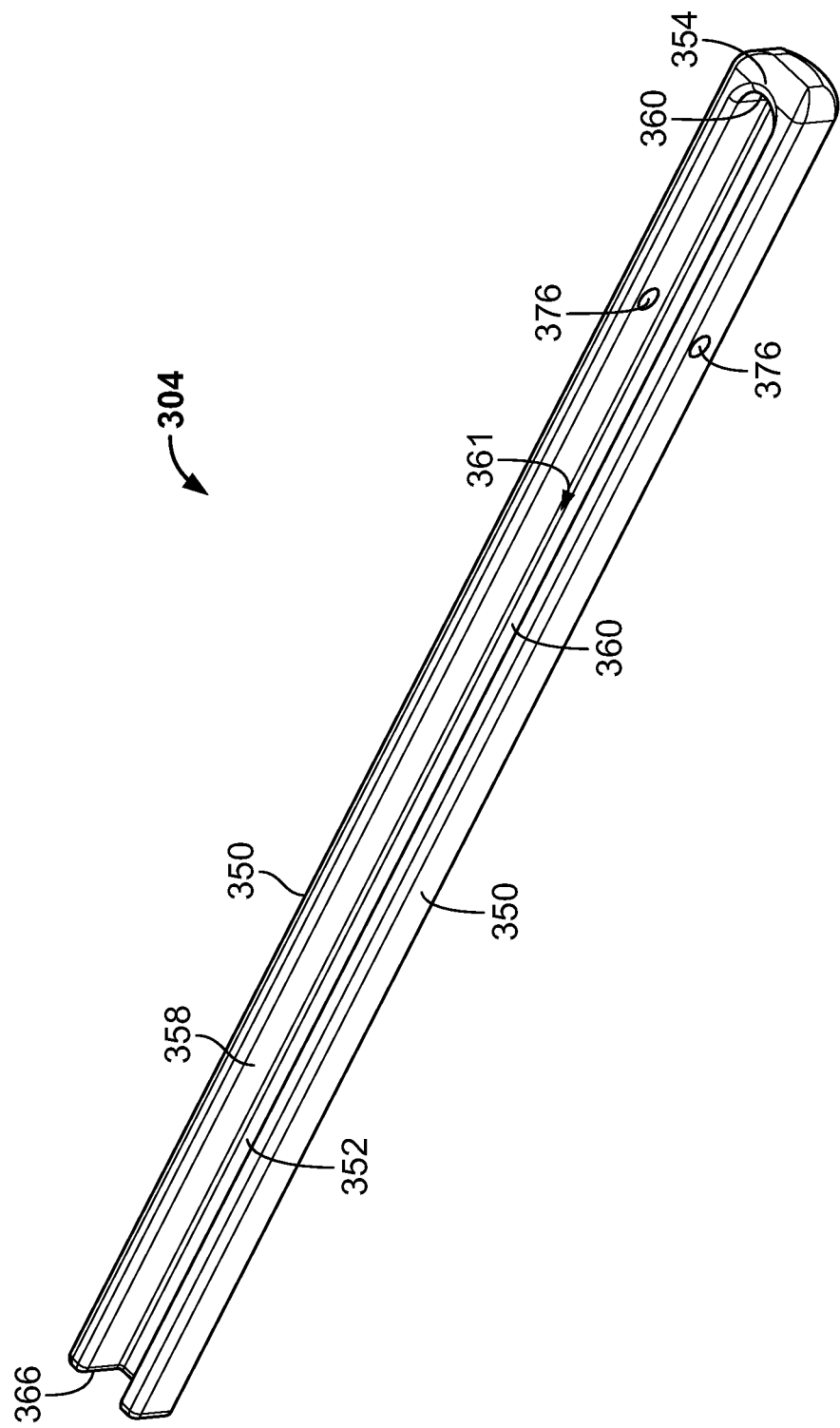
FIG. 17 is an elevated perspective view from the top of a first runner of the third exemplary occlusion clip of FIG. 13.
Figure 18:
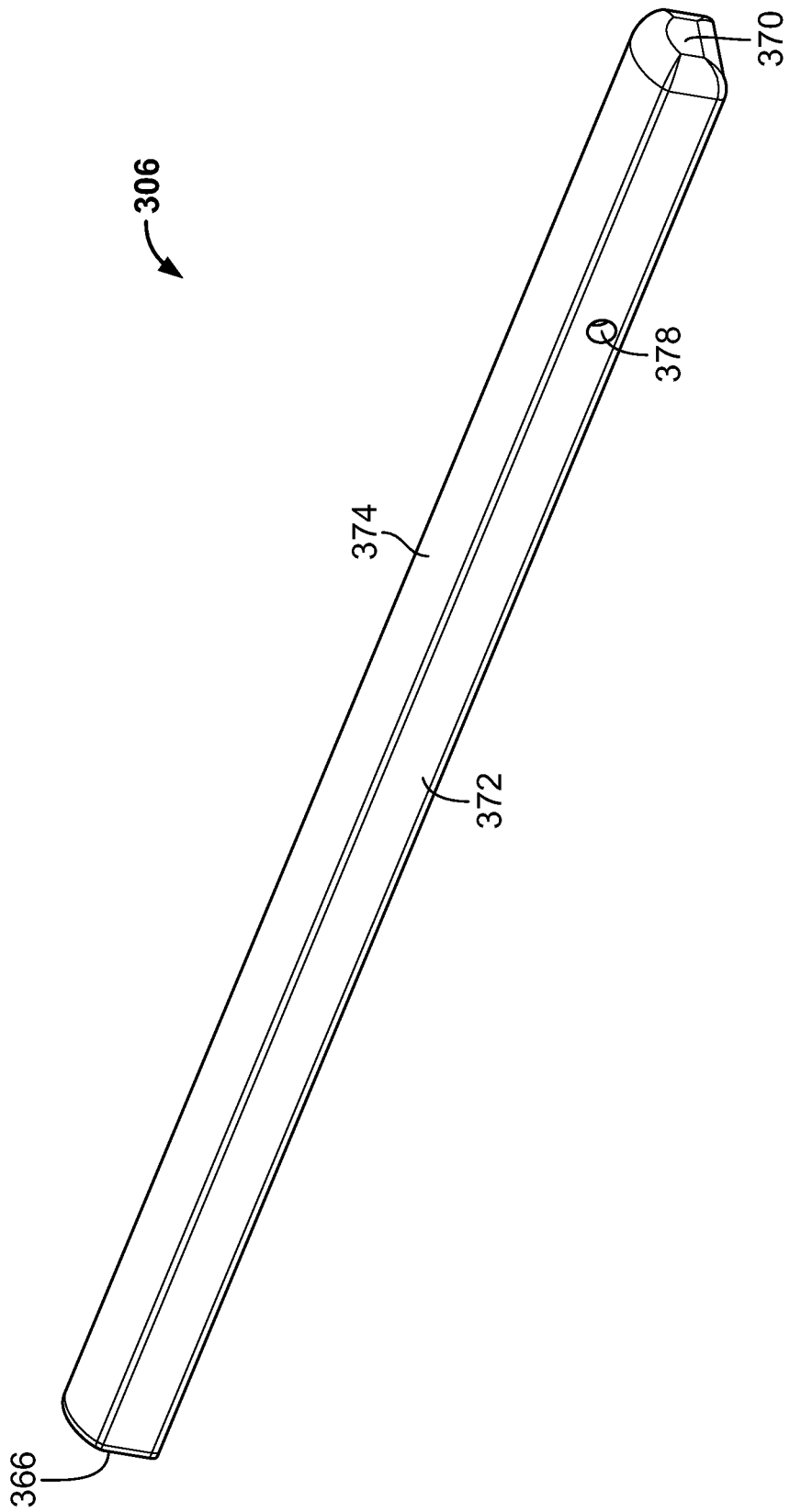
FIG. 18 is an elevated perspective view from the top of a second runner of the third exemplary occlusion clip of FIG. 13.
Figure 19:
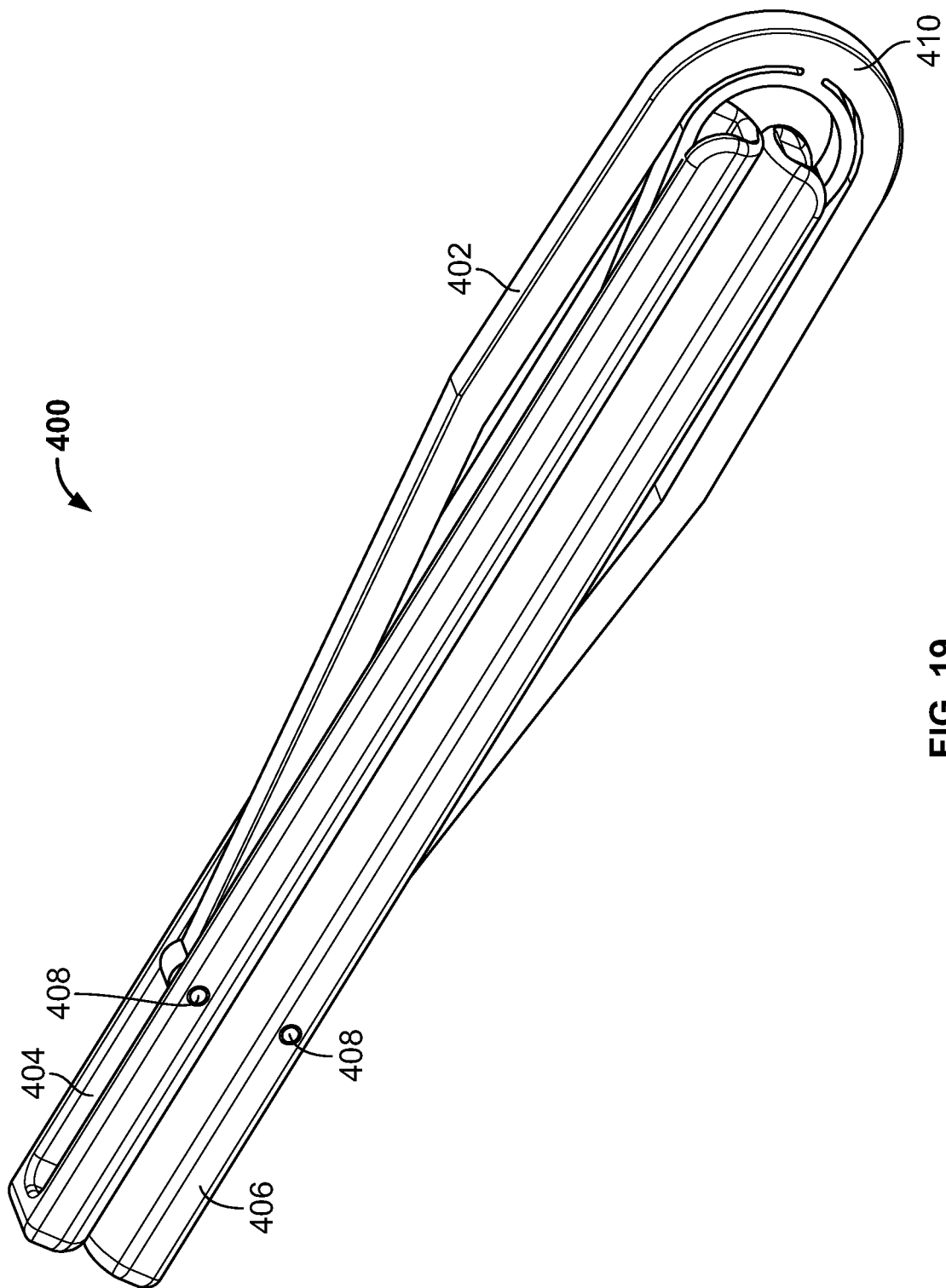
FIG. 19 is an elevated perspective view of a fourth exemplary occlusion clip in accordance with the present disclosure.
Figure 20:
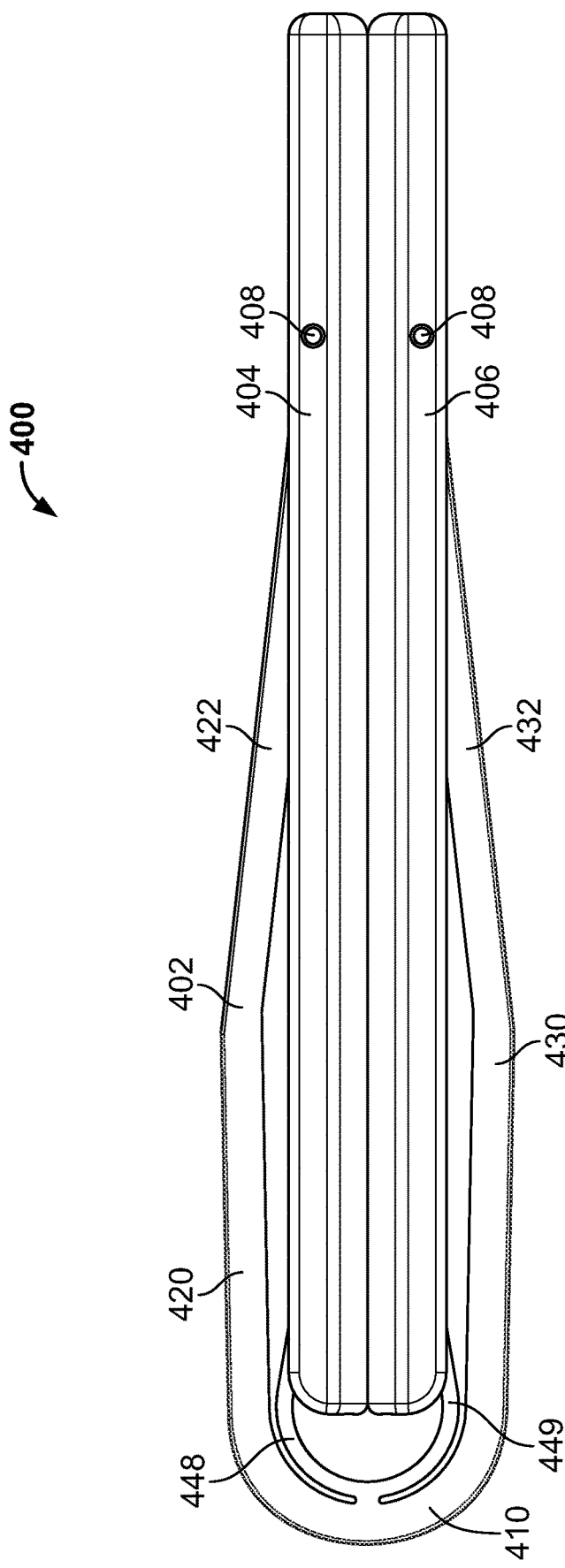
FIG. 20 is a right profile view of the fourth exemplary occlusion clip of FIG. 19.
Figure 21:
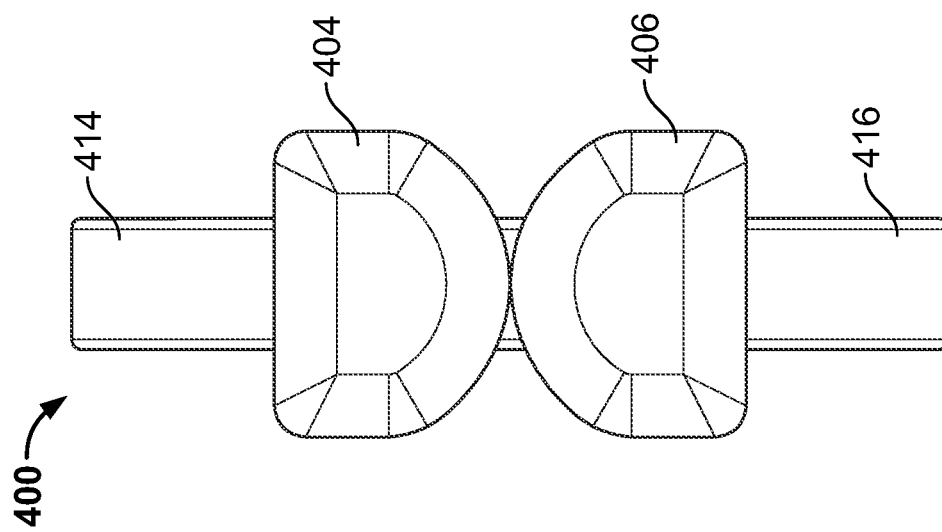
FIG. 21 is a frontal view of the fourth exemplary occlusion clip of FIG. 19.
Figure 22:
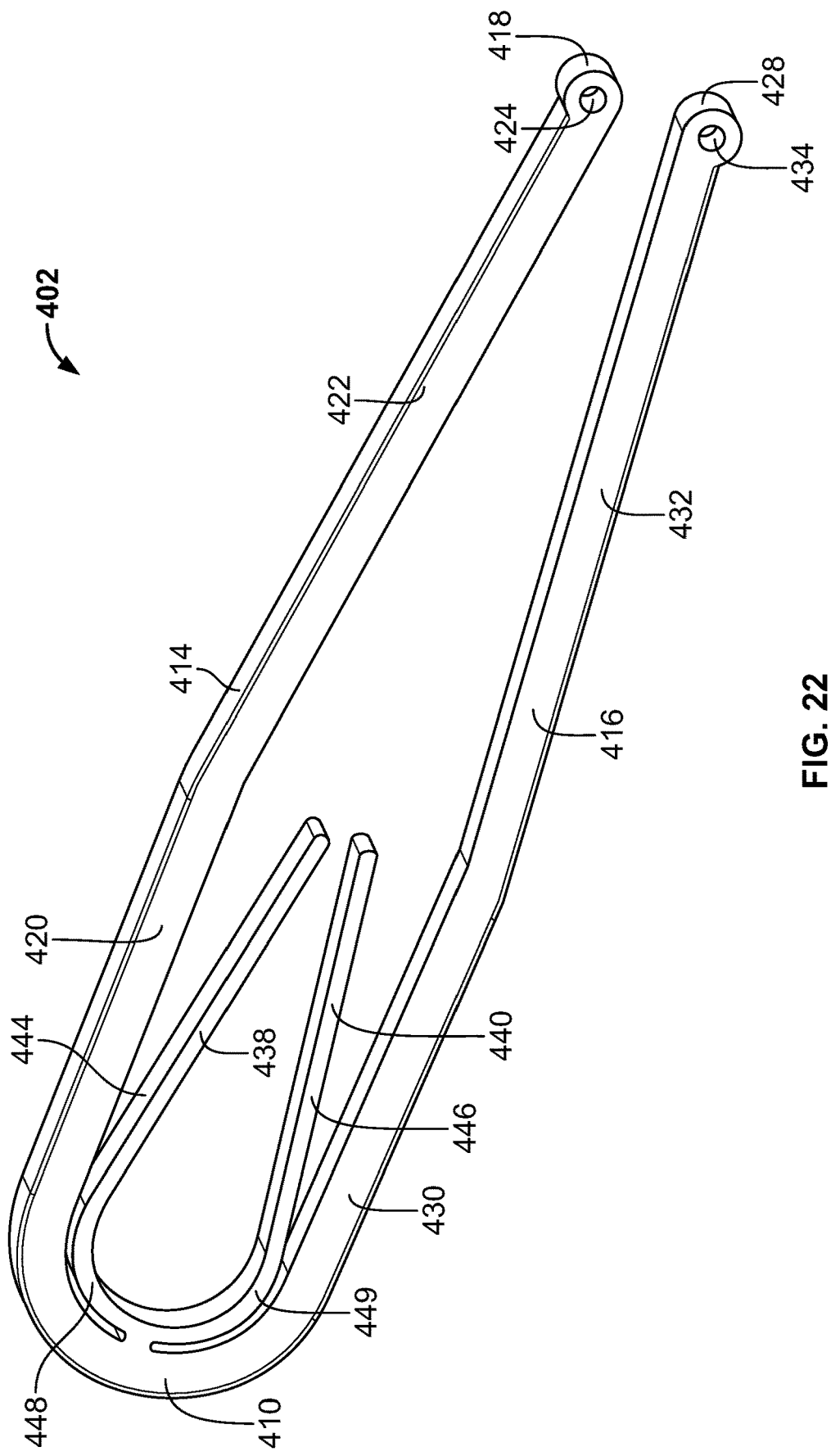
FIG. 22 is an elevated perspective view of the spring of the fourth exemplary occlusion clip of FIG. 19.
Figure 23:
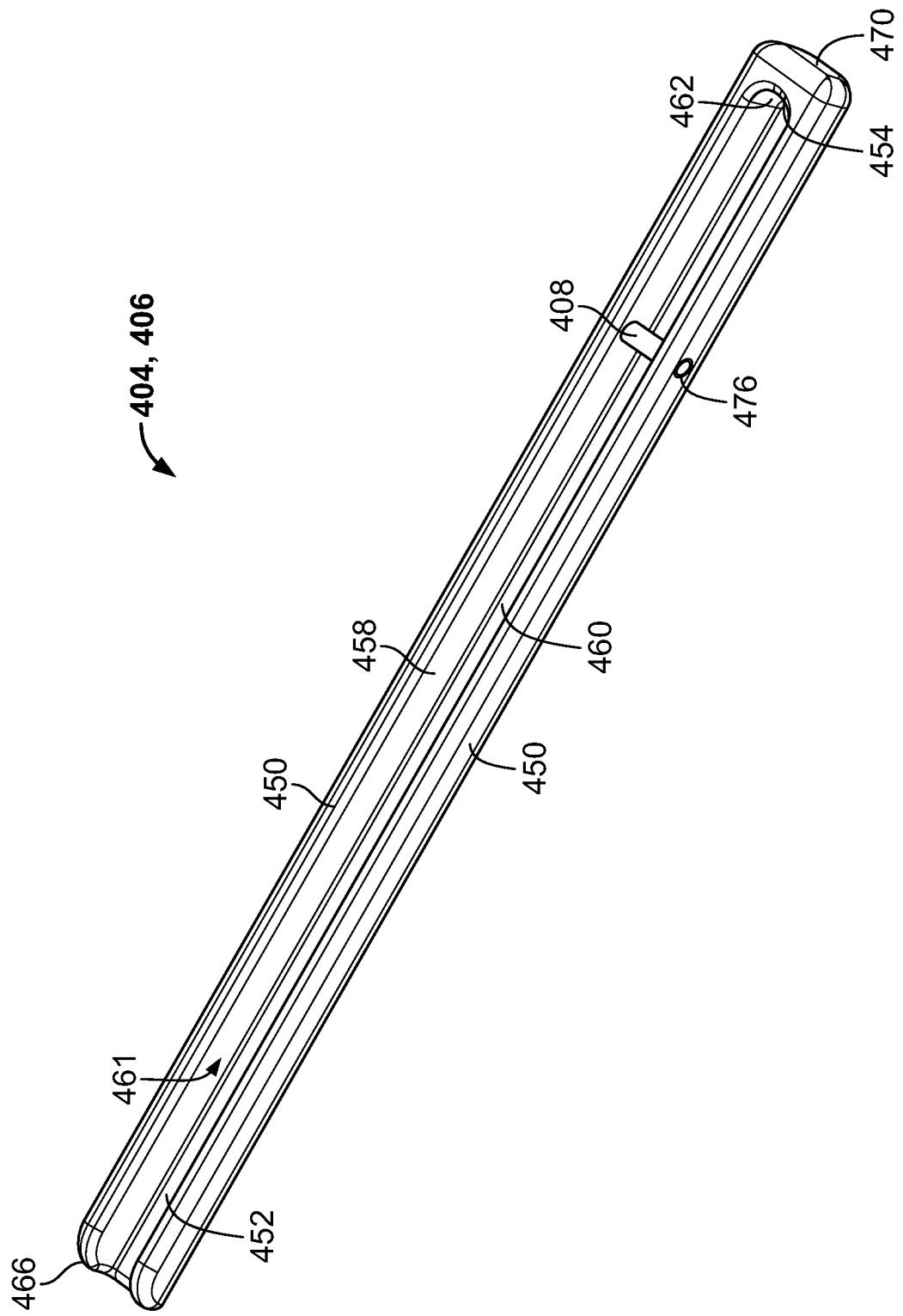
FIG. 23 is an elevated perspective view from the top of a first runner and dowel of the fourth exemplary occlusion clip of FIG. 19.
Figure 24:
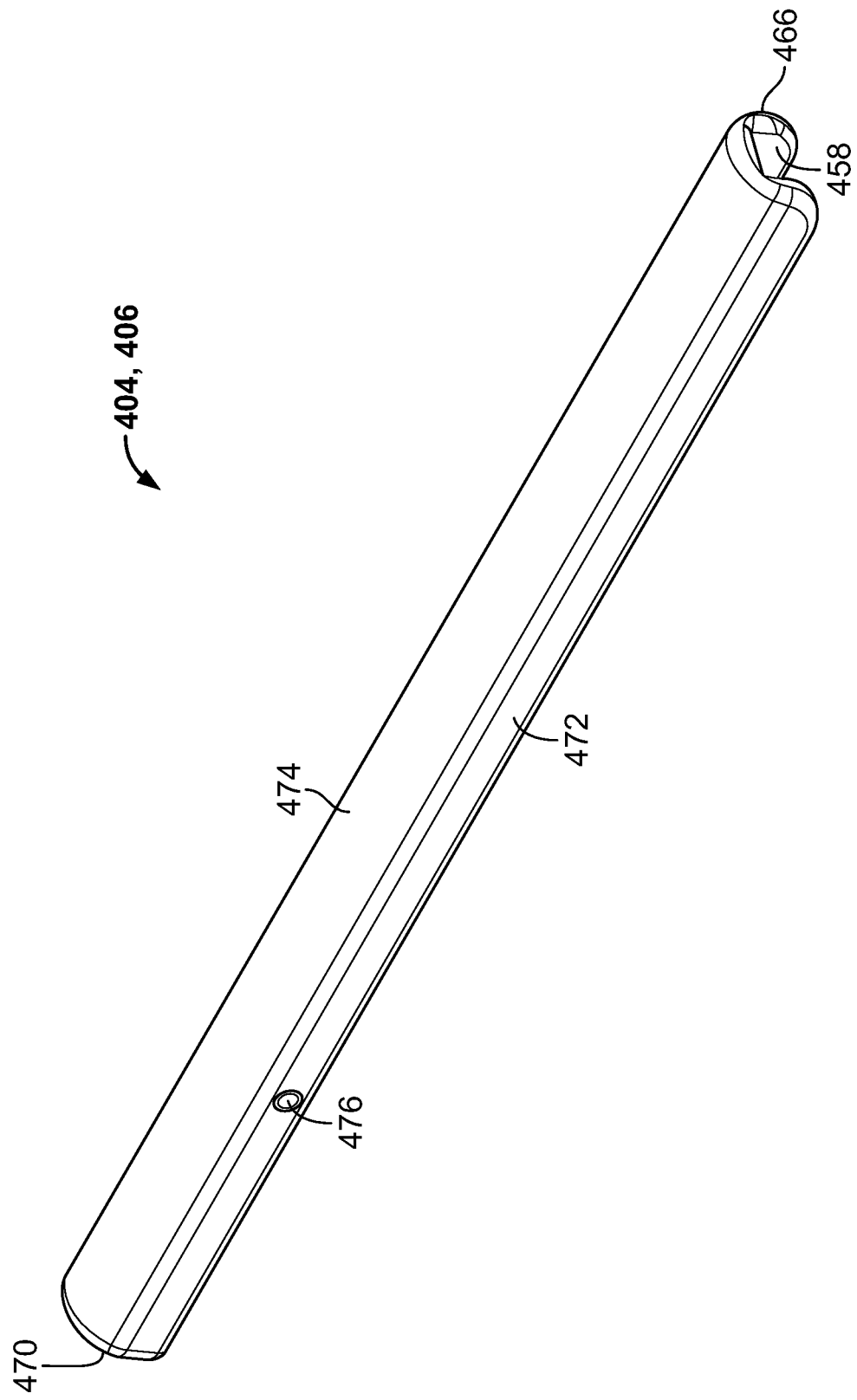
FIG. 24 is an elevated perspective view from the top of a second runner of the fourth exemplary occlusion clip of FIG. 19.
Figure 25:
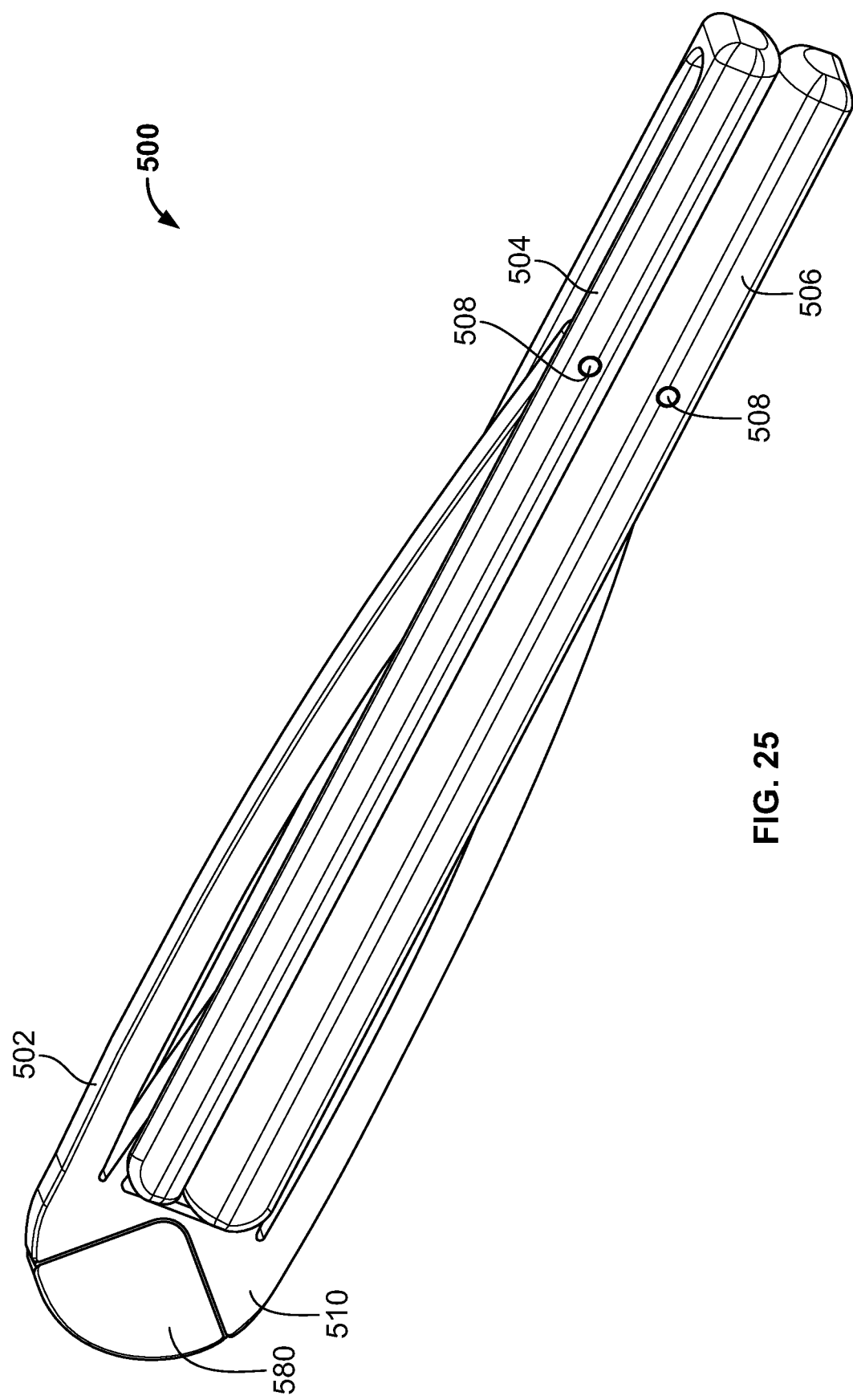
FIG. 25 is an elevated perspective view of a fifth exemplary occlusion clip in accordance with the present disclosure.
Figure 26:
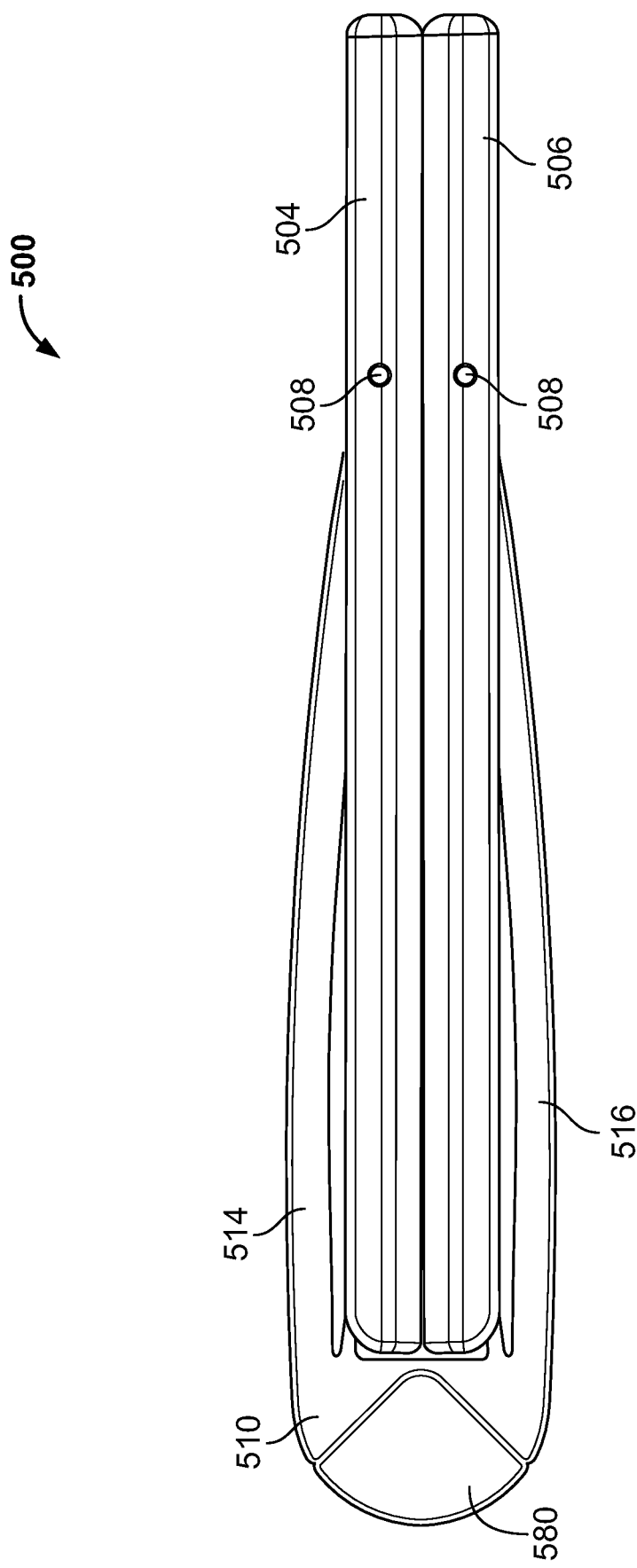
FIG. 26 is a right profile view of the fifth exemplary occlusion clip of FIG. 25.
Figure 27:
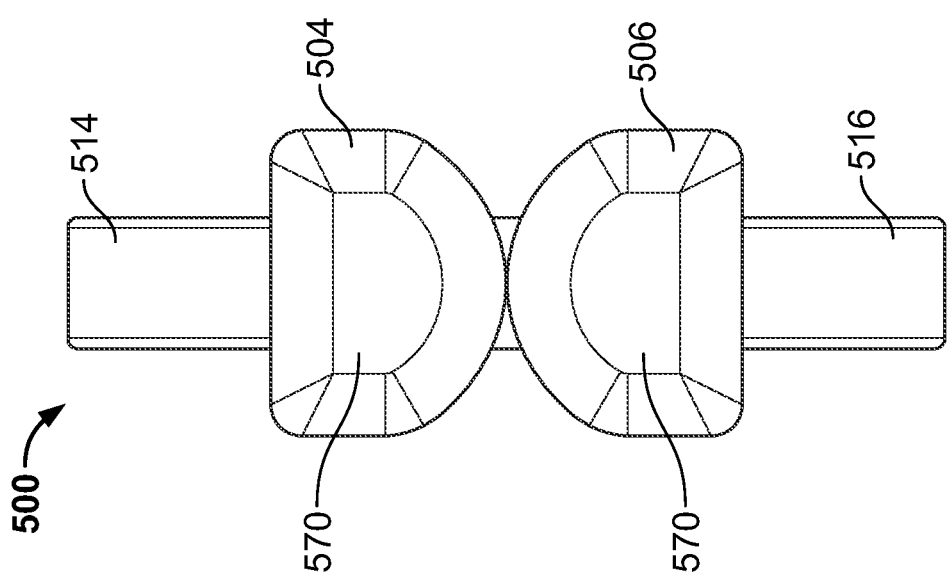
FIG. 27 is a frontal view of the fifth exemplary occlusion clip of FIG. 25.

The exemplary embodiments of the present disclosure are described and illustrated below to encompass devices, methods, and techniques for fabricating and using an occlusion clip. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Referencing FIGS. 1-6, a first exemplary occlusion clip 100 comprises a spring 102 mounted to a first runner 104 and a second runner 106 using a series of dowels 108. The spring 102 includes a U-shaped end 110 from which extends a first arm 114 and a second arm 116. The first arm 114 is mounted to the first runner 104 using a single dowel 108, whereas the second arm 116 is mounted to the second runner 106 using a pair of dowels 108. In this exemplary embodiment, the first arm 114 may be rectangular or circular in cross-section and a pair of linear segments 122, 124 that are interposed by a retention segment 126 that is V-shaped in exemplary form. The first linear segment 122 extends from the U-shaped end 110 and is many multiples in longitudinal length of the second linear segment 124. In exemplary form, the end of the first arm 114 is denoted by the blunt end of the second linear segment 124. Similarly, the second arm 116 also includes a rectangular cross-section and includes first, second, and third linear segments 130, 132, 134. In this exemplary embodiment, the second linear segment 132 is longer than either the first or third linear segments 130, 134. The total longitudinal length of the second arm 116 is greater than that of the first arm 114, with the longitudinal end of the second arm 116 denoted by the blunt rectangular end of the third linear segment 134. Interposing the linear segments 130, 132, 134 are two retention segments 136, 138 embodying an exemplary V-shaped configuration.

In this exemplary embodiment, the first retention segment 126 longitudinally interposes the second and third retention segments 136, 138 while maintaining a vertically spaced apart orientation. More specifically, the first retention segment 126 is vertically oriented in the opposite direction than are the second and third retention segments 136, 138. This results in the apex of the V-shaped profile of the first retention segments 126 facing vertically toward the apexes of the V-shaped profiles of the second and third retention segments 136, 138. The depth of the V-shaped profile and the separation of the arms 114, 116 and linear segment 130 can serve to increase or decrease the spring force bias at the closed position of the occluding clip. Each of the retention segments 126, 136, 138 provides a contact area with a respective runner 104, 106.

The first and second runners 104, 106 have essentially the same shape. Specifically, both runners 104, 106 include a pair of parallel side-walls 150, a longitudinal wall 152, and an end wall 154 that is concurrently mounted to the foregoing walls. The longitudinal wall 152 interposes and joins the parallel walls 150. In exemplary form, the interior surfaces 158 of the parallel walls 150 are planar and parallel to one another. These planar surfaces 158 cooperate with a planar interior surface 160 of the longitudinal wall 152 to delineate a block U-shaped longitudinal cavity 161 where the planar surfaces of the parallel walls are perpendicular to the planar surface of the longitudinal wall. In addition, the end wall 154 interposes and joins the parallel walls 150 to provide a longitudinal end cap. An interior surface 162 of the end wall is arcuately shaped and cooperates with the planar surfaces 158 of the parallel walls 150 to delineate a rounded U-shaped vertical cavity. In sum, the longitudinal end 166 of the runners 104, 106 opposite the end wall 154 is open, as is the vertical end opposite the planar interior surface 160 of the longitudinal wall 152.

The exterior of each runner 104, 106 includes a blunt end 170 that is rounded over at its periphery to join opposing longitudinal planar surfaces 172 and an arcuate longitudinal surface 174. The longitudinal arcuate surfaces 174 are adapted to be the element of each runner 104, 106 that is closest to one another and interposed by tissue when in a tissue occluding position.

As introduced previously, the first runner 104 is mounted to the spring 102 using a dowel 108, whereas the second runner 106 is mounted to the spring using a pair of dowels. Consequently, the first runner 104 includes a pair of openings 176 that extend through the parallel walls 150 and are coaxial with one another. In this exemplary embodiment, the openings 176 are cylindrical and arranged approximately in the longitudinal middle of the first runner 104. In contrast, the second runner 106 includes two pair of openings 178, 180 that extend through the parallel walls 150 and are coaxial with one another. In this exemplary embodiment, the openings 178, 180 are cylindrical and the first pair of openings 178 occurs at approximately one-third the longitudinal length, whereas the second pair of openings 180 occurs at approximately two-thirds the longitudinal length of the second runner 106.

Assembly of the first exemplary occlusion clip 100 includes longitudinally sliding the runners 104, 106 with respect to the spring 102 when no dowels 108 are present. By way of example, the first runner 104 is oriented in parallel with the first arm 114 so that the open end of the first runner 104 is longitudinally aligned to receive the retention segment 126. Thereafter, the first runner 104 is repositioned with respect to the first arm 114 so that the retention segment 126 is longitudinally repositioned within the U-shaped cavity 161 until the retention segment 126 is aligned with the pair of openings 176. Thereafter, the dowel 108 is inserted through the pair of openings 176 so that the dowel and the planar interior surface 160 of the longitudinal wall 152 sandwich the retention segment 126. After the dowel 108 is in position, the first runner 104 may not be longitudinally, vertically, or rotationally repositioned with respect to the first arm 114. Mounting of the second runner 106 to the second arm 116 follows a similar process.

Mounting the second runner 106 to the second arm 116 may include longitudinally sliding the second runner 106 with respect to the spring 102 when no dowels 108 extend through the second runner. For example, the second runner 106 is oriented in parallel with the second arm 116 so that the open end 166 of the first runner 106 is longitudinally aligned to receive the retention segments 136, 138. Thereafter, the second runner 106 is repositioned with respect to the second arm 116 so that the retention segments 136, 138 are longitudinally repositioned within the U-shaped cavity 161 until the retention segments 136, 138 are aligned with respective pairs of openings 178, 180. Thereafter, two dowels 108 are inserted through the two pair of openings 178, 180 so that the dowels and the planar interior surface 160 of the longitudinal wall 152 sandwich the retention segments 136, 138. After the dowels 108 are in position, the second runner 106 may not be longitudinally, vertically, or rotationally repositioned with respect to the second arm 116.

In operation, the spring 102 operates to bias the runners 104, 106 toward one another to exert an occlusion pressure upon tissue captured therebetween. To achieve this bias, the spring 102 may be cast, cut, or fabricated in the shape shown in FIG. 4. Thereafter, repositioning the first arm 114 away from the second arm 116 requires overcoming the bias of the spring 102, including the bias attributed to the U-shaped end 110 and the bias attributed to the arms 114, 116 and the linear segment 130. When no active force is exerted upon the arms 114, 116, the arms will default to the position shown in FIG. 2. Consequently, when positioning the clip 100 to occlude bodily tissue, such as a left atrial appendage, the clip 100 is forced open so that the ends of the arms 114, 116 are forced farther away from one another to create a vertical gap between the runners 104, 106. This vertical gap is wide enough to allow bodily tissue to interpose the runners 104, 106 and, when the active force is no longer exerted upon the arms 114, 116, the bias of the spring 102 is operative to force the runners toward one another and discontinue circulation across the tissue interposing the runners. Eventually, the absence of circulation to one side of the clamped tissue leads to atrophy and occlusion of the bodily tissue in question.

Occlusion of the bodily tissue is accomplished through transferal of the forces imparted by the spring 102 through the runners 104, 106 and transmitted to the tissue as a pressure profile. The presence of proximal and distal spring bias allows the occlusion clip runners 104, 106 to balance the force independently at the proximal and distal ends, allowing for non-uniform shapes of tissue to be evenly compressed between the runners. The desired pressure can be obtained through adjustment of both the spring force and the runner 104, 106 shape and size. The spring force is a function of the shape, thickness, and width of the spring 102 material and each can be independently adjusted to obtain the desired force at the desired separation. Additionally, it is desired that as the tissue atrophies, a significant force continues to be applied even as the runners 104, 106 compress the tissue between them to near zero or zero thickness. This "zero offset force" can be adjusted through design of the shape of the spring 102 causing the "free state" of the contact points of the spring to the runners 104, 106 to become closer together or to even offset in the negative direction. It will be understood by those with ordinary skill in the art that this offset may be designed into the spring 102 or may be introduced through intentional plastic deformation of the spring.

Referencing FIGS. 7-12, a second exemplary occlusion clip 200 comprises a spring 202 mounted to a first runner 204 and a second runner 206 using a pair of dowels 208. The spring 202 includes a U-shaped end 210 from which extends a first arm 214 and a second arm 216. The first arm 214 is mounted to the first runner 204 using a first dowel 208, whereas the second arm 216 is mounted to the second runner 206 using a second dowel 208. In this exemplary embodiment, the first arm 214 has a rectangular, linear cross-section except for a distal end 218. The distal end 218 is rounded over and includes spaced apart projections 220, 222 that delineate a channel 224 configured to receive a dowel 208. In this exemplary embodiment, the channel 224 faces away from the second arm 216.

Similarly, the second arm 216 also has a rectangular, linear or circular cross-section except for a distal end 228 and a rounded hump 230 extending toward the first arm 214. In this exemplary embodiment, the second arm 216 includes a first linear segment 232 and a second linear segment 234 that are interposed by the hump 230. Though not required, the longitudinal length of the second linear segment 234 is greater than that of the first linear segment 232.

In this exemplary embodiment, the distal end 228 is rounded over and includes spaced apart projections 240, 242 that delineate a channel 244 configured to receive a dowel 208. In exemplary form, the channel 244 faces away from the first arm 214. It should also be noted that the rounded vertical height of the distal end 228 is approximately equal to the vertical height of the rounded hump 230. Both the rounded hump 230 and rounded distal end 228 of the second arm 216 provide respective contact areas for the second runner 206.

The first and second runners 204, 206 have essentially the same shape. Specifically, both runners 204, 206 include a pair of parallel walls 250, a longitudinal wall 252, and an end wall 254 that is concurrently mounted to the foregoing walls. The longitudinal wall 252 interposes and joins the parallel walls 250. In exemplary form, the interior surfaces 258 of the parallel walls 250 are planar and parallel to one another. These planar surfaces 258 cooperate with a planar interior surface 260 of the longitudinal wall 252 to delineate a block U-shaped longitudinal cavity 261 where the planar surfaces of the parallel walls are perpendicular to the planar surface of the longitudinal wall. In addition, the end wall 254 interposes and joins the parallel walls 250 to provide a longitudinal end cap. An interior surface 262 of the end wall is arcuately shaped and cooperates with the planar surfaces 258 of the parallel walls 250 to delineate a rounded U-shaped vertical cavity. In sum, the longitudinal end 266 of the runners 204, 206 opposite the end wall 254 is open, as is the vertical end opposite the planar interior surface 260 of the longitudinal wall 252.

The exterior of each runner 204, 206 includes a blunt end 270 that is rounded over at its periphery to join opposing longitudinal planar surfaces 272 and an arcuate longitudinal surface 274. The longitudinal arcuate surfaces 274 are adapted to be the element of each runner 204, 206 that is closest to one another and interposed by tissue when in a tissue occluding position.

As introduced previously, the first and second runners 204, 206 are mounted to the spring 202 using respective dowels 208. Consequently, the first runner 204 includes a pair of openings 276 that extend through the parallel walls 250 and are coaxial with one another. In this exemplary embodiment, the openings 276 are cylindrical and arranged distally just beyond the longitudinal middle of the first runner 204. Likewise, the second runner 206 includes a pair of openings 278 that extend through the parallel walls 250 and are coaxial with one another. In this exemplary embodiment, the openings 278 are cylindrical and the first pair of openings 278 are arranged approximately at eighty percent of the longitudinal length (i.e., nearest the distal end).

Assembly of the second exemplary occlusion clip 200 includes longitudinally sliding the runners 204, 206 with respect to the spring 202 when no dowels 208 are present. By way of example, the first runner 204 is oriented to be slightly angled with respect to the first arm 214 so that the open end of the first runner 204 is longitudinally aligned to receive the rounded distal end 218. Thereafter, the first runner 204 is repositioned with respect to the first arm 214 so that the distal end 218 is longitudinally repositioned within the U-shaped cavity 261 until the distal end 218 is aligned with the pair of openings 276. Thereafter, the dowel 208 is inserted through the pair of openings 276 so that the dowel and the planar interior surface 260 of the longitudinal wall 252 sandwich the distal end 218. After the dowel 208 is in position, the first runner 204 may not be longitudinally or vertically repositioned with respect to the first arm 214. But the first runner 204 may be rotationally repositionable with respect to the first arm 214 about an axis coaxial with the longitudinal length of the dowel 208. Mounting of the second runner 206 to the second arm 216 follows a similar process.

Mounting the second runner 206 to the second arm 216 may include longitudinally sliding the runner 206 with respect to the spring 202 when no dowel 208 extends through the second runner. For example, the second runner 206 is oriented in parallel with the second arm 216 so that the open end 266 of the first runner 206 is longitudinally aligned to receive the rounded distal end 228. Thereafter, the second runner 206 is repositioned with respect to the second arm 216 so that the rounded distal end 228 is longitudinally repositioned within the U-shaped cavity 261 until the distal end is aligned with the pair of openings 278. Thereafter, the dowel 208 is inserted through the pair of opening 278 so that the dowel and the planar interior surface 260 of the longitudinal wall 252 sandwich the distal end 228. After the dowel 208 is in position, the second runner 206 may not be longitudinally or vertically repositioned with respect to the second arm 216, but may be rotationally repositionable with respect to the second arm 216 about an axis coaxial with the longitudinal length of the dowel 208.

In operation, the spring 202 operates to bias the runners 204, 206 toward one another to exert an occlusion pressure upon tissue captured therebetween. To achieve this bias, the spring 202 may be cast, cut, or fabricated in the shape shown in FIG. 10. Thereafter, repositioning the first arm 214 away from the second arm 216 requires overcoming the bias of the spring, principally the bias attributed to the U-shaped end 210. When no active force is exerted upon the arms 214, 216, the arms will default to the position shown in FIG. 8. Consequently, when positioning the clip 200 to occlude bodily tissue, such as a left atrial appendage, the clip 200 is forced open so that the ends of the arms 214, 216 are forced farther away from one another to create a vertical gap between the runners 204, 206. This vertical gap is wide enough to allow bodily tissue to interpose the runners 204, 206 and, when the active force is no longer exerted upon the arms 214, 216, the bias of the spring 202 is operative to force the runners toward one another and discontinue circulation across the tissue interposing the runners. Eventually, the absence of circulation to one side of the clamped tissue leads to atrophy and occlusion of the bodily tissue in question.

As discussed previously, occlusion of the bodily tissue is accomplished through transferal of the forces imparted by the spring 202 through the runners 204, 206 and transmitted to the tissue as a pressure profile. The presence of proximal and distal spring bias allows the runners 204, 206 to balance the force independently at the proximal and distal ends, allowing for non-uniform shapes of tissue to be evenly compressed between the runners. The desired pressure can be obtained through adjustment of both the spring force and the runners 204, 206 shape and size. The spring force is a function of the shape, thickness, and width of the spring 202 material and each can be independently adjusted to obtain the desired force at the desired separation. Additionally, it is desired that as the tissue atrophies, a significant force continues to be applied even as the runners 204, 206 compress the tissue between them to near zero or zero thickness. This "zero offset force" can be adjusted through design of the shape of the spring 202 causing the "free state" of the contact points of the spring to the runners 204, 206 to become closer together or to even offset in the negative direction. It will be understood by those with ordinary skill in the art that this offset may be designed into the spring 202 or may be introduced through intentional plastic deformation of the spring.

Referencing FIGS. 13-18, a third exemplary occlusion clip 300 comprises a spring 302 mounted to a first runner 304 and a second runner 306 using a pair of dowels 308. The spring 302 includes a U-shaped end 310 from which extends a first arm 314 and a second arm 316. The first arm 314 is mounted to the first runner 304 using a first dowel 308, whereas the second arm 316 is mounted to the second runner 306 using a second dowel 308. In this exemplary embodiment, the first arm 314 has a rectangular, linear cross-section except for a distal end 318. The distal end 318 is rounded over and includes an orifice 324 configured to receive a dowel 308. Similarly, the second arm 316 also has a rectangular, linear or circular cross-section except for a rounded distal end 328. In this exemplary embodiment, the rounded end 328 includes an orifice 330 configured to receive the dowel 308. In this exemplary embodiment, the longitudinal length of each of the arms 314, 316 is approximately equal.

In addition to the first and second arms 314, 316, a secondary appendage 334 is mounted to the U-shaped end 310. In exemplary form, the secondary appendage 334 is inset with respect to the U-shaped end 310 and includes an arcuate portion 336 that approximates the curvature of the U-shaped portion until transitioning to a linear portion 338 that extends distally and divergent with respect to the first arm 314. Specifically, the linear portion 338 is acutely angled with respect to the first arm 314.

The first and second runners 304, 306 have essentially the same shape. Specifically, both runners 304, 306 include a pair of parallel walls 350, a longitudinal wall 352, and an end wall 354 that is concurrently mounted to the foregoing walls. The longitudinal wall 352 interposes and joins the parallel walls 350. In exemplary form, the interior surfaces 358 of the parallel walls 350 are planar and parallel to one another. These planar surfaces 358 cooperate with a planar interior surface 360 of the longitudinal wall 352 to delineate a block U-shaped longitudinal cavity 361 where the planar surfaces of the parallel walls are perpendicular to the planar surface of the longitudinal wall. In addition, the end wall 354 interposes and joins the parallel walls 350 to provide a longitudinal end cap. An interior surface 362 of the end wall is arcuately shaped and cooperates with the planar surfaces 358 of the parallel walls 350 to delineate a rounded U-shaped vertical cavity. In sum, the longitudinal end 366 of the runners 304, 306 opposite the end wall 354 is open, as is the vertical end opposite the planar interior surface 360 of the longitudinal wall 352.

The exterior of each runner 304, 306 includes a blunt end 370 that is rounded over at its periphery to join opposing longitudinal planar surfaces 372 and an arcuate longitudinal surface 374. The longitudinal arcuate surfaces 374 are adapted to be the element of each runner 304, 306 that is closest to one another and interposed by tissue when in a tissue occluding position.

As introduced previously, the first and second runners 304, 306 are mounted to the spring 302 using respective dowels 308. Consequently, the first runner 304 includes a pair of openings 376 that extend through the parallel walls 350 and are coaxial with one another. In this exemplary embodiment, the openings 376 are cylindrical and arranged approximately at eighty percent of the longitudinal length (i.e., nearest the distal end) of the first runner 304. Likewise, the second runner 306 includes a pair of openings 378 that extend through the parallel walls 350 and are coaxial with one another. In this exemplary embodiment, the openings 378 are cylindrical and the first pair of openings 378 are arranged approximately at eighty percent of the longitudinal length (i.e., nearest the distal end).

Assembly of the third exemplary occlusion clip 300 includes longitudinally sliding the runners 304, 306 with respect to the spring 302 when no dowels 308 are present.

By way of example, the first runner 304 is oriented to be slightly angled with respect to the first arm 314 so that the open end of the first runner 304 is longitudinally aligned to receive the rounded distal end 318. Thereafter, the first runner 304 is repositioned with respect to the first arm 314 so that the distal end 318 and the secondary appendage 334 are longitudinally repositioned within the U-shaped cavity 361 until the distal end 318 is aligned with the pair of openings 376. Thereafter, the dowel 308 is inserted through the pair of openings 376 so that the dowel and the planar interior surface 360 of the longitudinal wall 352 sandwich the distal end 318. After the dowel 308 is in position, the first runner 304 may not be longitudinally or vertically repositioned with respect to the first arm 314. But the first runner 304 may be rotationally repositionable with respect to the first arm 314 about an axis coaxial with the longitudinal length of the dowel 308 where the bias of the secondary appendage 334 retards rotation of the proximal end of the runner 304 to approximate a parallel orientation with respect to the secondary appendage. Mounting of the second runner 306 to the second arm 316 follows a similar process.

Mounting the second runner 306 to the second arm 316 may include longitudinally sliding the second runner 306 with respect to the spring 302 when no dowel 308 extends through the second runner. For example, the second runner 306 is oriented in parallel with the second arm 316 so that the open end 366 of the first runner 306 is longitudinally aligned to receive the rounded distal end 328. Thereafter, the second runner 306 is repositioned with respect to the second arm 316 so that the rounded distal end 328 is longitudinally repositioned within the U-shaped cavity 361 until the rounded distal end is aligned with the pair of openings 378. Thereafter, the dowel 308 is inserted through the pair of opening 378 so that the dowel and the planar interior surface 360 of the longitudinal wall 352 sandwich the distal end 328. After the dowel 308 is in position, the second runner 306 may not be longitudinally or vertically repositioned with respect to the second arm 316, but may be rotationally repositionable with respect to the second arm 316 about an axis coaxial with the longitudinal length of the dowel 308.

In operation, the spring 302 operates to bias the runners 304, 306 toward one another to exert an occlusion pressure upon tissue captured therebetween. To achieve this bias, the spring 302 may be cast, cut, or fabricated in the shape shown in FIG. 16. Thereafter, repositioning the first arm 314 away from the second arm 316 requires overcoming the bias of the spring 302, principally the bias attributed to the U-shaped end 310 and the secondary appendage 334. When no active force is exerted upon the arms 314, 316 and the secondary appendage 334, the arms and secondary appendage will default to the position shown in FIG. 14. Consequently, when positioning the clip 300 to occlude bodily tissue, such as a left atrial appendage, the clip 300 is forced open so that the distal ends of the arms 314, 316 are forced farther away from one another to create a vertical gap between the runners 304, 306. This vertical gap is wide enough to allow bodily tissue to interpose the runners 304, 306 and, when the active force is no longer exerted upon the arms 314, 316 and secondary appendage 334, the bias of the spring 302 is operative to force the runners toward one another and discontinue circulation across the tissue interposing the runners. Eventually, the absence of circulation to one side of the clamped tissue leads to atrophy and occlusion of the bodily tissue in question.

As introduced previously, occlusion of the bodily tissue is accomplished through transferal of the forces imparted by the spring 302 through the runners 304, 306 and transmitted to the tissue as a pressure profile. The presence of proximal and distal spring bias allows the occlusion clip runners 304, 306 to balance the force independently at the proximal and distal ends, allowing for non-uniform shapes of tissue to be evenly compressed between the runners. The desired pressure can be obtained through adjustment of both the spring force and the runner 304, 306 shape and size. The spring force is a function of the shape, thickness, and width of the spring 302 material and each can be independently adjusted to obtain the desired force at the desired separation. Additionally, it is desired that as the tissue atrophies, a significant force continues to be applied even as the runners 304, 306 compress the tissue between them to near zero or zero thickness. This "zero offset force" can be adjusted through design of the shape of the spring 302 causing the "free state" of the contact points of the spring to the runners 304, 306 to become closer together or to even offset in the negative direction. It will be understood by those with ordinary skill in the art that this offset may be designed into the spring 302 or may be introduced through intentional plastic deformation of the spring.

Referencing FIGS. 19-24, a fourth exemplary occlusion clip 400 comprises a spring 402 mounted to a first runner 404 and a second runner 406 using a pair of dowels 408. The spring 402 includes a U-shaped end 410 from which extends a first arm 414 and a second arm 416. The first arm 414 is mounted to the first runner 404 using the first dowel 408, whereas the second arm 416 is mounted to the second runner 406 using the second dowel 408. In this exemplary embodiment, the first arm 414 has a rectangular or circular cross-section except for a distal end 418. The first arm 414 includes a first linear segment 420 that is obtusely angled with respect to a second linear segment 422 that terminates at the distal end 418. The distal end 418 is rounded over and includes an orifice 424 configured to receive the dowel 408. Similarly, the second arm 416 also has a rectangular or circular, linear cross-section except for a rounded distal end 428. The second arm 416 includes a first linear segment 430 that is obtusely angled with respect to a second linear segment 432 that terminates at the distal end 428. In this exemplary embodiment, the rounded end 428 includes an orifice 434 configured to receive the dowel 408. In this exemplary embodiment, the longitudinal length of each of the arms 414, 416 is approximately equal.

In addition to the first and second arms 414, 416, a pair of secondary appendages 444, 446 is mounted to the U-shaped end 410. In exemplary form, the secondary appendages 444, 446 are inset with respect to the U-shaped end 410 and each appendage includes an arcuate portion 448, 449 that approximates the curvature of the U-shaped portion until transitioning to a linear portion 438, 440. The first linear portion 438 extends distally and divergent with respect to the first arm 414, whereas the second linear portion 440 extends distally and divergent with respect to the second arm 416. Specifically, the first linear portion 438 is acutely angled with respect to the first arm 414, while the second linear portion 440 is acutely angled with respect to the second arm 416.

The first and second runners 404, 406 have essentially the same shape. Specifically, both runners 404, 406 include a pair of parallel walls 450, a longitudinal wall 452, and an end wall 454 that is concurrently mounted to the foregoing walls. The longitudinal wall 452 interposes and joins the parallel walls 450. In exemplary form, the interior surfaces 458 of the parallel walls 450 are planar and parallel to one another. These planar surfaces 458 cooperate with a planar interior surface 460 of the longitudinal wall 452 to delineate a block U-shaped longitudinal cavity 461 where the planar surfaces of the parallel walls 450 are perpendicular to the planar surface of the longitudinal wall. In addition, the end wall 454 interposes and joins the parallel walls 450 to provide a longitudinal end cap. An interior surface 462 of the end wall is arcuately shaped and cooperates with the planar surfaces 458 of the parallel walls 450 to delineate a rounded U-shaped vertical cavity. In sum, the longitudinal end 466 of the runners 404, 406 opposite the end wall 454 is open, as is the vertical end opposite the planar interior surface 460 of the longitudinal wall 452.

The exterior of each runner 404, 406 includes a blunt end 470 that is rounded over at its periphery to join opposing longitudinal planar surfaces 472 and an arcuate longitudinal surface 474. The longitudinal arcuate surfaces 474 are adapted to be the element of each runner 404, 406 that is closest to one another and interposed by tissue when in a tissue occluding position.

As introduced previously, the first and second runners 404, 406 are mounted to the spring 402 using respective dowels 408. Consequently, the first and second runners 404, 406 each include a pair of openings 476 that extend through the parallel walls 450 and are coaxial with one another. In this exemplary embodiment, the openings 476 are cylindrical and arranged approximately at eighty percent of the longitudinal length (i.e., nearest the distal end) of the runners 404, 406.

Assembly of the fourth exemplary occlusion clip 400 includes longitudinally sliding the runners 404, 406 with respect to the spring 402 when no dowels 408 are present. By way of example, the first runner 404 is oriented to be slightly angled with respect to the first arm 414 so that the open end of the first runner 404 is longitudinally aligned to receive the rounded distal end 418. Thereafter, the first runner 404 is repositioned with respect to the first arm 414 so that the distal end 418 and a first of the secondary appendages 438 are longitudinally repositioned within the U-shaped cavity 461 until the distal end 418 is aligned with the pair of openings 476. Thereafter, the dowel 408 is inserted through the pair of openings 476 so that the dowel and the planar interior surface 460 of the longitudinal wall 452 sandwich the distal end 418. After the dowel 408 is in position, the first runner 404 may not be longitudinally or vertically repositioned with respect to the first arm 414. But the first runner 404 may be rotationally repositionable with respect to the first arm 414 about an axis coaxial with the longitudinal length of the dowel 408 where the bias of a first of the secondary appendages 438 retards rotation of the proximal end of the runner 404 to approximate a parallel orientation with respect to the secondary appendage. Mounting of the second runner 406 to the second arm 416 follows a similar process.

Mounting the second runner 406 to the second arm 416 may include longitudinally sliding the runner 406 with respect to the spring 402 when no dowel 408 extends through the second runner. For example, the second runner 406 is oriented to be slightly angled with respect to the second arm 416 so that the open end of the second runner 406 is longitudinally aligned to receive the rounded distal end 428. Thereafter, the second runner 406 is repositioned with respect to the second arm 416 so that the distal end 428 and a second of the secondary appendages 440 are longitudinally repositioned within the U-shaped cavity 461 until the distal end 428 is aligned with the pair of openings 476. Thereafter, the dowel 408 is inserted through the pair of openings 476 so that the dowel and the planar interior surface 460 of the longitudinal wall 452 sandwich the distal end 428. After the dowel 408 is in position, the second runner 406 may not be longitudinally or vertically repositioned with respect to the second arm 416. But the second runner 406 may be rotationally repositionable with respect to the second arm 416 about an axis coaxial with the longitudinal length of the dowel 408 where the bias of a second of the secondary appendages 440 retards rotation of the proximal end of the runner 406 to approximate a parallel orientation with respect to the secondary appendage.

In operation, the spring 402 operates to bias the runners 404, 406 toward one another to exert an occlusion pressure upon tissue captured therebetween. To achieve this bias, the spring 402 may be cast, cut, or fabricated in the shape shown in FIG. 22. Thereafter, repositioning the first arm 414 away from the second arm 416 requires overcoming the bias of the spring, principally the bias attributed to the U-shaped end 410 and the secondary appendages 438, 440. When no active force is exerted upon the arms 414, 416 and the secondary appendages 438, 440, the arms and appendages will default to the position shown in FIG. 20. Consequently, when positioning the clip 400 to occlude bodily tissue, such as a left atrial appendage, the clip 400 is forced open so that the distal ends of the arms 414, 416 are forced farther away from one another to create a vertical gap between the runners 404, 406. This vertical gap is wide enough to allow bodily tissue to interpose the runners 404, 406 and, when the active force is no longer exerted upon the arms 414, 416 and secondary appendages 438, 440, the bias of the spring 402 is operative to force the runners toward one another and discontinue circulation across the tissue interposing the runners. Eventually, the absence of circulation to one side of the clamped tissue leads to atrophy and occlusion of the bodily tissue in question.

As mentioned, occlusion of the bodily tissue is accomplished through transferal of the forces imparted by the spring 402 through the runners 404, 406 and transmitted to the tissue as a pressure profile. The presence of proximal and distal spring bias allows the occlusion clip runners 404, 406 to balance the force independently at the proximal and distal ends, allowing for non-uniform shapes of tissue to be evenly compressed between the runners. The desired pressure can be obtained through adjustment of both the spring force and the runner 404, 406 shape and size. The spring force is a function of the shape, thickness, and width of the spring 402 material and each can be independently adjusted to obtain the desired force at the desired separation. Additionally, it is desired that as the tissue atrophies, a significant force continues to be applied even as the runners 404, 406 compress the tissue between them to near zero or zero thickness. This "zero offset force" can be adjusted through design of the shape of the spring 402 causing the "free state" of the contact points of the spring to the runners 404, 406 to become closer together or to even offset in the negative direction. It will be understood by those with ordinary skill in the art that this offset may be designed into the spring 402 or may be introduced through intentional plastic deformation of the spring.

Referencing FIGS. 25-31, a fifth exemplary occlusion clip 500 comprises a spring 502 mounted to a first runner 504 and a second runner 506 using a pair of dowels 508. The spring 502 includes a V-shaped end 510 from which extends a first arm 514 and a second arm 516. The first arm 514 is mounted to the first runner 504 using the first dowel 508, whereas the second arm 516 is mounted to the second runner 506 using the second dowel 508. In this exemplary embodiment, the first arm 514 has a rectangular cross-section except for a rounded distal end 518. The first arm 514 is longitudinally arcuate and terminates at the distal end 518. The distal end 518 includes an orifice 524 configured to receive the dowel 508. Similarly, the second arm 516 also has a rectangular cross-section except for a rounded distal end 528. The second arm 516 is longitudinally arcuate and terminates at the distal end 528. In this exemplary embodiment, the rounded end 528 includes an orifice 534 configured to receive the dowel 508. In exemplary form, the longitudinal length of each of the arms 514, 516 is approximately equal.

In addition to the first and second arms 514, 516, a pair of secondary appendages 544, 546 is mounted to the V-shaped end 510. In exemplary form, the secondary appendages 544, 546 are inset with respect to the V-shaped end 510 and each appendage is longitudinally arcuate. The first secondary appendage 544 extends distally and divergent with respect to the first arm 514, whereas the second secondary appendage 546 extends distally and divergent with respect to the second arm 516.

The first and second runners 504, 506 have essentially the same shape. Specifically, both runners 504, 506 include a pair of parallel walls 550, a longitudinal wall 552, and an end wall 554 that is concurrently mounted to the foregoing walls. The longitudinal wall 552 interposes and joins the parallel walls 550. In exemplary form, the interior surfaces 558 of the parallel walls 550 are planar and parallel to one another. These planar surfaces 558 cooperate with a planar interior surface 560 of the longitudinal wall 552 to delineate a block U-shaped longitudinal cavity 561 where the planar surfaces of the parallel walls are perpendicular to the planar surface of the longitudinal wall. In addition, the end wall 554 interposes and joins the parallel walls 550 to provide a longitudinal end cap. An interior surface 562 of the end wall is arcuately shaped and cooperates with the planar surfaces 558 of the parallel walls 550 to delineate a rounded U-shaped vertical cavity. In sum, the longitudinal end 566 of the runners 504, 506 opposite the end wall 554 is open, as is the vertical end opposite the planar interior surface 560 of the longitudinal wall 552.

The exterior of each runner 504, 506 includes a blunt end 570 that is rounded over at its periphery to join opposing longitudinal planar surfaces 572 and an arcuate longitudinal surface 574. The longitudinal arcuate surfaces 574 are adapted to be the element of each runner 504, 506 that is closest to one another and interposed by tissue when in a tissue occluding position.

As introduced previously, the first and second runners 504, 506 are mounted to the spring 502 using respective dowels 508. Consequently, the first and second runners 504, 506 each include a pair of openings 576 that extend through the parallel walls 550 and are coaxial with one another. In this exemplary embodiment, the openings 576 are cylindrical and arranged approximately at eighty percent of the longitudinal length (i.e., nearest the distal end) of the runners 504, 506.

In this exemplary embodiment, a wedge 580 is coupled to the spring 502 to change the bias exerted by the first and second arms 514, 516. In this exemplary embodiment, the wedge 580 is welded to the spring 502. Exemplary forms of welding include, without limitation, sonic welding, friction welding (including friction stir welding), electromagnetic pulse welding, co-extrusion welding, cold welding, diffusion bonding, exothermic welding, high frequency welding, hot pressure welding, and induction welding. Nevertheless, other forms of attachment may be utilized to mount the wedge 580 to the spring 502 using various forms of attachment including, without limitation, adhesive, friction fit, and snap-fit (including detents, etc.).

Those skilled in the art will be aware that changing the shape of the wedge 580 with respect to the spring 502 is operative to change the bias exerted by the first and second arms 514, 516. Accordingly, the shape and angle of the wedge 580 and the cavity within the spring 502 into which the wedge is received is a matter of design choice. For example, as the pie-shape of the wedge increases in angle, the bias exerted upon the first and second arms 514, 516 will generally increase. Conversely, as the pie-shape of the wedge 580 decreases in angle, the bias exerted upon the first and second arms 514, 516 will generally decrease. It should be understood that shapes other than a pie-shape may be used to define the contour of the wedge 580. Those skilled in the art in view of the disclosure herein will readily understand these design alternatives.

Assembly of the fifth exemplary occlusion clip 500 includes longitudinally sliding the runners 504, 506 with respect to the spring 502 when no dowels 508 are present. By way of example, the first runner 504 is oriented to be slightly angled with respect to the first arm 514 so that the open end of the first runner 504 is longitudinally aligned to receive the rounded distal end 518. Thereafter, the first runner 504 is repositioned with respect to the first arm 514 so that the distal end 518 and a first of the secondary appendages 544 are longitudinally repositioned within the U-shaped cavity 561 until the distal end 518 is aligned with the pair of openings 576. Thereafter, the dowel 508 is inserted through the pair of openings 576 so that the dowel and the planar interior surface 560 of the longitudinal wall 552 sandwich the distal end 518. After the dowel 508 is in position, the first runner 504 may not be longitudinally or vertically repositioned with respect to the first arm 514. But the first runner 504 may be rotationally repositionable with respect to the first arm 514 about an axis coaxial with the longitudinal length of the dowel 508 where the bias of a first of the secondary appendages 544 retards rotation of the proximal end of the runner 504 to approximate a parallel orientation with respect to the secondary appendage. Mounting of the second runner 506 to the second arm 516 follows a similar process.

Mounting the second runner 506 to the second arm 516 may include longitudinally sliding the runner 506 with respect to the spring 502 when no dowel 508 extends through the second runner. For example, the second runner 506 is oriented to be slightly angled with respect to the second arm 516 so that the open end of the second runner 506 is longitudinally aligned to receive the rounded distal end 528. Thereafter, the second runner 506 is repositioned with respect to the second arm 516 so that the distal end 528 and a second of the secondary appendages 546 are longitudinally repositioned within the U-shaped cavity 561 until the distal end 528 is aligned with the pair of openings 576. Thereafter, the dowel 508 is inserted through the pair of openings 576 so that the dowel and the planar interior surface 560 of the longitudinal wall 552 sandwich the distal end 528. After the dowel 508 is in position, the second runner 506 may not be longitudinally or vertically repositioned with respect to the second arm 516. But the second runner 506 may be rotationally repositionable with respect to the second arm 516 about an axis coaxial with the longitudinal length of the dowel 508 where the bias of a second of the secondary appendages 546 retards rotation of the proximal end of the runner 506 to approximate a parallel orientation with respect to the secondary appendage.

Figure 28:
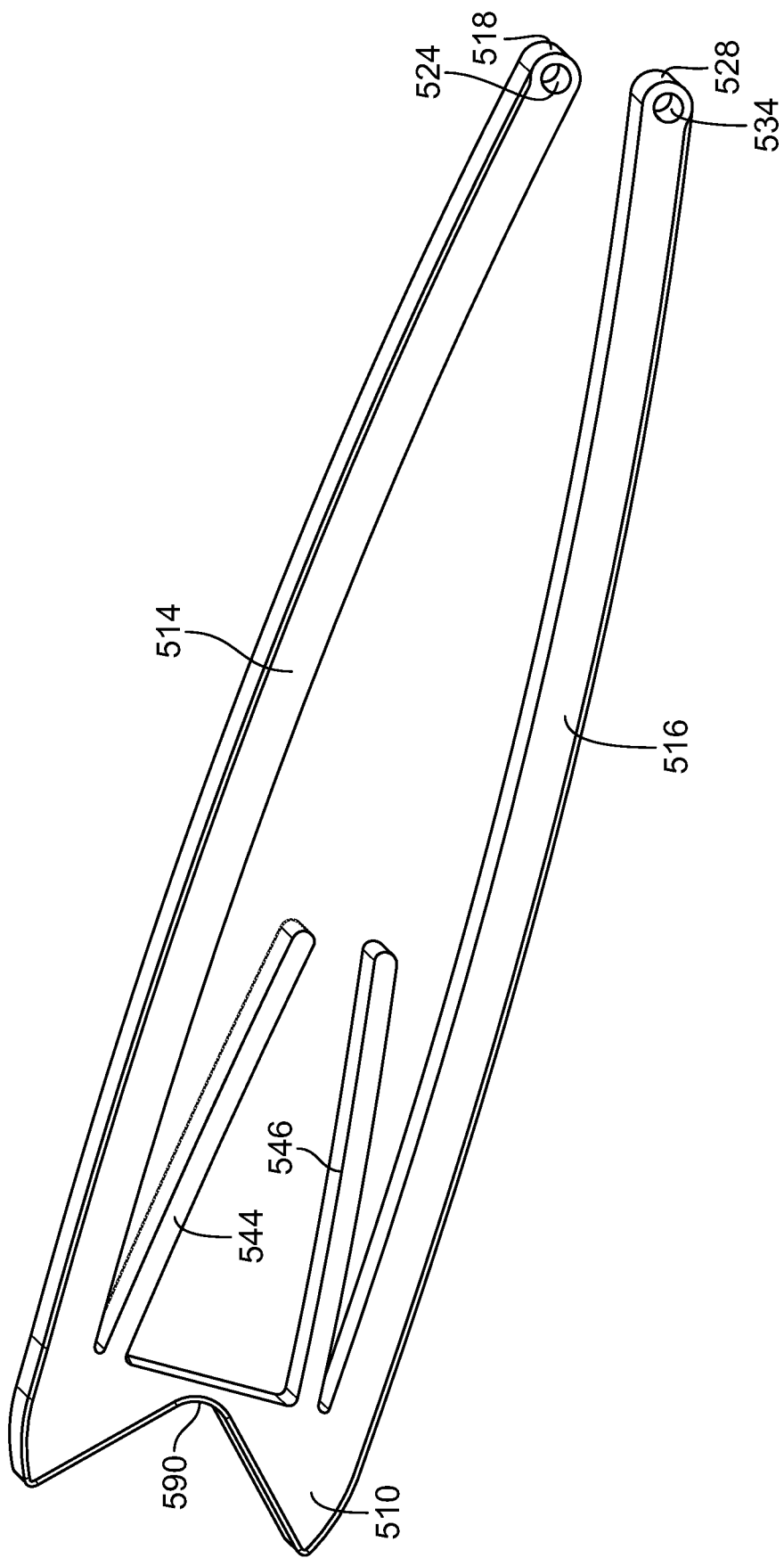
FIG. 28 is an elevated perspective view of the spring of the fifth exemplary occlusion clip of FIG. 25.
Figure 29:
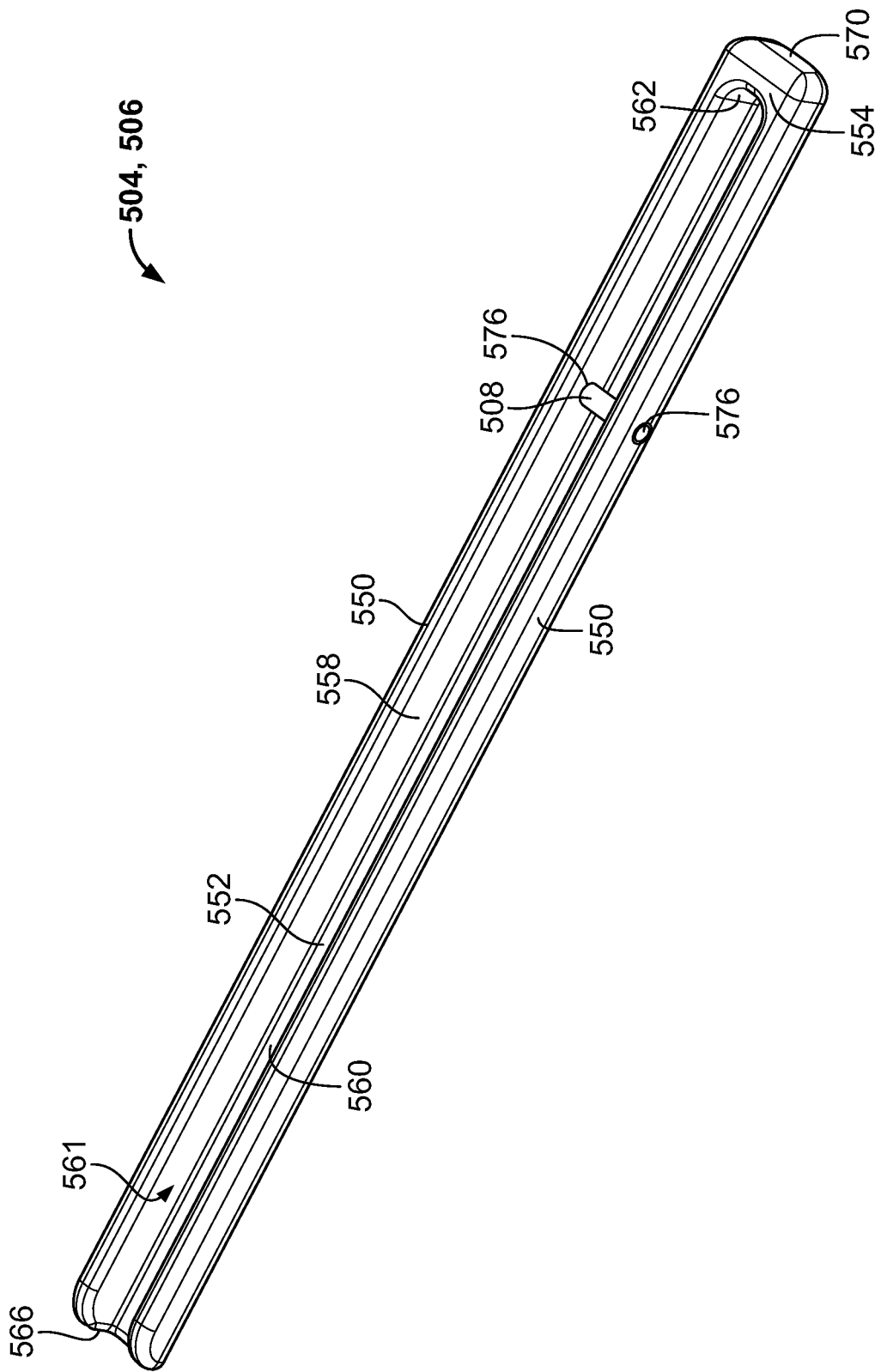
FIG. 29 is an elevated perspective view from the top of an exemplary runner and dowel of the fifth exemplary occlusion clip of FIG. 25.
Figure 30:
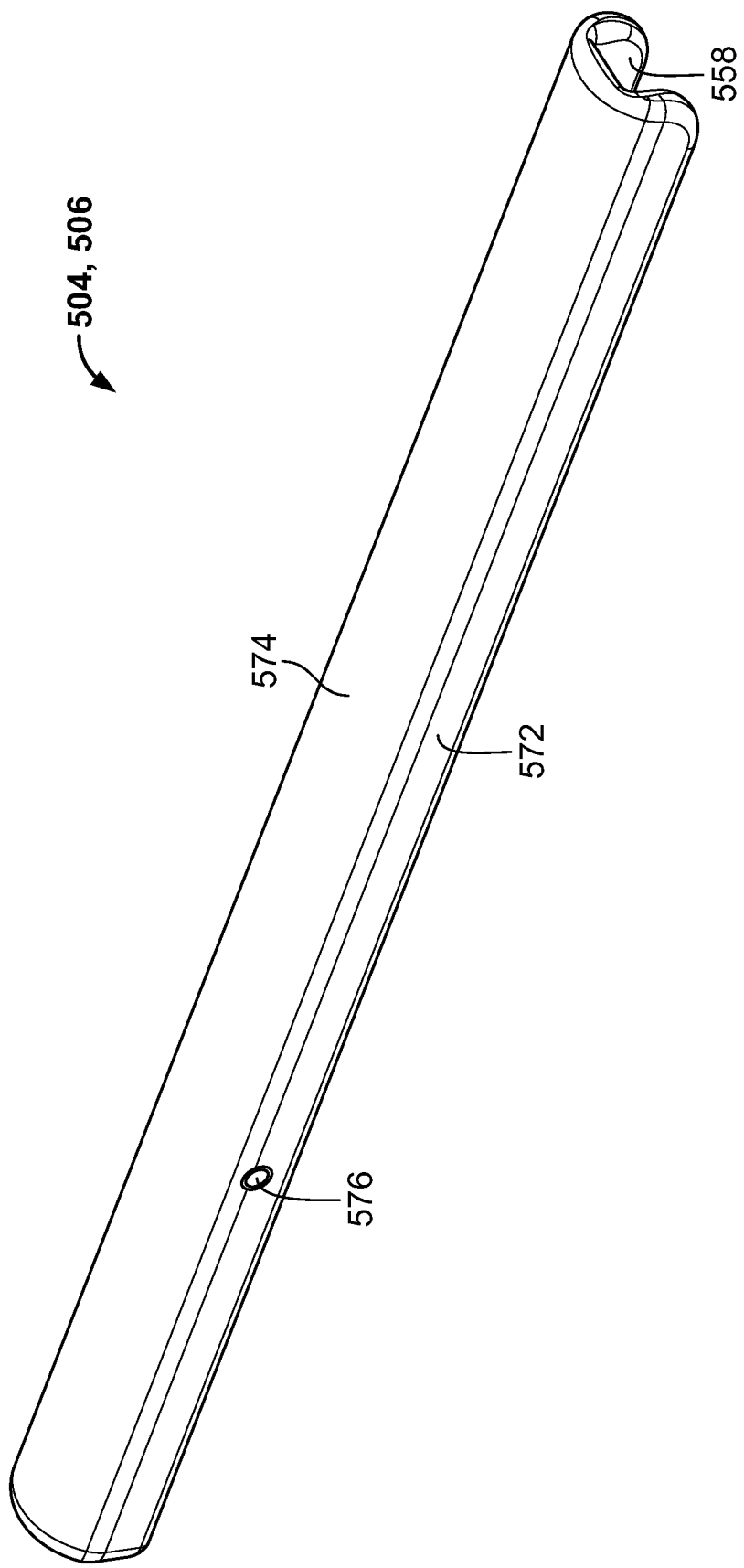
FIG. 30 is an elevated perspective view from the bottom of an exemplary runner of the fifth exemplary occlusion clip of FIG. 25.
Figure 31:
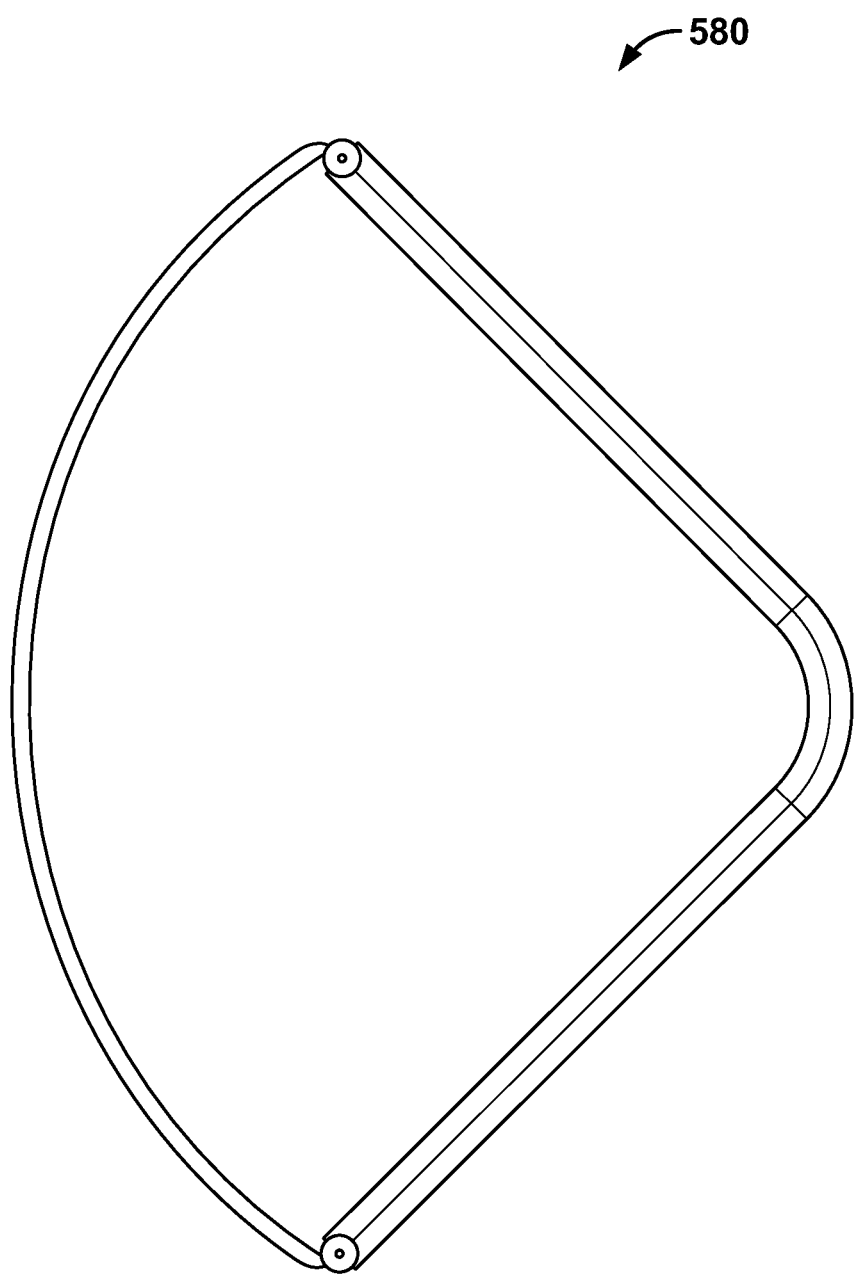
FIG. 31 is a right profile view of the wedge of the fifth exemplary embodiment of FIG. 25.
Figure 32:
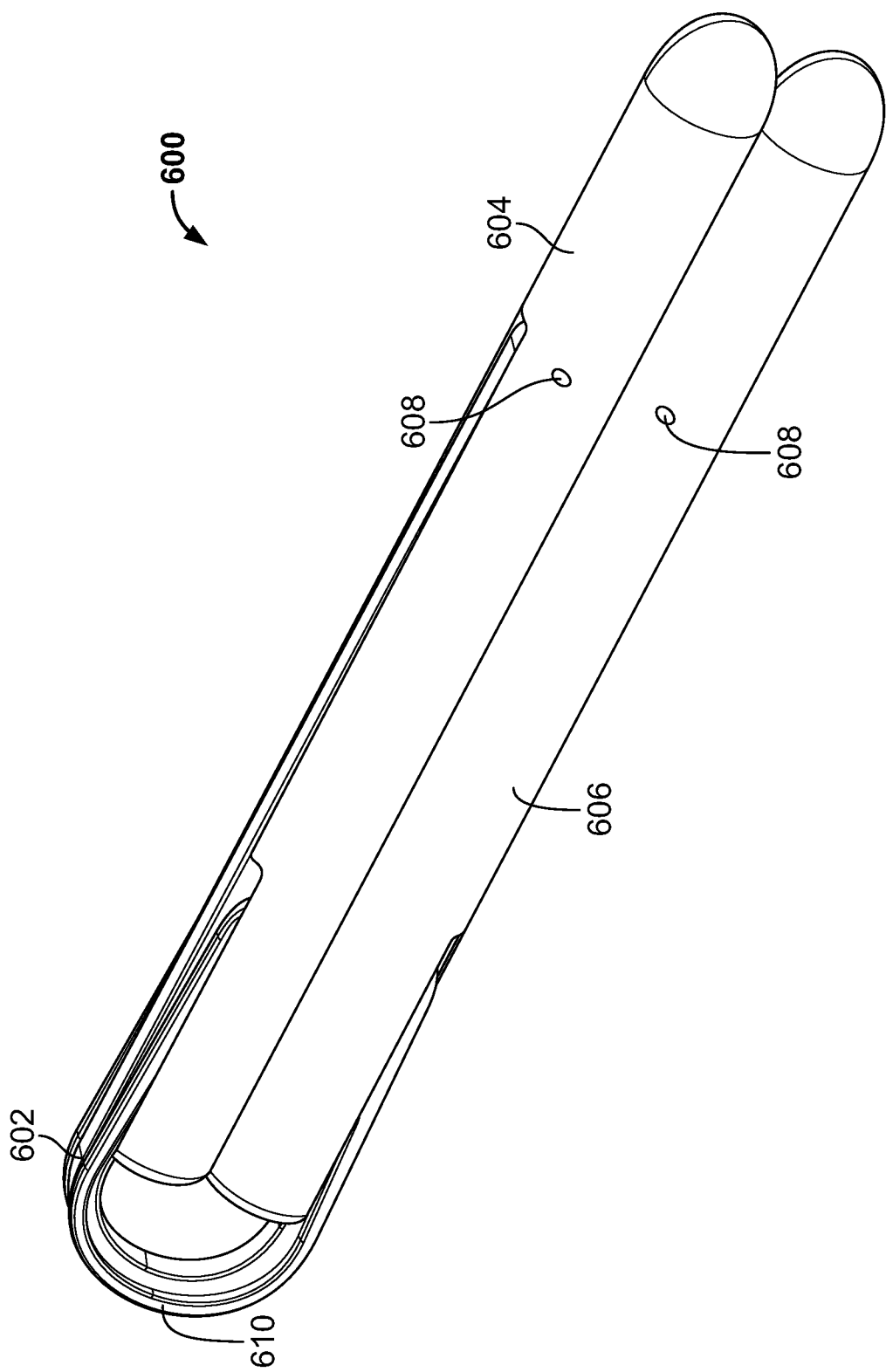
FIG. 32 is an elevated perspective view of a sixth exemplary occlusion clip in accordance with the present disclosure.
Figure 33:
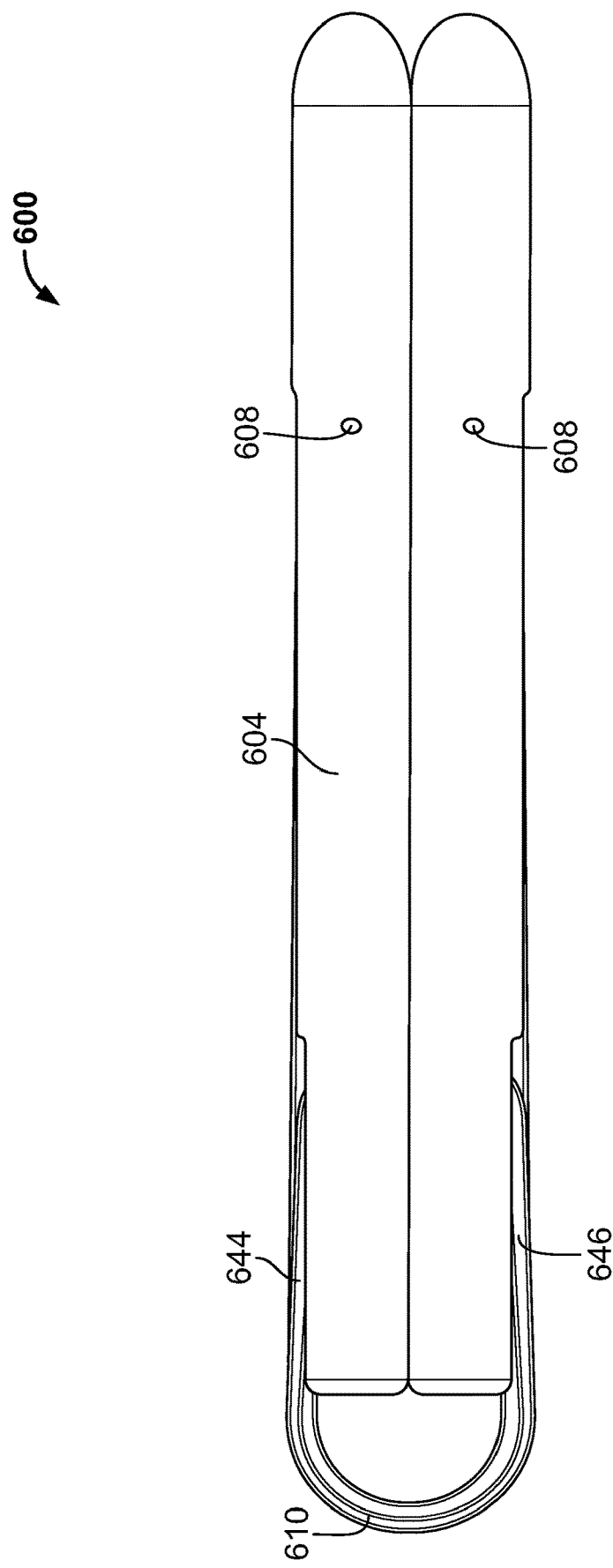
FIG. 33 is a right profile view of the sixth exemplary occlusion clip of FIG. 32.
Figure 34:
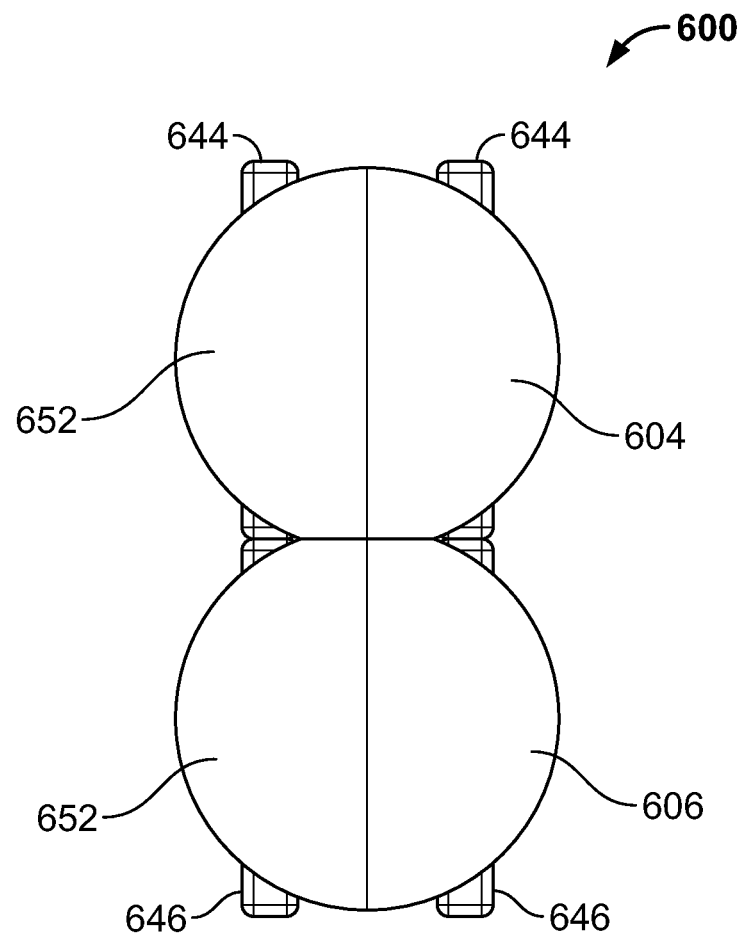
FIG. 34 is a frontal view of the sixth exemplary occlusion clip of FIG. 32.
Figure 35:
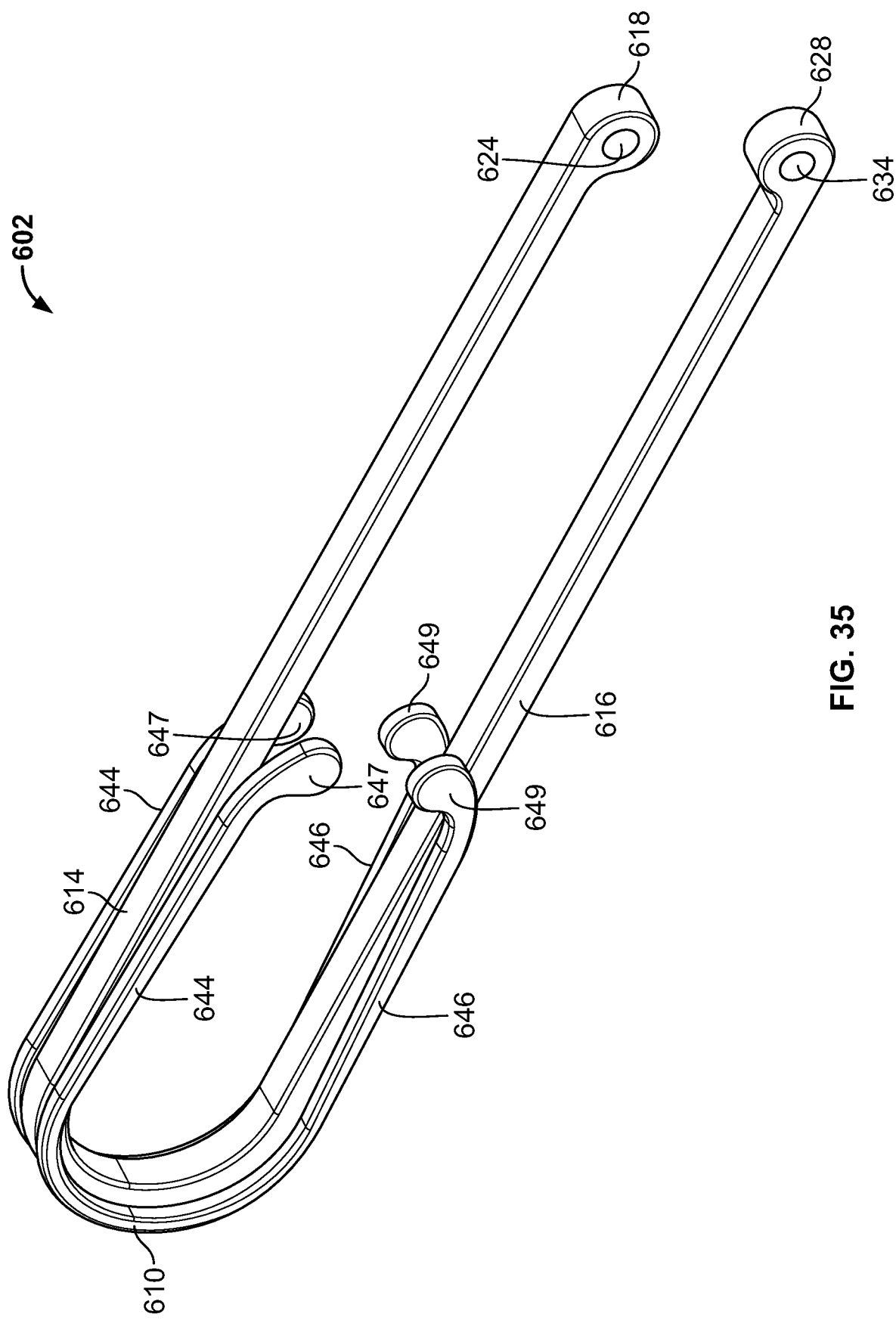
FIG. 35 is an elevated perspective view of the spring of the sixth exemplary occlusion clip of FIG. 32.
Figure 36:
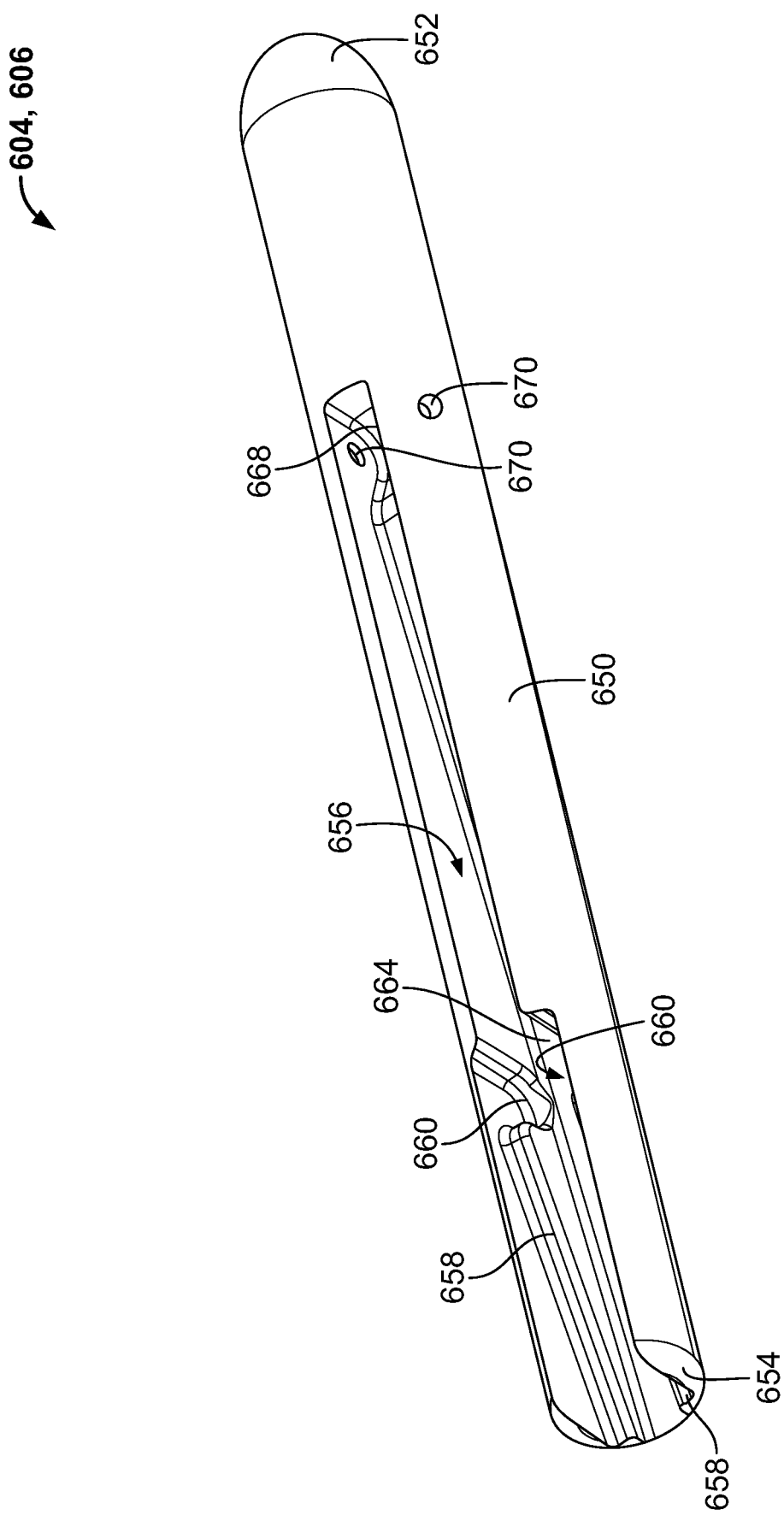
FIG. 36 is an elevated perspective view from the top of an exemplary runner of the sixth exemplary occlusion clip of FIG. 32.
Figure 37:
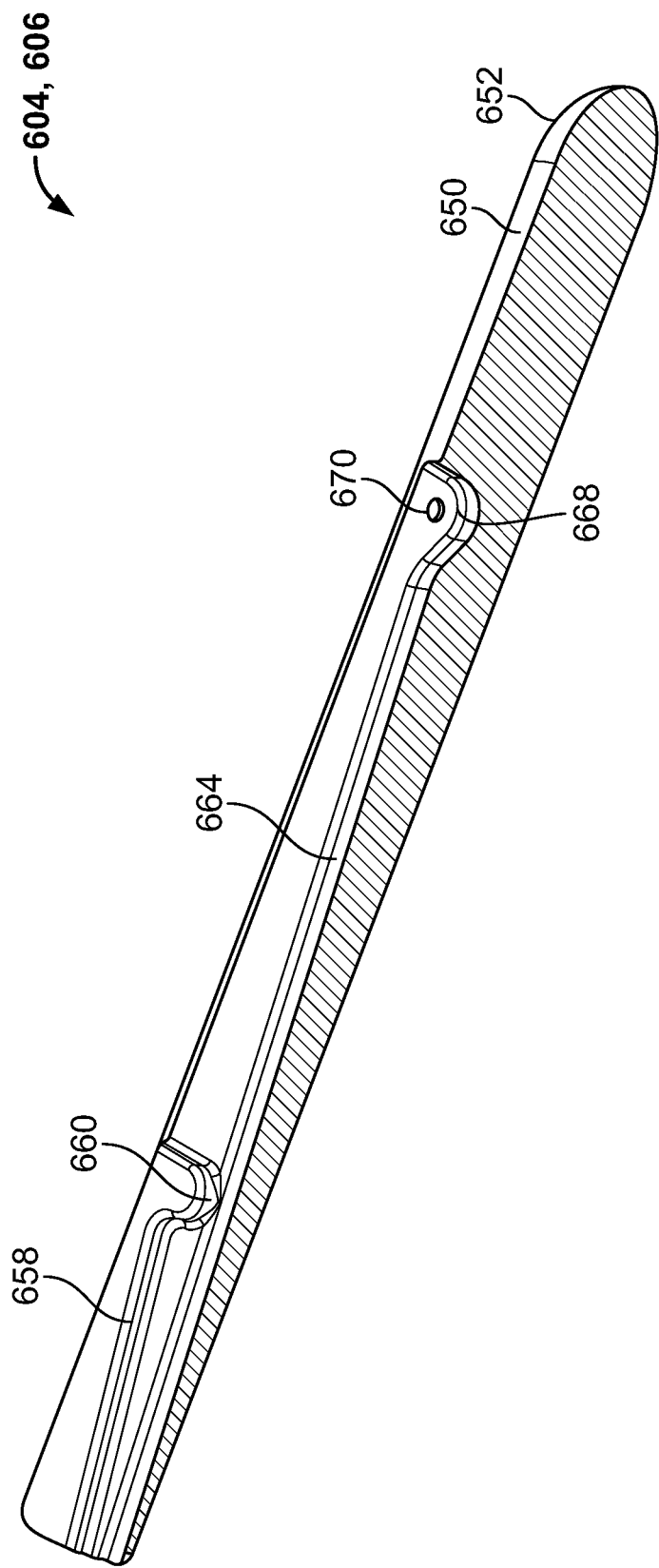
FIG. 37 is a longitudinal cross-sectional view of the exemplary runner of FIG. 36.

In operation, the spring 502 and wedge 580 operate to bias the runners 504, 506 toward one another to exert an occlusion pressure upon tissue captured therebetween To achieve this bias, the spring 502 may be cast, cut, or fabricated in the shape shown in FIG. 28. Repositioning the first arm 514 away from the second arm 516 requires overcoming the bias of the spring 502, principally the bias attributed to the V-shaped end 510 and the secondary appendages 544, 546. It should be noted that the bias of the spring 502 changes depending upon the properties of the wedge 580 including, without limitation, size, shape, and material composition. In exemplary form, the bias of the spring 502 is most often increased when the wedge 580 is mounted to the spring. Conversely, when the wedge 580 is not mounted to the spring 502, the bias associated with the spring will most often decrease as the spring 502 flexes about its hinge 590. When no active force is exerted upon the arms 514, 516 and the secondary appendages 544, 546, the arms and appendages will default to the position shown in FIG. 26. Consequently, when positioning the clip 500 to occlude bodily tissue, such as a left atrial appendage, the clip 500 is forced open so that the distal ends of the arms 514, 516 are forced farther away from one another to create a vertical gap between the runners 504, 506. This vertical gap is wide enough to allow bodily tissue to interpose the runners 504, 506 and, when the active force is no longer exerted upon the arms 514, 516 and secondary appendages 544, 546, the bias of the spring 502 is operative to force the runners toward one another and discontinue circulation across the tissue interposing the runners. Eventually, the absence of circulation to one side of the clamped tissue leads to atrophy and occlusion of the bodily tissue in question.

Similar to the foregoing embodiments, occlusion of the bodily tissue is accomplished through transferal of the forces imparted by the spring 502 through the runners 504, 506 and transmitted to the tissue as a pressure profile. The presence of proximal and distal spring bias allows the occlusion clip runners 504, 506 to balance the force independently at the proximal and distal ends, allowing for non-uniform shapes of tissue to be evenly compressed between the runners. The desired pressure can be obtained through adjustment of both the spring force and the runner 504, 506 shape and size. The spring force is a function of the shape, thickness, and width of the spring 502 material and each can be independently adjusted to obtain the desired force at the desired separation. Additionally, it is desired that as the tissue atrophies, a significant force continues to be applied even as the runners 504, 506 compress the tissue between them to near zero or zero thickness. This "zero offset force" can be adjusted through design of the shape of the spring 502 causing the "free state" of the contact points of the spring to the runners 504, 506 to become closer together or to even offset in the negative direction. It will be understood by those with ordinary skill in the art that this offset may be designed into the spring 502 or may be introduced through intentional plastic deformation of the spring.

Referencing FIGS. 32-37, a sixth exemplary occlusion clip 600 comprises a spring 602 mounted to a first runner 604 and a second runner 606 using a pair of dowels 608. The spring 602 includes a U-shaped end 610 from which extends a first arm 614 and a second arm 616. The first arm 614 is mounted to the first runner 604 using the first dowel 608, whereas the second arm 616 is mounted to the second runner 606 using the second dowel 608. In this exemplary embodiment, the first arm 614 has a rectangular or circular cross-section except for a rounded distal end 618. The first arm 614 is longitudinally linear and terminates at the distal end 618. The distal end 618 includes an orifice 624 configured to receive the dowel 608. Similarly, the second arm 616 also has a rectangular cross-section except for a rounded distal end 628. The second arm 616 is longitudinally linear and terminates at the distal end 628. In this exemplary embodiment, the rounded end 628 includes an orifice 634 configured to receive a dowel 608. In exemplary form, the longitudinal length of each of the arms 614, 616 is approximately equal.

In addition to the first and second arms 614, 616, a first and second pair of ancillary appendages 644, 646 are mounted to the U-shaped end 610. In exemplary form, the ancillary appendages 644, 646 sandwich a respective arm 614, 616. Each of the ancillary appendages 644, 646 comprises a rectangular cross-section except for a rounded distal end 647, 649. Each ancillary appendage 644, 646 is longitudinally arcuate to curve toward the interior interposing the arms 614, 616, where the distal ends 647, 649 are closest to one another.

The first and second runners 604, 606 have essentially the same shape. Specifically, both runners 604, 606 have a cylindrical, linear exterior surface 650 that tapers to create a domed end 652. A proximal end 654 defines a U-shaped opening that leads into a longitudinally extending channel 656 delineated by interior walls configured to receive a respective arm 614, 616 and a respective pair of ancillary appendages 644, 646. In particular, the interior walls define a pair of spaced apart inclined, linear ramps 658 (from proximal to distal) that provide a bearing surface upon which a respective distal end 647, 649 slides. In order to fix the orientation and mount the ancillary appendages 644, 646 to the runner 604, 606, the interior of the runner adjacent the distal end of each ramp 658 defines a pocket 660. Interposing the pockets is a primary inclined linear ramp 664 (from proximal to distal) that provide a bearing surface upon which a respective distal end 618, 628 slides. In order to fix the orientation and mount a respective arm 614, 616 to a runner 604, 606, the interior of the runner adjacent the distal end of each ramp 658 defines a primary pocket 668. Extending transverse across this primary pocket is a pair of orifices 670 extending through the exterior surface 650. Each orifice 670 is cylindrical and sized to accept the dowel 608 in order to lock a respective arm 614, 616 to a respective runner 604, 606. In this exemplary embodiment, the orifices 670 are cylindrical and arranged approximately at eighty percent of the longitudinal length (i.e., nearest the distal end) of the runners 604, 606.

Assembly of the sixth exemplary occlusion clip 600 includes longitudinally sliding the runners 604, 606 with respect to the spring 602 when no dowels 608 are present. By way of example, the first runner 604 is oriented to be slightly angled with respect to the first arm 614 so that the open end of the first runner 604 is longitudinally aligned to receive the rounded distal end 618. Thereafter, the first runner 604 is repositioned with respect to the first arm 614 so that the distal end 618 and the first pair of ancillary appendages 644 are longitudinally repositioned within the U-shaped cavity 656. Initially, the rounded distal end 618 contacts and rides upon the primary ramp 664, followed by continued longitudinal movement that causes the distal ends 647 of the first ancillary appendages 644 to slide upon a respective linear ramp 658. Eventual longitudinal movement of the spring 602 with respect to the first runner 604 coincides with the rounded distal end 618 reaching the primary pocket 668 at approximately the same time as the distal ends 647 reaching respective pockets 660. Thereafter, the dowel 608 is inserted through the pair of openings 670 and through the orifice 624 of the first arm 614 to lock the first arm to the runner. After the dowel 608 is in position, the first runner 604 may not be longitudinally or vertically repositioned with respect to the first arm 614. But the first runner 604 may be rotationally repositionable with respect to the first arm 614 about an axis coaxial with the longitudinal length of the dowel 608 where the bias of the first pair of ancillary appendages 644 retards rotation of the proximal end of the runner 604. Mounting of the second runner 606 to the second arm 616 follows a similar process.

Mounting the second runner 606 to the second arm 616 may include longitudinally sliding the runner 606 with respect to the spring 602 when no dowel 608 extends through the second runner. For example, the second runner 606 is oriented to be slightly angled with respect to the second arm 616 so that the open end of the second runner 606 is longitudinally aligned to receive the rounded distal end 628. Thereafter, the second runner 606 is repositioned with respect to the second arm 616 so that the distal end 628 and the first pair of ancillary appendages 646 are longitudinally repositioned within the U-shaped cavity 656. Initially, the rounded distal end 628 contacts and rides upon the primary ramp 664, followed by continued longitudinal movement that causes the distal ends 649 of the second ancillary appendages 646 to slide upon a respective linear ramp 658. Eventual longitudinal movement of the spring 602 with respect to the second runner 606 coincides with the rounded distal end 628 reaching the primary pocket 668 at approximately the same time as the distal ends 649 reaching respective pockets 660. Thereafter, the dowel 608 is inserted through the pair of openings 670 and through the orifice 624 of the second arm 616 to lock the second arm to the second runner. After the dowel 608 is in position, the second runner 606 may not be longitudinally or vertically repositioned with respect to the second arm 616. But the second runner 606 may be rotationally repositionable with respect to the second arm 616 about an axis coaxial with the longitudinal length of the dowel 608 where the bias of the second pair of ancillary appendages 646 retards rotation of the proximal end of the second runner 606.

In operation, the spring 602 operates to bias the runners 604, 606 toward one another to exert an occlusion pressure upon tissue captured therebetween. To achieve this bias, the spring 602 may be cast, cut, or fabricated in the shape shown in FIG. 35. Repositioning the first arm 614 away from the second arm 616 requires overcoming the bias of the spring 602, principally the bias attributed to the U-shaped end 610. When no active force is exerted upon the arms 614, 616 and the ancillary appendages 644, 646, the arms and appendages will default to the position shown in FIG. 33. Consequently, when positioning the clip 600 to occlude bodily tissue, such as a left atrial appendage, the clip 600 is forced open so that the distal ends of the arms 614, 616 are forced farther away from one another to create a vertical gap between the runners 604, 606. This vertical gap is wide enough to allow bodily tissue to interpose the runners 604, 606 and, when the active force is no longer exerted upon the arms 614, 616 and ancillary appendages 644, 646, the bias of the spring 602 is operative to force the runners toward one another and discontinue circulation across the tissue interposing the runners. Eventually, the absence of circulation to one side of the clamped tissue leads to atrophy and occlusion of the bodily tissue in question.

Consistent with the foregoing embodiments, occlusion of the bodily tissue is accomplished through transferal of the forces imparted by the spring 602 through the runners 604, 606 and transmitted to the tissue as a pressure profile. The presence of proximal and distal spring bias allows the occlusion clip runners 604, 606 to balance the force independently at the proximal and distal ends, allowing for non-uniform shapes of tissue to be evenly compressed between the runners. The desired pressure can be obtained through adjustment of both the spring force and the runners 604, 606 shape and size. The spring force is a function of the shape, thickness, and width of the spring 602 material and each can be independently adjusted to obtain the desired force at the desired separation. Additionally, it is desired that as the tissue atrophies, a significant force continues to be applied even as the runners 604, 606 compress the tissue between them to near zero or zero thickness. This "zero offset force" can be adjusted through design of the shape of the spring 602 causing the "free state" of the contact points of the spring to the runners 604, 606 to become closer together or to even offset in the negative direction. It will be understood by those with ordinary skill in the art that this offset may be designed into the spring 602 or may be introduced through intentional plastic deformation of the spring.

The exemplary occlusion clips may be fabricated from any number of materials including, without limitation, plastics, composites, metals, and ceramics. For example, the exemplary runners and springs may both be fabricated from a biologically compatible titanium. By way of further example, the exemplary runners may be fabricated from a biologically compatible plastic and the springs fabricated from a biologically compatible metal. By way of further example, the runners may be fabricated from high density polyethylene and the springs may be fabricated from nitinol. Conversely, the exemplary runners may be fabricated from any biologically compatible material and the springs fabricated from a biologically compatible material exhibiting sufficient elastic characteristics. By way of further example, the runners may be fabricated from titanium and the springs fabricated from stainless steel. By way of further example, the runners and springs may be fabricated from bioabsorbable materials and/or materials that accommodate or promote the ingrowth of tissue.

It is also within the scope of the invention for the exemplary occlusion clips to be shrouded in a tissue ingrowth material. For example, the exemplary occlusion clips may be encased in a C-shaped, loop sleeve that is cylindrical and closed at opposing ends in order to accommodate opening and closing of the exemplary clips (i.e., separation or spacing between the runners sufficient to position tissue therebetween). Those skilled in the art are familiar with tissue ingrowth materials such as porous fabrics, including knitted, braided, or woven PET yarn or including Gore Dualmesh (available from W. L. Gore & Associates, www.gore.com) that may be used to shroud the foregoing exemplary embodiments.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. An occlusion clip comprising:
a spring;
a first runner;
a second runner;
wherein the spring is configured to be mounted to the first runner and the second runner so that the occlusion clip is open on at least three sides and biases the first and second runner toward one another;
wherein the spring includes a first appendage operatively coupled to the first runner distal to a dominant dimension midpoint of the first runner to preclude longitudinal repositioning of a first distal portion of the spring with respect to the first runner and allow pivotal motion of the spring with respect to the first runner;
wherein the spring includes a second appendage operatively coupled to the second runner distal to a dominant dimension midpoint of the second runner to preclude longitudinal repositioning of a second distal portion of the spring with respect to the second runner and allow pivotal motion of the spring with respect to the second runner;
wherein the spring includes a third appendage that slidably engages the second runner proximal to the dominant dimension midpoint of the second runner, the third appendage being longitudinally repositionable with respect to the second runner so that the third appendage provides a bias constantly thereto when the occlusion clip is in a clamped position;
wherein a dominant axial dimension of the spring when biasing the first and second runners is no less than half of the dominant axial dimension of the occlusion clip;
wherein the spring extends proximally beyond the first runner and the second runner.

2. The occlusion clip of claim 1, further comprising a lock configured to mount at least one of the first runner and the second runner to the spring.

3. The occlusion clip of claim 2, wherein:
the lock includes a dowel received within an orifice associated with at least one of the spring, the first runner, and the second runner;
the spring includes a first arm and a second arm;
the first arm includes the first cam; and,
the second arm includes the second cam.

4. The occlusion clip of claim 3, wherein the lock includes a dowel received within an orifice associated with the first runner.

5. The occlusion clip of claim 3, wherein the lock includes a dowel received within an orifice associated with the first runner and the spring.

6. The occlusion clip of claim 3, wherein:
the lock includes a first dowel received within a first orifice associated with at least one of the first runner and the spring; and,
the lock includes a second dowel received within a second orifice associated with at least one of the second runner and the spring.

7. The occlusion clip of claim 2, wherein:
the lock allows pivotal movement between the spring and the first runner; and,
the lock inhibits longitudinal repositioning between the spring and the first runner.

8. The occlusion clip of claim 1, wherein:
the first runner includes an arcuate tissue contacting surface;
the second runner includes an arcuate tissue contacting surface; and,
the arcuate tissue contacting surface of the first runner faces the arcuate tissue contacting surface of the second runner when the first and second runners are mounted to the spring.

9. The occlusion clip of claim 1, further comprising:
a first lock configured to mount the first runner to the spring; and,
a second lock configured to mount the second runner to the spring.

10. The occlusion clip of claim 9, wherein:
the first runner includes at least one of a depression and an orifice configured to receive a portion of the first lock; and,
the second runner includes at least one of a depression and an orifice configured to receive a portion of the second lock.

11. The occlusion clip of claim 10, wherein:
the first runner includes an orifice configured to receive a portion of the first lock; and,
the second runner includes an orifice configured to receive a portion of the second lock.

12. The occlusion clip of claim 11, wherein:
the orifice of the first runner includes a first pair of orifices;
the orifice of the second runner includes a second pair of orifices;
the first lock includes a first dowel configured to be received by the first pair of orifices of the first runner; and,
the second lock includes a second dowel configured to be received by the second pair of orifices of the second runner.

13. The occlusion clip of claim 1, wherein:
the spring embodies a C-shape with a first leg and a second leg;
the first leg includes at least one of a cavity and an orifice configured to receive a first lock to mount the first leg to the first runner; and,
the second leg includes at least one of a cavity and an orifice configured to receive a second lock to mount the second leg to the second runner.

14. The occlusion clip of claim 13, wherein:
a distal end of the first leg includes a rounded end;
a distal end of the second leg includes a rounded end;
the distal end of the first leg includes the cavity configured to receive a first lock to mount the first leg to the first runner; and,
the distal end of the second leg includes the cavity configured to receive a second lock to mount the second leg to the second runner.

15. The occlusion clip of claim 14, wherein:
the first runner includes at least one of a first runner cavity and a first runner orifice configured to receive a portion of the first lock; and,
the second runner includes at least one of a second runner cavity and a second runner orifice configured to receive a portion of the second lock.

16. The occlusion clip of claim 15, wherein:
the first runner includes a first runner orifice;
the second runner includes a second runner orifice;
the first lock comprises a first dowel configured to be concurrently received within the first runner orifice and the cavity of the first leg to mount the first leg to the first runner; and,
the second lock comprises a second dowel configured to be concurrently received within the second runner orifice and the cavity of the second leg to mount the second leg to the second runner.

17. The occlusion clip of claim 1, wherein
the first runner includes a first open top, the first runner including a first interior surface partially delineating a first interior cavity that is open by way of the first open top;
the second runner includes a second open top, the second runner including a second interior surface partially delineating a second interior cavity that is open by way of the second open top;
wherein the first interior cavity is configured to receive a first portion of the spring distal to the dominant dimension midpoint of the first runner;
wherein the second interior cavity is configured to receive a second portion of the spring distal to the dominant dimension midpoint of the second runner;
wherein the first interior surface is configured to engage a first ancillary appendage of the spring proximal to the dominant dimension midpoint of the first runner; and,
wherein the second interior surface is configured to engage a second ancillary appendage of the spring proximal to the dominant dimension midpoint of the second runner.

18. The occlusion clip of claim 17, wherein:
the spring embodies a C-shape with a first leg and a second leg;
the first leg includes at least one of a cavity and an orifice configured to receive a first lock to mount the first leg to the first runner; and,
the second leg includes at least one of a cavity and an orifice configured to receive a second lock to mount the second leg to the second runner;
a distal end of the first leg includes a rounded end;
a distal end of the second leg includes a rounded end;
the distal end of the first leg includes the orifice configured to receive the first lock operative to mount the first leg to the first runner; and,
the distal end of the second leg includes the orifice configured to receive the second lock operative to mount the second leg to the second runner.

19. The occlusion clip of claim 18, wherein:
the first runner includes at least one of a first runner cavity and a first runner orifice configured to receive a portion of the first lock; and,
the second runner includes at least one of a second runner cavity and a second runner orifice configured to receive a portion of the second lock.

20. The occlusion clip of claim 19, wherein:
the first runner includes the first runner orifice;
the second runner includes the second runner orifice;
the first lock comprises a first dowel configured to be concurrently received within the first runner orifice and the orifice of the first leg to mount the first leg to the first runner; and,
the second lock comprises a second dowel configured to be concurrently received within the second runner orifice and the orifice of the second leg to mount the second leg to the second runner.

21. The occlusion clip of claim 1, further comprising a fabric interposing the first and second runners.

22. The occlusion clip of claim 1, further comprising a C-shaped fabric sleeve encapsulating the occlusion clip.

23. The occlusion clip of claim 1, wherein:
the dominant dimension midpoint of the first runner comprises an axial dominant dimension midpoint of the first runner; and,
the dominant dimension midpoint of the second runner comprises an axial dominant dimension midpoint of the second runner.

24. The occlusion clip of claim 1, further comprising a fabric sleeve enveloping the occlusion clip.

25. An occlusion clamp comprising:
a spring comprising a first elongated leg and a second elongated leg coupled together at a first end and independently repositionable with respect to one another at respective second ends so that the spring is open-ended, the spring having a dominant dimension, the spring including a secondary appendage interposing the first and second elongated legs;
a first runner configured to be rotationally repositionable with respect to the second end of the first elongated leg, the first runner comprising an elongated occlusion beam having an occlusion surface, the first runner having a dominant dimension;
a second runner configured to be rotationally repositionable with respect to the second end of the second elongated leg, the second runner comprising an elongated occlusion beam having an occlusion surface, the second runner having a dominant dimension, the second runner configured to be slidably repositionable longitudinally with respect to the spring;
wherein the second elongated leg of the spring is configured to apply a distal bias to the second runner distal to a dominant dimension midpoint of the second runner, the distal bias toward the first runner, and the secondary appendage is configured to apply a proximal bias to the second runner proximal to the dominant dimension midpoint of the second runner, the proximal bias toward the first runner; and,
wherein the dominant dimensions of the spring, first runner, and the second runner extend in generally the same direction.

26. The occlusion clamp of claim 25, wherein the spring includes at least one of a rectangular, circular, or oblong cross-section.

27. The occlusion clamp of claim 25, wherein:
the first elongated leg is coupled to the first runner at a first location;
the second elongated leg is coupled to the second runner at a second location; and,
the first location is approximately the same as the second location along the dominant dimension of the spring.

28. The occlusion clamp of claim 27, wherein:
a first pin is mounted to the first runner;
a second pin is mounted to the second runner;
the first elongated leg traps the first pin to couple the first elongated leg to the first runner; and,
the second elongated leg traps the second pin to couple the second elongated leg to the second runner.

29. The occlusion clamp of claim 28, wherein:
the first elongated leg includes a first orifice configured to receive the first pin so that the first elongated leg interposes the first pin and the first runner to couple the first elongated leg to the first runner; and, the second elongated leg includes a second orifice configured to receive the second pin so that the second elongated leg interposes the second pin and the second runner to couple the second elongated leg to the second runner.

30. The occlusion clamp of claim 29, wherein:
the first orifice is at least partially located within a trench of the first runner; and,
the second orifice is at least partially located within a trench of the second runner.

31. The occlusion clamp of claim 25, wherein:
the first and second elongated legs delineate a U-shaped primary spring; and,
the secondary appendage interposes the first and second elongated legs.

32. The occlusion clamp of claim 31, wherein:
the secondary appendage extends from a trough cooperatively formed by an intersection of the first and second elongated legs; and,
the secondary appendage comprises a partial U-shaped secondary spring.

33. The occlusion clamp of claim 25, wherein:
the spring further comprises an additional appendage mounted to at least one of the first elongated leg and the second elongated leg.

34. The occlusion clamp of claim 33, wherein:
the first elongated leg is coupled to the first runner at a first location;
the second elongated leg is coupled to the second runner at a second location; and,
the first location is approximately the same as the second location along the dominant dimension of the spring.

35. The occlusion clamp of claim 34, wherein:
a first pin is mounted to the first runner;
a second pin is mounted to the second runner;
the first elongated leg traps the first pin to mount the first elongated leg to the first runner; and,
the second elongated leg traps the second pin to mount the second elongated leg to the second runner.

36. The occlusion clamp of claim 35, wherein:
the first elongated leg includes a first orifice configured to receive the first pin so that the first elongated leg interposes the first pin and the first runner to mount the first elongated leg to the first runner; and,
the second elongated leg includes a second orifice configured to receive the second pin so that the second elongated leg interposes the second pin and the second runner to mount the second elongated leg to the second runner.

37. The occlusion clamp of claim 36, wherein:
the first orifice is at least partially received within a trench of the first runner; and,
the second orifice is at least partially received within a trench of the second runner.

38. The occlusion clamp of claim 33, wherein:
the first and second elongated legs delineate a U-shaped primary spring;
the secondary appendage interposes the first and second elongated legs; and
the additional appendage interposes the first and second elongated legs.

39. The occlusion clamp of claim 38, wherein:
the additional and secondary appendages extend from a trough cooperatively formed by an intersection of the first and second elongated legs; and,
the additional and secondary appendages cooperate to delineate a U-shaped secondary spring.

40. The occlusion clamp of claim 33, wherein:
the first and second elongated legs comprise a primary spring;
the secondary appendage interposes the first and second elongated legs; and
the additional appendage interposes the first and second elongated legs.

41. The occlusion clamp of claim 25, wherein:
the elongated occlusion beam of the first runner is linear and includes a linear occlusion surface; and,
the elongated occlusion beam of the second runner is linear and includes a linear occlusion surface.

42. The occlusion clamp of claim 25, wherein:
the elongated occlusion beam of the first runner is linear and includes an arcuate occlusion surface; and,
the elongated occlusion beam of the second runner is linear and includes an arcuate occlusion surface.

43. The occlusion clamp of claim 25, wherein:
the elongated occlusion beam of the first runner is arcuate and includes an arcuate occlusion surface; and,
the elongated occlusion beam of the second runner is arcuate and includes an arcuate occlusion surface.

44. The occlusion clamp of claim 25, wherein:
the elongated occlusion beam of the first runner is arcuate and includes a linear occlusion surface; and,
the elongated occlusion beam of the second runner is arcuate and includes a linear occlusion surface.

45. The occlusion clamp of claim 25, wherein:
the spring is fabricated from at least one of a metal and a metal alloy; and,
at least one of the first runner and the second runner is fabricated from a polymer.

46. The occlusion clamp of claim 25, further comprising a fabric interposing the first and second runners.

47. The occlusion clamp of claim 25, further comprising a C-shaped fabric sleeve encapsulating the occlusion clamp.

* * * * *